(12) United States Patent
Chu et al.

(10) Patent No.: US 10,933,140 B2
(45) Date of Patent: Mar. 2, 2021

(54) POLYSACCHARIDE-BASED HYDROGELS AND HYBRID HYDROGELS AND PRECURSORS THEREOF, METHODS OF MAKING SAME, AND USES THEREOF

(71) Applicant: Cornell University, Ithaca, NY (US)

(72) Inventors: Chih-Chang Chu, Ithaca, NY (US); DeQun Wu, Ithaca, NY (US); Mingyu He, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 15/827,245

(22) Filed: Nov. 30, 2017

(65) Prior Publication Data
US 2018/0207281 A1 Jul. 26, 2018

Related U.S. Application Data

(63) Continuation of application No. 14/404,094, filed as application No. PCT/US2013/043665 on May 31, 2013, now abandoned.

(60) Provisional application No. 61/653,498, filed on May 31, 2012.

(51) Int. Cl.
| A61K 47/36 | (2006.01) |
| A61L 15/26 | (2006.01) |
| A61K 47/34 | (2017.01) |
| A61K 9/06 | (2006.01) |
| A61L 15/28 | (2006.01) |
| A61L 15/60 | (2006.01) |
| A61L 15/22 | (2006.01) |
| C08L 5/08 | (2006.01) |
| C08L 77/12 | (2006.01) |

(52) U.S. Cl.
CPC ............ A61K 47/36 (2013.01); A61K 9/06 (2013.01); A61K 47/34 (2013.01); A61L 15/225 (2013.01); A61L 15/26 (2013.01); A61L 15/28 (2013.01); A61L 15/60 (2013.01); A61L 2300/00 (2013.01)

(58) Field of Classification Search
None
See application file for complete search history.

(56) References Cited

U.S. PATENT DOCUMENTS

| 6,602,952 B1 | 8/2003 | Bentley et al. |
| 2005/0215752 A1 | 9/2005 | Popp et al. |
| 2008/0050419 A1 | 2/2008 | Katsarava et al. |
| 2008/0193536 A1 | 8/2008 | Khademhosseini et al. |

FOREIGN PATENT DOCUMENTS

| WO | 2010/061005 A1 | 6/2010 |
| WO | 2010/083039 A1 | 7/2010 |

OTHER PUBLICATIONS

Pang et al. (Polymer Chemistry vol. 48, Issue 17 pp. 3758-3766 (2010)).*
Yamanouchi, D., et al., Biodegradable arginine-based poly(ester-amide)s as non-viral gene delivery reagents, Biomaterials, May 5, 2008, vol. 29, issue 22, pp. 3269-3277.
Sigma-Aldrich product page for dextran. Retrieved May 24, 2017 from <http://www.sigmaaldrich.com/technical-documents/protocols/biology/dextran.html>.

* cited by examiner

Primary Examiner — David J Blanchard
Assistant Examiner — Garen Gotfredson
(74) Attorney, Agent, or Firm — Hodgson Russ LLP

(57) ABSTRACT

Hydrogels and hybrid hydrogels, methods of making the hydrogels/hybrid hydrogels, and methods of using the hydrogels/hybrid hydrogels. The hydrogels have polysaccharide moieties (e.g., chitosan or hyaluronic acid moieties). The hybrid hydrogels have polysaccharide moieties (e.g., chitosan or hyaluronic acid moieties) and poly(ester amide) moieties. The poly(ester amide) moieties can have one or more arginine moieties. The hydrogels/hybrid hydrogels can be used, for example, in consumer products and as cargo carrier materials (e.g., as therapeutic agent carriers).

13 Claims, 21 Drawing Sheets

POLYSACCHARIDE-BASED HYDROGELS AND HYBRID HYDROGELS AND PRECURSORS THEREOF, METHODS OF MAKING SAME, AND USES THEREOF

CROSS-REFERENCE TO RELATED APPLICATIONS

This application is a continuation of U.S. patent application Ser. No. 14/404,094, filed on Nov. 26, 2014, which is a National Phase of International Patent Application No. PCT/US2013/043665, filed on May 31, 2013, which claims priority to U.S. Provisional Patent Application No. 61/653,498, filed on May 31, 2012, the disclosures of which are incorporated herein by reference.

FIELD OF THE DISCLOSURE

The disclosure generally relates to functionalized polysaccharides, hydrogels of polysaccharide compounds and hybrid hydrogels of polysaccharide compounds and poly (ester amides), methods of making such hydrogels/hybrid hydrogels, and uses of such hydrogels/hybrid hydrogels. More particularly, the disclosure relates to functionalized polysaccharides such as chitosan and hyaluronic acid, hydrogels and hybrid hydrogels of these molecules, and uses of such hydrogels/hybrid hydrogels.

BACKGROUND OF THE DISCLOSURE

Integration of polysaccharides with amino acid-based poly(ester amide)s (AA-PEAs) in a hydrogel form would offer the major advantage of having both polysaccharide and AA-PEA in a single entity. As polysaccharides are the major extracellular component, and AA-PEA is a pseudo-protein, such hybrid hydrogels have two "simulated" important extracellular components in a single entity. Such an integration of polysaccharides with AA-PEAs in a 3D microporous hydrogel form could significantly broaden the utility of both AA-PEA and polysaccharides. Some applications are carriers for drugs, growth factors, and cells, substrates to grow tissues in tissue engineering, and substrates for cell-culture based uses like the production of proteins and polypeptides.

Dextran is a biodegradable polysaccharide and composed of linear α-1,6-linked D-glucopyranose residues with a low percentage of α-1,2, α-1,3, and α-1,4 linked side chains. Dextran is a colloidal, hydrophilic, biocompatible, and non-toxic polymer, and can be biodegraded by dextranase. Dextran has chemically active functional hydroxyl groups in each repeating unit, and has been used in many biomedical applications like plasma expander and drug carrier, because of its good water solubility and high biocompatibility. A few water soluble cationic unsaturated arginine-based poly(ester amide) (UArg-PEA) precursor was very recently developed. Amino acid based PEAs (AA-PEAs) have been evaluated for many biomedical applications, such as wound dressing for burn treatment, drugs and gene delivery vehicles, coating of drug eluting stents, cellular responsive material, cell adhesion enhancer. Positive, negative, and neutral AA-PEAs to cell adhesion and proliferation were also studied.

BRIEF SUMMARY OF THE DISCLOSURE

Disclosed are hydrogels made from cross-linked polysaccharides and hybrid hydrogels made from cross-linked polysaccharides and poly(ester amide) (PEA) polymers. Also disclosed are methods of making functionalized compounds used to make the hydrogels/hybrid hydrogels, and methods of making and using the hydrogels/hybrid hydrogels.

In an aspect, the disclosure provides hydrogels and hybrid hydrogels. The hydrogels are formed by cross-linking groups (e.g., carbon-carbon double bonds) on polysaccharides and, in the case of hybrid hydrogels, polysaccharides and poly(ester amides). The hydrogels comprise polysaccharide moieties. These moieties can be derived by photo-crosslinking of functionalized polysaccharide compounds. The hybrid hydrogels comprise polysaccharide moieties and poly(ester amide) moieties. These moieties can be derived by photocrosslinking functionalized polysaccharide compounds and/or functionalized poly(ester amide) polymers.

In an aspect, disclosed are methods of making hydrogels and hybrid hydrogels. The methods can be used to make the hydrogels and hybrid hydrogels of the instant disclosure. In the methods, functionalized polysaccharides or mixtures of functionalized polysaccharides and functionalized poly(ester amide) polymer are photochemically crosslinked. For example, in the methods methacrylate functionalized polysaccharides or mixtures of methacrylate functionalized polysaccharides and methacrylate functionalized poly(ester amide) polymer are photochemically crosslinked.

In an aspect, the present invention provides methods of making functional polysaccharide compounds. The functional polysaccharide compounds can be used to make hydrogels. The methods can be used to provide functionalized polysaccharide compounds (e.g., functionalized chitosan compounds) with a desirable degree of substitution (DS) of hydroxyl and/or amino pendant groups on the polysaccharide.

In an aspect, the disclosure provides uses of the hydrogels and hybrid hydrogels. For example, the hydrogels can be used in articles of manufacture (e.g., as an absorbing material in a diaper or tampon) and medical applications (e.g., in drug delivery applications and as substrates in tissue engineering applications or in cell-culture based uses).

DETAILED DESCRIPTION OF THE DISCLOSURE

Figure 1:
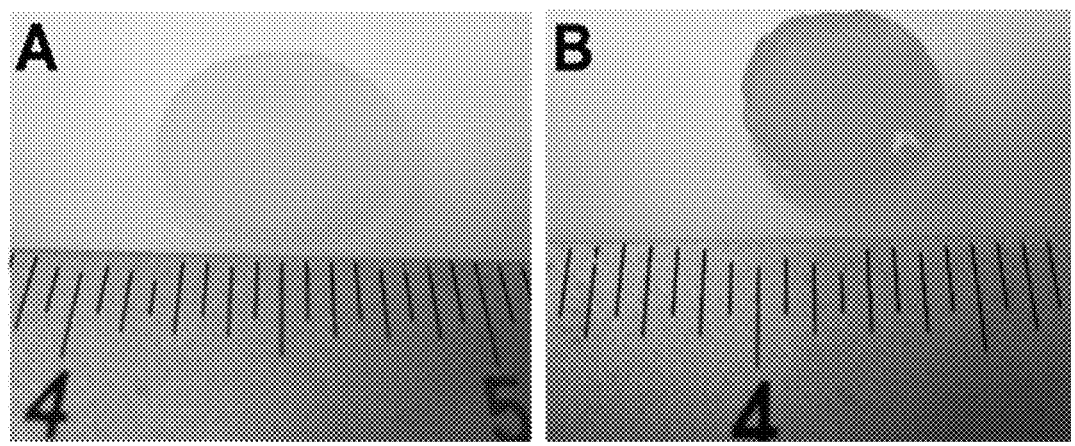
FIG. 1 show a representative image of the hydrogels. (A): pure Dex-MA; (B): Dex-MA/[2-Arg-4]-[2-Lys-4]-MA hybrid hydrogel (Gel1).

Disclosed are hydrogels made from cross-linked polysaccharides and hybrid hydrogels made from cross-linked polysaccharides and poly(ester amide) (PEA) polymers. Also disclosed are methods of making functionalized compounds used to make the hydrogels/hybrid hydrogels, and methods of making and using the hydrogels/hybrid hydrogels.

In an aspect, the disclosure provides hydrogels and hybrid hydrogels. The hydrogels are formed by crosslinking groups (e.g., carbon-carbon double bonds) on polysaccharides and, in the case of hybrid hydrogels, poly(ester amides). In an embodiment, the hydrogel is a hydrogel made by a method disclosed herein. In an embodiment, the hybrid hydrogel is a hybrid hydrogel made by a method disclosed herein.

The hydrogels comprise polysaccharide moieties. These moieties can be derived from photocrosslinking of functionalized polysaccharide compounds. For example, the functionalized polysaccharide compound can be a functionalized polysaccharide compound disclosed herein.

In an embodiment, the hydrogel comprises a plurality of covalently photocrosslinked functionalized polysaccharide molecules, wherein the functionalized polysaccharide molecules are selected from functionalized chitosan molecules having at least 10 pendant photocrosslinkable groups and functionalized hyaluronic acid molecules having at least 10 pendant photocrosslinkable groups.

In an embodiment, the hybrid hydrogel comprising a) a plurality of covalently photocrosslinked functionalized polysaccharide molecules, wherein the functionalized polysaccharide molecules are selected from functionalized chitosan molecules having at least 10 pendant photocrosslinkable groups, and functionalized hyaluronic acid molecules having at least 10 pendant photocrosslinkable groups, and b) functionalized poly(ester amide) polymer comprising one or more arginine moieties.

In an embodiment, the hydrogel/hybrid hydrogel comprises a plurality of covalently cross-linked chitosan moieties or hyaluronic acid moieties. For example, the hydrogel/hybrid hydrogel can be comprised of chitosan moieties each independently having covalent bonds to other moieties (e.g., chitosan moieties or poly(ester amide) moieties) formed by photochemical crosslinking, where the number of covalent bonds is at least 10, 15, 20, 25, 30, 31, 32, 33, 34, 35, 36, 37, 38, 39, or 40% of the total hydroxyl and/or or amine sites of the chitosan moiety groups. For example, the hydrogel/hybrid hydrogel can be comprised of chitosan moieties each independently having covalent bonds to other moieties (e.g., chitosan moieties or poly(ester amide) moieties) formed by photochemical crosslinking, where the number of covalent bonds is 10 to 40%, including all integer % values and ranges therebetween, of the total hydroxyl and/or or amine sites of the chitosan moiety groups. For example, the hydrogel/hybrid hydrogel can be comprised of hyaluronic moieties each independently having covalent bonds to other moieties (e.g., hyaluronic moieties or poly(ester amide) moieties) formed by photochemical crosslinking, where the number of covalent bonds is at least 10, 15, 20, 25, 30, 35, 40, 45, 46, 47, 48, 49, or 50% of the total number of carboxylate groups. For example, the hydrogel/hybrid hydrogel can be comprised of hyaluronic moieties each independently having covalent bonds to other moieties (e.g., hyaluronic moieties or poly(ester amide) moieties) formed by photochemical crosslinking, where the number of covalent bonds is 10 to 50%, including all integer % values and ranges therebetween, of the total carboxylic acid sites of the hyaluronic acid moiety groups.

The hybrid hydrogels comprise polysaccharide moieties and poly(ester amide) moieties. These moieties can be derived from functionalized polysaccharide compounds and poly(ester amide) polymers (e.g., the functionalized polysaccharide compounds and poly(ester amide) polymers disclosed herein), respectively.

In an embodiment, the hybrid hydrogel comprises a plurality of polysaccharide moieties and a plurality of poly (ester amide) moieties. The poly(ester amide) moieties can comprise a plurality of amino acid moieties.

The hydrogels and hybrid hydrogels can have a variety of polysaccharide moieties. The hydrogels and hybrid hydrogels can have a mixture of polysaccharide moieties. For example, the moieties can be formed using the methods for making hydrogels and hybrid hydrogels disclosed herein.

Examples of suitable polysaccharide moieties include chitosan moieties, hyaluronic acid moieties, and dextran moieties.

The polysaccharide moieties can be derived from the corresponding polysaccharide compounds (e.g., functionalized polysaccharide compounds). For example, the functionalized polysaccharide compounds can be made by the methods disclosed hererein.

The hybrid hydrogels can have a variety of poly(ester amide) moieties. The hybrid hydrogels can have a mixture of poly(ester amide) moieties. The poly(ester amide) moieties can be formed from the corresponding poly(ester amide) polymers (e.g., functionalized poly(ester amide) polymers).

The poly(ester amide) moiety may comprise amino acid moieties. In certain embodiments, it may be desirable that the poly(ester amide) comprise on or more arginine moieites. For example, PEAs derived from the amino acid arginine can be used. In an embodiment, the PEA comprises a plurality of arginine groups.

For example, the poly(ester amide) moieties have the following structure:

Structure I

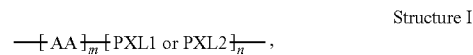

where the polymers have at least one pendant cross-linking (PXL) group (R'),

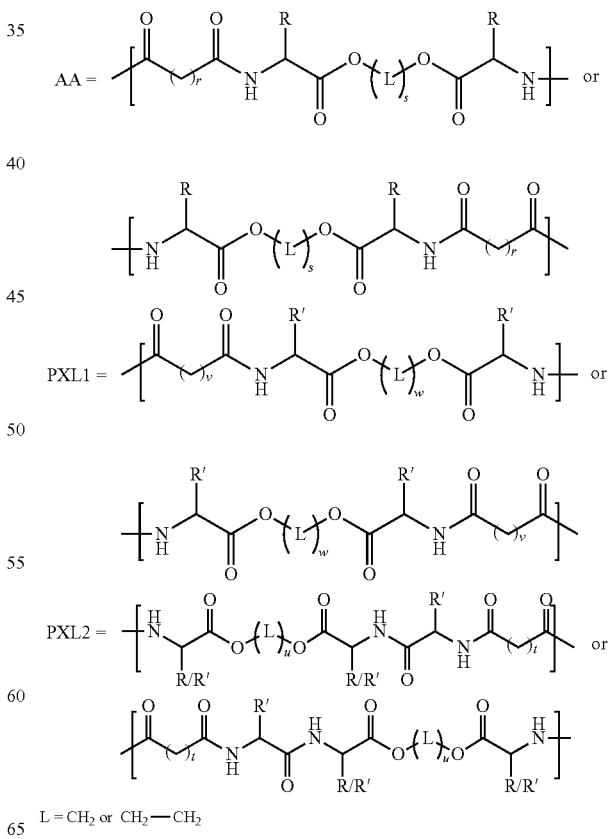

L = CH$_2$ or CH$_2$—CH$_2$

In Structure I, m/n is from 4 to 1. The values of r, v and t are, for example, 2, 4 or 8, and s, w and u are, for example, 2, 4 or 6, respectively. R is any side chain from any naturally occurring amino acid (e.g., $CH_2$-Ph (phenylalanine) or an alkylguanidinium group (arginine). The R group does not have a moiety which can undergo crosslinking reactions or reactions with functionalizing agents that result in formation of a pendant functional group.

The R' group is covalently bound to another PEA moiety or a functionalized polysaccharide moiety. There is a carbon-carbon formed between another PEA moiety or polysaccharide moiety. In an embodiment, the R' group has the following structure —$(CH_2)_4$—NH—C(O)—$CH(CH_3)$—$(CH_2)$—. In an embodiment, the R' group has the following structure —$(CH_2)_4$—O—C(O)—$CH(CH_3)$—$(CH_2)$—.

In one embodiment, the PEA moiety can have the following general structure which includes Structure II (also referred to as x-AA-y-AG, where AA is an amino acid, x is the number of carbons in the diacid and y is the number of carbon atoms in the diol group linking the two amino acids in the diester monomer):

Structure II

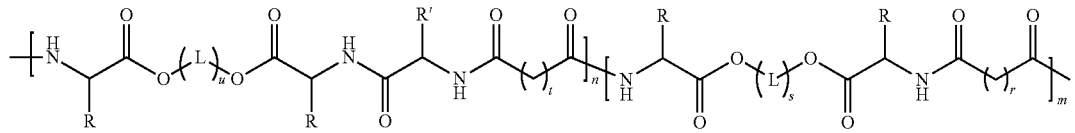

An example of this structure is 8-Phe-4-AG (shown below as Structure III) where in the PXL2 block R is $CH_2$-Ph, L is $CH_2$, u is 4, R is $CH_2$-Ph, R' is allyl, t is 8 and n is 0.25. In the AA block, R is $CH_2$-Ph, L is $CH_2$, s is 4, R is CH-Ph and r is 8 and m is 0.75.

Structure III

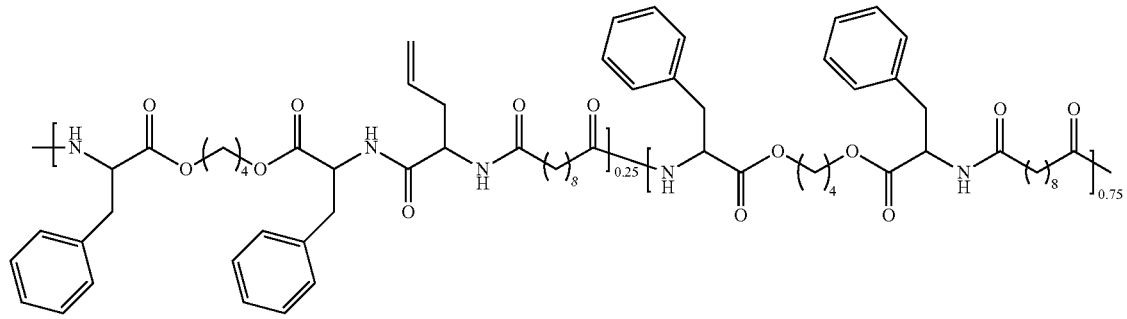

Another example is 8-Arg-4-AG (shown below as Structure IV) where in the PXL2 block, L is $CH_2$, u is 4, R is an alkylguanidinium group $(CH_2)_3NH(C(NH_2)=NH^+)$, R' is allyl, t is 8 and n is 0.25. In the AA block, L is $CH_2$, s is 4, R is an alkylguanidinium group $(CH_2)_3NH(C(NH_2)=NH^+)$ and r is 8, and m is 0.75.

Structure IV

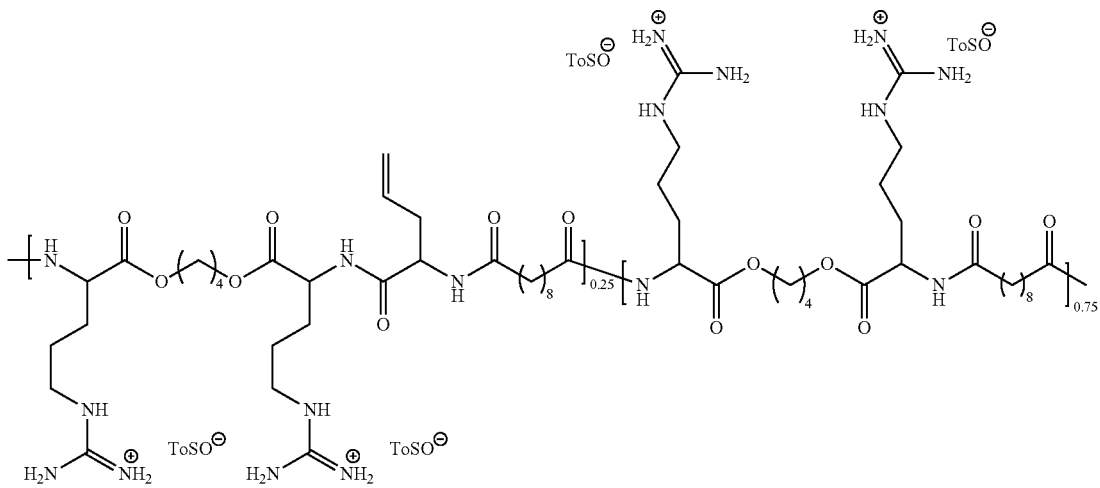

In another embodiment, the PEA moiety can have the following general structure which includes Structure V (also referred to as x-AA-y-AG-z, where AA is an amino acid, x is the number of carbons in the diacid and y is the number of carbon atoms in the diol group linking the two amino acids in the diester monomer and z is the number of carbons in the diol group linking the two amino acids in the monomer from which the PXL1 block is derived):

Structure V

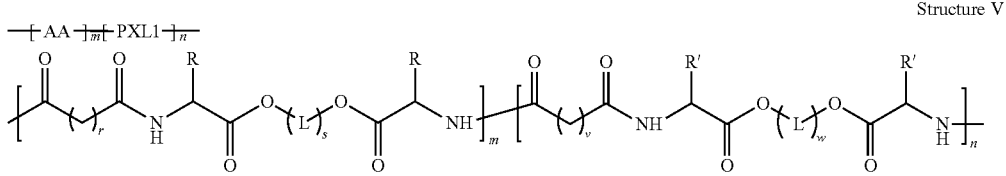

An example of this structure is 8-Phe-4-AG-4 (shown below as Structure VI) where in the AA block, r is 8, R is $CH_2$-Ph, L is $CH_2$, s is 4, R is $CH_2$-Ph and m is 0.75. In the PXL1 block, v is 8, R' is allyl, L is $CH_2$, w is 4, R is allyl and n is 0.25.

The PEA moieties have a number averaged molecular weight, Mn, of from 1 kg/mol to 500 kg/mol, including all integer kg/mol values and ranges therebetween. The PEA moieties have a weight averaged molecular weight, Mw, of from 1 kg/mol to 500 kg/mol, including all integer kg/mol values and ranges therebetween. The Mn and/or Mw can be determined by, for example, gel permeation chromatography. In an embodiment, the PEA polymers having Structure I have a number averaged molecular weight, Mn, of from 10 kg/mol to 100 kg/mol, including all integer kg/mol values and ranges therebetween, and/or a weight averaged molecular weight, Mw, of from 10 kg/mol to 100 kg/mol, including all integer kg/mol values and ranges therebetween. In an embodiment, the polymers having Structure I have a Mn of from 20 kg/mol to 50 kg/mol, including all ranges and values to the 0.1 kg/mol therebetween, and/or a Mw of from 20 kg/mol to 50 kg/mol, including all ranges and values to the 0.1 kg/mol therebetween.

The PEA moieties having Structure I can have, for example, an end group of hydrogen (for an amide terminated block) or O(p-nitro)Ph (for a carbonyl terminated block) as shown in Structure VII.

Structure VI

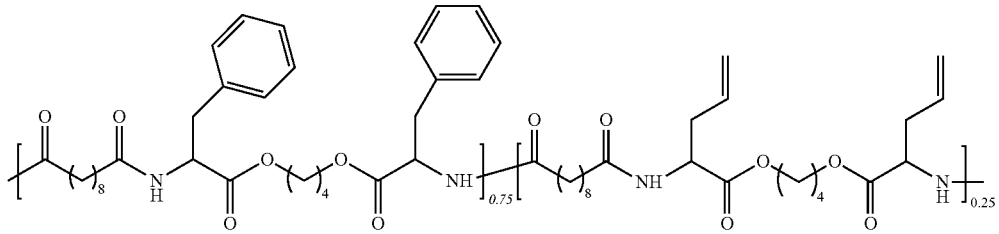

Structure VII

As another example, the end groups of Structure I can both be hydrogen or O(p-nitro)Ph, or end group can be hydrogen and one end group can be O(p-nitro)Ph. The end groups depend on the molar ratio of different monomers. For example, if the amount of Structure VII monomer used is greater than the amount of diester used, both end groups are hydrogens. As another example, if the amount of Structure VII monomer used is equal to the amount of diester used, the end groups are hydrogen on one end of the polymer and O(p-nitro)Ph on the other end. As yet another example, if the amount of Structure VII monomer used is less than the amount of diester used, the end groups are O(p-nitro)Ph.

The hydrogels and hybrid hydrogels can have a porous structure. For example, the hydrogels and hybrid hydrogels can have an average pore diameter of 5 μm to 75 μm, including all integer average pore diameter values and ranges therebetween. The pores can have irregular shapes. The pore diameters and average pore diameters can be determined by methods known in the art.

The hydrogels and hybrid hydrogels have desirable properties. The hydrogels or hybrid hydrogels can exhibit a swelling ratio of 200% to 10,000%, including all values to the 100% and ranges therebetween. For example, the hydrogels or hybrid hydrogels can exhibit a swelling ratio of at least 200%, 300%, 400%, 500%, 600%, 700%, 800%, 900%, 1000%, 1500%, 2000%, 3000%, 4000%, 5000%, 6000%, 7000% or 8000%. For example, the hydrogels or hybrid hydrogels can be optically transparent.

In an aspect, disclosed are methods of making hydrogels and hybrid hydrogels. The methods can be used to make the hydrogels and hybrid hydrogels of the instant disclosure. In the methods, functionalized polysaccharides or mixtures of functionalized polysaccharides and functionalized poly(ester amide) polymer are photochemically crosslinked. For example, the methods photochemically cross-link methacrylate functionalized polysaccharides or mixtures of methacrylate functionalized polysaccharides and methacrylate functionalized poly(ester amide) polymer. In an embodiment, the functionalized polysaccharides and/or functionalized poly(ester amide) polymer are methacrylate functionalized.

In an embodiment, the method of making a hydrogel comprises the steps of:
  a) forming a mixture of a functionalized polysaccharide compound and a initiator; and
  b) exposing the mixture to ultraviolet radiation, such that a hydrogel is formed.

In an embodiment, the functionalized polysaccharide is water soluble and the mixture is formed in an aqueous solvent (e.g., water).

The mixture can also comprise a functionalized poly(ester amide) polymer. Thus, in an embodiment, the method of making a hybrid hydrogel comprises the steps of:
  a) forming a mixture of a functionalized polysaccharide compound, functionalized poly(ester amide) polymer, and a initiator; and
  b) exposing the mixture to ultraviolet radiation, such that a hydrogel is formed.

In an embodiment, the functionalized polysaccharide and functionalized poly(ester amide) are water soluble and the mixture is formed in an aqueous solvent (e.g., water).

Functionalized polysaccharides have one or more groups that can be photochemically cross linked. Examples of such groups include groups having one or more carbon-carbon double bonds (e.g., carbon-carbon double bonds of an allyl moiety, vinyl moiety, or methacrylate moiety).

The functionalized PEAs have one or more groups that can be photochemically crosslinked. Examples of such groups include groups having one or more carbon-carbon double bonds (e.g., carbon-carbon double bonds from an allyl moiety, vinyl moiety, or methacrylate moiety). The photocrosslinkable groups can be on any moiety of the poly(ester amide).

Suitable functionalized PEAs can have the following structure:

Structure I-FP

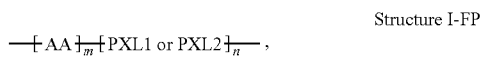

where the polymers have at least one pendant cross-linking (PXL) group (R'),

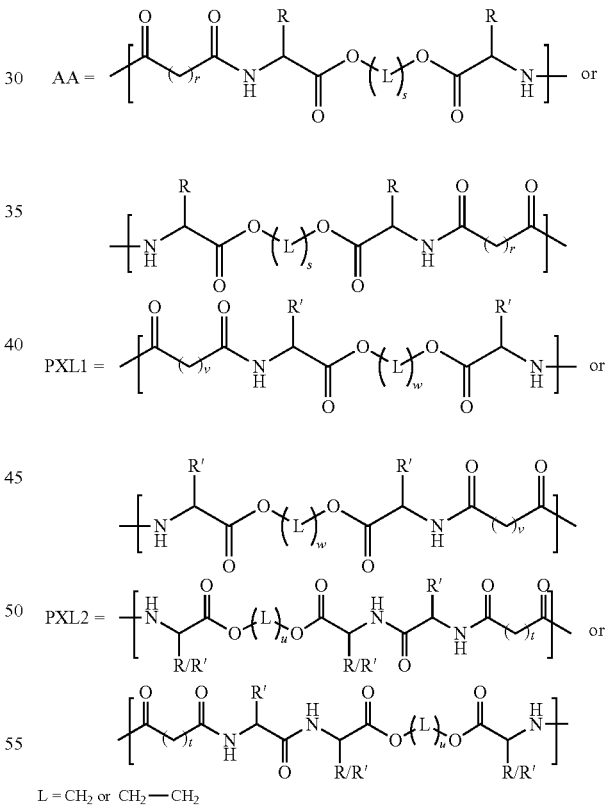

In Structure I-PP, m/n is from 4 to 1. The values of r, v and t are, for example, 2, 4 or 8, and s, w and u are, for example, 2, 4 or 6. R is any side chain from any naturally occurring amino acid (e.g., CH$_2$-Ph (phenylalanine) or an alkylguanidinium group (arginine). The R group may not have a moiety which can undergo crosslinking reactions or reactions with functionalizing agents that result in formation of a pendant functional group.

The R' group has a pendant cross-linkable group which has a moiety such as, for example, a carbon-carbon double bond (e.g., an allyl group of allylglycine). For example, R' can be a substituted or unsubstituted alkyl group terminated in a carbon-carbon double bond comprising from 3 to 10 carbons, including all integers therebetween.

In an embodiment, the R' group is an alpha-methylenated terminated group (e.g., alpha-methylenated ester, amide, or thioester group). The alpha-methylenated terminated group terminated group can be a methacryl terminated group (e.g., a methacrylate, methacrylamide, or methacrylthioester). In an embodiment, the R' group has the following structure —(CH$_2$)$_4$—NH—C(O)—C(CH$_3$)(CH$_2$). In an embodiment, the R' group has the following structure —(CH$_2$)$_4$—O—C(O)—C(CH$_3$)(CH$_2$). Such groups can be formed by reacting methacrylic anhydride with a PEA polymer having a hydroxy, amine, or thiol terminated group in the R' position. Examples of such reactions are provided herein.

The PEA polymers have a number averaged molecular weight, Mn, of from 1 kg/mol to 500 kg/mol, including all integers and ranges therebetween. The PEA polymers have a weight averaged molecular weight, Mw, of from 1 kg/mol to 500 kg/mol, including all integers and ranges therebetween. The Mn and/or Mw can be determined by, for example, gel permeation chromatography. In an embodiment, the PEA polymers having Structure I have a number averaged molecular weight, Mn, of from 10 kg/mol to 100 kg/mol, including all integers and ranges therebetween, and/or a weight averaged molecular weight, Mw, of from 10 kg/mol to 100 kg/mol, including all integers and ranges therebetween. In an embodiment, the polymers having Structure I have a Mn of from 20 kg/mol to 50 kg/mol, including all ranges and values to the 0.1 therebetween, and/or a Mw of from 20 kg/mol to 50 kg/mol, including all ranges and values to the 0.1 therebetween.

In one embodiment, the PEA polymer can have the following general structure which includes Structure II (also referred to as x-AA-y-AG, where AA is an amino acid, x is the number of carbons in the diacid and y is the number of carbon atoms in the diol group linking the two amino acids in the diester monomer):

Structure II-FP

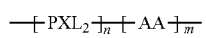

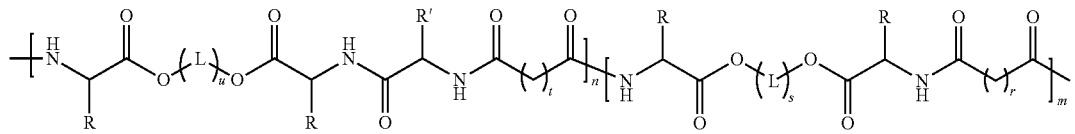

An example of this structure is 8-Phe-4-AG (shown below as Structure III) where in the PXL2 block R is CH$_2$-Ph, L is CH$_2$, u is 4, R is CH$_2$-Ph, R' is allyl, t is 8 and n is 0.25. In the AA block, R is CH$_2$-Ph, L is CH$_2$, s is 4, R is CH$_2$-Ph and r is 8 and m is 0.75.

Structure III-FP

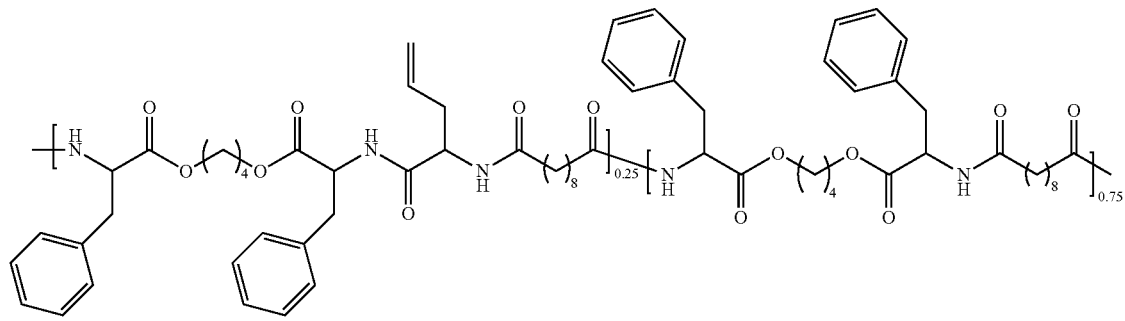

Another example is 8-Arg-4-AG (shown below as Structure IV-FP) where in the PXL2 block, L is $CH_2$, u is 4, R is an alkylguanidinium group $(CH_2)_3NH(C(NH_2)=NH^+)$, R' is allyl, t is 8 and n is 0.25. In the AA block, L is $CH_2$, s is 4, R is an alkylguanidinium group $(CH_2)_3NH(C(NH_2)=NH^+)$ and r is 8, and m is 0.75.

Structure IV-FP

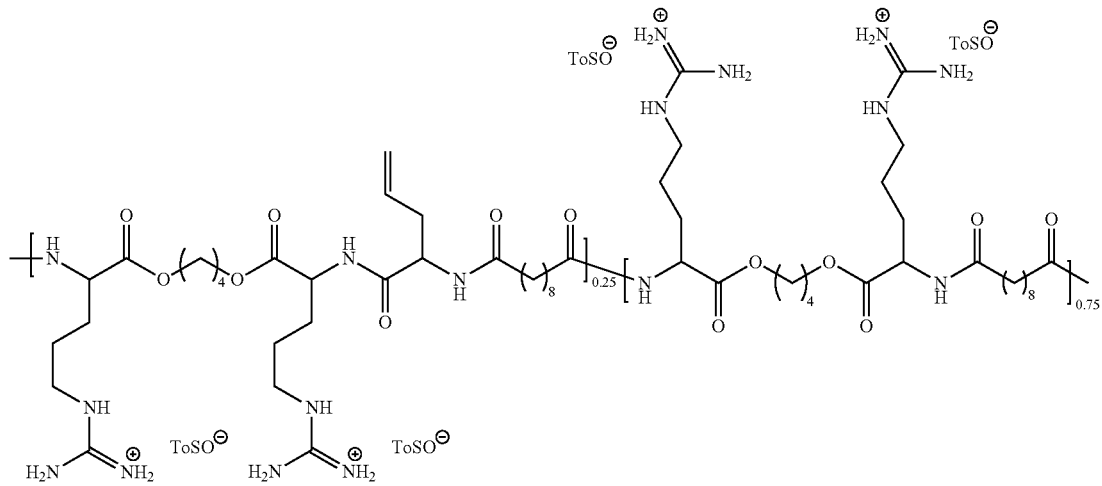

In another embodiment, the PEA polymer can have the following general structure which includes Structure V-FP (also referred to as x-AA-y-AG-z, where AA is an amino acid, x is the number of carbons in the diacid and y is the number of carbon atoms in the diol group linking the two amino acids in the diester monomer and z is the number of carbons in the diol group linking the two amino acids in the monomer from which the PXL1 block is derived):

Structure V-FP

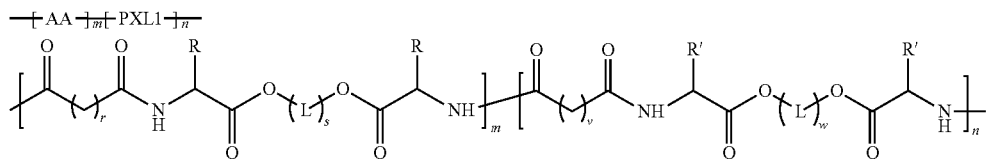

An example of this structure is 8-Phe-4-AG-4 (shown below as Structure VI) where in the AA block, r is 8, R is $CH_2$-Ph, L is $CH_2$, s is 4, R is $CH_2$-Ph and m is 0.75. In the PXL1 block, v is 8, R' is allyl, L is $CH_2$, w is 4, R is allyl and n is 0.25.

Structure VI-FP

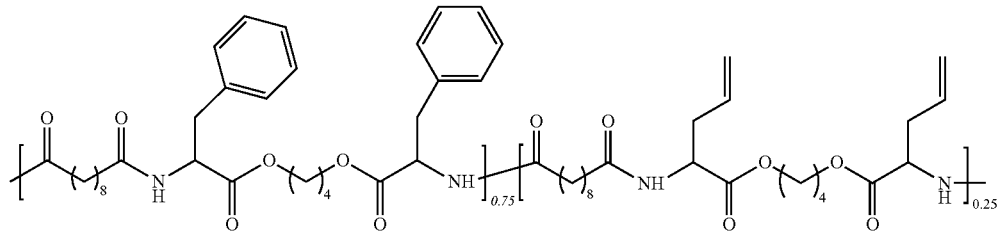

The PEA polymer having Structure I-FP can have, for example, an end group of hydrogen (for an amide terminated block) or O(p-nitro)Ph (for a carbonyl terminated block) as shown in Structure VIII.

Structure VII-FP

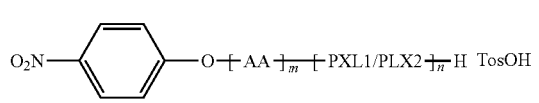

As another example, the end groups of Structure I can both be hydrogen or O(p-nitro)Ph, or end group can be hydrogen and one end group can be O(p-nitro)Ph. The end groups depend on the molar ratio of different monomers. For example, if the amount of Structure VIII-FP monomer used is greater than the amount of diester used, both end groups are hydrogens. As another example, if the amount of Structure VIII-FP monomer used is equal to the amount of diester used, the end groups are hydrogen on one end of the polymer and O(p-nitro)Ph on the other end. As yet another example, if the amount of Structure VII-FP monomer used is less than the amount of diester used, the end groups are O(p-nitro)Ph.

Suitable functionalized PEAs can be made by methods known in the art. For example, suitable PEAs are described in U.S. patent application Ser. No. 13/321,998 (published as U.S. Published Patent Application No. 20120130020) the disclosure of which with respect to PEAs structures and methods of making PEAs is incorporated herein by reference.

The feed ratio (i.e., the functionalized polysaccharide:functionalized PEA ratio) can be varied to obtain hybrid hydrogels with varying properties. For example, the feed ratio can be from 1:1 to 5:1, including all integer functionalized polysaccharide and functionalized PEA values therebetween.

A variety of initiators can be used. The initiator forms a reactive species when exposed to ultraviolet radiation of a suitable wavelength. Initiators suitable for crosslinking the functionalized polysaccharides and, optionally, functionalized PEAs are known in the art. Examples of suitable initiators include ammonium persulfate and Irgacure 2959.

The mixture is exposed to ultraviolet radiation that results in a desired degree of crosslinking (i.e., covalent bond formation). Methods of providing the requisite dose of ultraviolet radiation are provided herein and known in the art.

A variety of reaction conditions (e.g., reaction temperature and atmosphere) can be used. Determination of the appropriate conditions is within the purview of one having skill in the art.

In an aspect, the present invention provides methods of making functional polysaccharide compounds. The functional polysaccharide compounds can be used to make hydrogels. The methods can be used to provide functionalized polysaccharide compounds (e.g., functionalized chitosan compounds) with a desirable degree of substitution (DS) of the hydroxyl and/or amino pendant groups on the polysaccharide.

In an embodiment, the method of making functional polysaccharide compounds comprises the steps of:
c) forming a mixture comprising a polysaccharide, a functionalizing agent, optionally, an acid source, an aprotic solvent, optionally, a coupling agent, and, optionally, a catalyst; and d) reacting the mixture under conditions such that a functionalized polysaccharide is formed.

A variety of polysaccharides can be used. Examples of suitable polysaccharides include chitosan and hyaluronic acid.

The functionalizing agent comprises a functional group that react with the polysaccharide (e.g., an epoxide of a glycidyl group) and a functional group that directly or indirectly provides a functional group that can be crosslinked (e.g., carbon-carbon bond such as that in a methacrylate group) on the functionalized polysaccharide. The functionalizing agent can have one or more such functional groups. A variety of functionalizing agents can be used. An example of a suitable functionalizing agent is glycidyl methacrylate.

The polysaccharides can have a range of degree of substitution. By degree of substitution it is meant the percentage of functional groups (of the total number of functional groups that could be incorporated in the polysaccharide based on the number of desired or available hydroxyl and/or amine sites) that are incorporated in the polysaccharide (e.g., methacrylate groups incorporated in a chitosan molecule). The degree of substitution can be determined by methods known in the art (e.g., using NMR spectroscopy) For example, the polysaccharide (e.g., chitosan and hyaluronic acid) can have degree of substitution is from 5% to 50%, including all integer % values and ranges therebetween. Without intending to be bound by any particular theory, it is considered that the DS of the resulting functionalized polysaccharide can be controlled by the polysaccharide:functionalizing agent ratio.

A variety of aprotic solvents can be used. In an embodiment, the aprotic solvent is a polar aprotic solvent. An example of a suitable solvent is dimethylsulfoxide (DMSO).

A variety of acid sources can be used. The acid source can protonate the amine functional groups so that the hydroxyl groups on the polysaccharide are selectively functionalized. Examples of suitable acid sources include sulfonic acids, such asp-toluene sulfonic acid.

A variety of coupling agents can be used. For example, peptide coupling agents known in the art can be used.

A variety of catalysts can be used. An example of a suitable catalyst is 4-(N,N-dimethylamino) pyridine (DMAP).

If the polysaccharide has free amine groups it may be desirable to protonate the amine groups to prevent reaction of these groups. Without intending to be bound by an particular theory, it is considered that the acid source protonates the free amine groups on the polysaccharide resulting in functionalization of the hydroxyl groups. In an embodiment, the polysaccharide is chitosan. When chitosan is the polysaccharide, an acid source and catalyst are used. In an embodiment, a chitosan salt (the chitosan amines are protonated) can be used and an acid source is not required. For example, a functionalized chitosan compound can be formed using dimethylsulfoxide (DMSO) as the polar aprotic solvent, p-toluene sulfonic acid as the acid source, and 4-(N,N-dimethylamino) pyridine (DMAP) as the catalyst. For example, the functionalized chitosan is water soluble and has a DS of 5% to 50%, including all integer % values and ranges therebetween.

In an embodiment, the polysaccharide is hyaluronic acid. In this embodiment, no acid source or catalyst is used. In certain embodiments, the coupling agent is a peptide coupling agent or system (e.g., EDC/NHS) is used to selectively functionalize the hyaluronic acid carboxylic acid group. Examples of suitable peptide coupling agents/systems are known in the art.

A variety of reaction conditions (e.g., reaction temperature and atmosphere) can be used. Determination of the appropriate conditions is within the purview of one having skill in the art.

The steps of the various methods described herein (e.g., in the various embodiments and examples) are sufficient to carry out the methods of the present invention. Thus, in an embodiment, a particular method consists essentially of a combination of the steps of the method disclosed herein. In another embodiment, the particular method consists of such steps.

In an aspect, the disclosure provides uses of the hydrogels and hybrid hydrogels. For example, the hydrogels can be used in articles of manufacture (e.g., as an absorbing material in a diaper) and medical applications (e.g., in drug delivery applications and as substrates in tissue engineering applications or in cell-culture based uses). The hydrogels and hybrid hydrogels can be used to carry and/or release molecules or compounds.

In an embodiment, the a carrier material comprises: a) a hydrogel comprising a plurality of covalently photocrosslinked functionalized polysaccharide molecules, wherein the functionalized polysaccharide molecules are selected from functionalized chitosan molecules having at least 10 pendant photocrosslinkable groups and functionalized hyaluronic acid molecules having at least 10 pendant photocrosslinkable groups, or a hybrid hydrogel comprising: i) a plurality of covalently photocrosslinked functionalized polysaccharide molecules, wherein the functionalized polysaccharide molecules are selected from functionalized chitosan molecules having at least 10 pendant photocrosslinkable groups; and ii.) functionalized hyaluronic acid molecules having at least 10 pendant photocrosslinkable groups, and functionalized poly(ester amide) polymer comprising arginine moieties, and b) a cargo.

For example, a material comprising a hydrogel and/or hybrid hydrogel can be implanted in an individual. The material can be implanted on a short-term or long-term basis. The material can have a variety of sizes or shapes. The size and/or shape can be as necessitated by the area to be implanted.

The cargo material can be a therapeutic agent. Examples of suitable therapeutic agents include a nutrients, pharmaceuticals, drugs, peptides, polypeptides, oligonucleotides, polynucleotides, and combinations thereof.

The hydrogels/hybrid hydrogels can be used in methods for controlled release of a molecule or compound. In an embodiment, the method comprises providing a hydrogel or hybrid hydrogel the molecule or compound is loaded in the hydrogel.

In another embodiment, a method for directing release of a molecule or compound in an area of interest is provided. The method comprises providing a hybrid hydrogel wherein the molecule or compound is loaded in the hydrogel and wherein the hydrogel is inserted in the area of interest in a subject. The area of interest can be, for example, an area of the subject's body, a body part, an organ, an organ system, a cell, or a tissue.

The hybrid hydrogels can be used as carriers of biologics for a variety of biomedical applications. The hydrogels provided by the invention can be used to carry and/or release bioactive molecules or compounds. Using the hybrid hydrogels of the invention. bioactive compounds can be carried and/or released in the area of interest. Bioactive compounds can be agents used for delivery to cells, tissues or organs for nutrient, physiological or therapeutic effect. Bioactive molecules are well known in the art and can include but are not limited to nutrients, pharmaceuticals, drugs, peptides, polypeptides, oligonucleotides and polynucleotides.

Bioactive molecules can be loaded into the hybrid hydrogels of the invention and used for rapid controlled release and/or slower sustained release. Release rates can be controlled by varying the hybrid ratio during photo-polymerization. A hybrid hydrogel of the disclosure can be selected for hydrophilicity or hydrophobicity, positive charge and/or less crosslinking density or the type of crosslinker in the hybrid hydrogel to promote release of a molecule of interest. Biologically active compounds can be pre- or postloaded into the hydrogels using methods known in the art. For pre-loading, biologically active agents can mixed with the gel precursors and gelation subsequently conducted. Owing to the cationic nature of hybrid hydrogels, any anionic biological agents known in the art, e.g., heparin, DNA, growth factors, cytokines, can be post-loaded into hydrogels of the invention after the gels are fabricated. Examples of anionic growth factors include, but are not limited to, acidic fibroblast growth factor (aFGF), hypothalamus-derived growth factor (aHDGF) The electrostatic interaction will attract the anionic biological agents into the cationic hybrid hydrogels of the disclosure. In a specific embodiment, cancer therapy drugs such as interleukin-12 (IL-12) or paclitaxel can be preloaded into a hybrid hydrogel of the invention and delivered for cancer therapy.

The release of a molecule of interest from a loaded hybrid hydrogel can be studied using standard methods known in the art. For example, release studies can be carried out in PBS buffer with or without trypsin. Hydrogel samples (e.g., small pellet) loaded with the molecule of interest can he inserted into a small vial containing PBS (or PBS-trypsin) solution. Details of the release studies are disclosed herein. Methods to determine the amount of molecule of interest released is well known in the art (e.g., ELISA methods).

In an embodiment, the disclosure provides a composition comprising a hydrogel or hybrid hydrogel and a therapeutic agent or prophylactic agent. For example, the therapeutic agent or prophylactic agent can be sequestered in the hydrogel or hybrid hydrogel.

The therapeutic agent or prophylactic agent can be administered to an individual in need of the drug. The therapeutic agent or prophylactic agent can be released from the composition over a desired period of time. Thus, in an embodiment, the disclosure provides a method for delivering a therapeutic agent or prophylactic agent comprising the step of:

a) providing a composition comprising a therapeutic agent or prophylactic agent to an individual, wherein the drug is released from the composition over a period of time.

A variety of therapeutic agents can be used in the composition.

The hydrogel or hybrid hydrogel can be incorporated in an article of manufacture. In an embodiment, the disclosure provides an article of manufacture comprising the hydrogel or hybrid hydrogel. For example, the article of manufacture can be an article used to absorb a liquid (e.g., water), such as a diaper or tampon. In an embodiment, the article of manufacture is a diaper or a tampon. For example, the hydrogel or hybrid hydrogel can be a layer (e.g., an absorbent layer) in a diaper or tampon.

The following examples are presented to illustrate the present disclosure. They are not intended to limiting in any manner.

Example 1

This example shows the feasibility of integrating amino acid-based poly(ester amide)s (AA-PEAs or pseudo-proteins) with polysaccharides so that the resulting product would have both the merits of polysaccharides and pseudo-proteins within a single entity. Arg-Lys-PEA is used as the model compound for AA-PEA, and modified Dextran (Dex-MA) is used as the model compound for polysaccharide to demonstrate the feasibility to integrate AA-PEAs with polysaccharides.

In a non-limiting embodiment of this disclosure, a unsaturated arginine-lysine-based AA-PEAs ([2-Lys-4]-[2-Arg-4]-MA) is used as the AA-PEA precursors. Dextran is used as the model compound of polysaccharides, and this dextran is chemically modified into dextran acrylate precursor (Dex-MA) to provide photo-crosslinkable carbon to carbon double bonds. Both ([2-Lys-4]-[2-Arg-4]-MA and Dex-MA precursors were photo-gelled in an aqueous medium. The capability of fabricating this type of gels in an aqueous medium is vital in any biological and biomedical applications because no organic solvents were used which could have adverse effects on cells and proteins.

Experimental: Materials. L-Arginine (Arg), L-lysine monohydrochloride (Lys), p-toluenesulfonic acid monohydrate (TosOH.H$_2$O), adipoyl chloride, 1,4-butanediol and p-nitrophenol were used without further purification. Triethylamine from Fisher Scientific was dried via refluxing with calcium hydride and then distilled. Other solvents, such as benzene, ethyl acetate, acetone, N,N-dimethylacetamide (DMAc), and dimethyl sulfoxide (DMSO), methacrylic Chloride were purified by standard methods before use. Bovine serum albumin (BSA), methacryloyl anhydride, trypsin (Type IX-S, from bovine pancreas, lyophilized power, 13,000-20,000 BAEE units/mg protein) was obtained from Sigma-aldrich. Double-distilled water was used for the following experiments. All chemicals were used without further purification. Buffer solutions, pH 3, pH 7, and pH 10, were purchased by VWR Scientific.

Instrumentation: The mechanical property of the Lysine based hydrogels was measured by a DMA Q800 Dynamic Mechanical Analyzer in a "controlled force" mode. The swollen hydrogel samples in circular disc shape were submerged in distilled water and mounted between the movable compression probe (diameter 15 mm) and the fluid cup. A compression force from 0.01 to 0.05 or 0.30 N (depending on the gel strength) at a rate of 0.02 or 0.05 N/min was applied at room temperature. The compression elastic modulus (E) of the swollen hydrogel was calculated by plotting the compressional force versus strain.

A Hitachi (Mountain View, Calif.) S4500 SEM was used to characterize the interior morphology of the hydrogel. Image analyses of SEM data were performed by using the public domain NIH image program.

FT-IR spectra of monomers and hydrogels were recorded on a spectrometer (Perkin-Elmer Magna-IR560 Spectrometer) to characterize the chemical structures of Lys-4 monomer and its hydrogels. The samples were ground into pieces, compressed onto the KBr crystal, and FT-IR spectra were recorded in the wavenumbers range of 550-4,000 cm-1.

$^1$H NMR spectra of the polymer precursors were obtained on a Bruker AC-200 spectrometer. The polymers were dissolved in DMSO-d6 containing 1% TMS as an internal reference.

Synthesis of Detran-MA Precursor: Dextran (MW 67,000) 3.24 g was dissolved in 30 mL DMAc with the LiCl concentration of 5 wt % by heating to 80° C. with stirring for 3 hours and then cooling down to ambient temperature. The solution was chilled to 0° C. and followed by adding 3 mL pyridine and 3 ml methacrylic chloride dropwisely for 3 hours. The solution was raised to room temperature and the reaction was carried out overnight at a room temperature. The Dex-MA product was obtained by precipitated the solution in excessive isopropyl alcohol and dried in vaccum overnight. By tuning the ratio of dextran to MA, varied degrees of substitution in dextran-MA were obtained. The product was characterized by $^1$H NMR and FT-IR with no purification.

Experimental Details: The fabrication of hybrid hydrogels from both AA-PEA and dextran derivative precursors involves 3 basic steps: synthesis of dextran-based precursor, synthesis of unsaturated arginine-lysine based PEA precursor (Arg-Lys-PEA), and photo-gelation of these 2 precursors in an aqueous medium at predetermined precursors' feed ratios under long wavelength UV.

Step 1: Synthesis of dextran-based precursor (dextran acrylate, Dex-MA) The objective of this step to synthesize photo-reactive dextran-based precursor having photo-reactive vinyl groups so that it can react with AA-PEA precursors upon photo-means. The method to synthesize the dextran precursor in this example is to incorporate photo-reactive double bonds to the hydroxyl groups of dextran. The method is simple and provides high yields.

Dextran of MW 66,000 purchased from Sigma Chemical was dried in 60° C. in a vacuum oven for 24 hours before use. 4 grams of the dextran was added into 40 mL LiCl/DMAc NCl at the concentration of 5% w/v %) solvent in a three-necked flask and the mixture was heated to 100° C. to get a pale yellow transparent solution under nitrogen flow. The solution was then cooled down to room temperature and 2.0 g pyridine (as an acid acceptor) was introduced. After refilling with dry nitrogen of the flask for 1 hour, 2.28 g anhydrous methacryloyl chloride liquid was added dropwise into the solution at 0° C. for 3 hours. After reacting for 20 hours at room temperature under nitrogen, the solution was poured into 400 mL cold isopropyl alcohol to precipitate the product. The precipitate was filtered and dried in vacuo at room temperature for 24 hours to get 4.2 g (70.2% yield) Dex-MA product. Table 1 below summarizes the reagents and conditions for synthesizing Dex-MA, and the synthesis scheme is shown thereafter (Scheme 1).

TABLE 1

Summary of Synthesis Condition of Dextran Acrylate

| Reagent | Condition |
| --- | --- |
| Dextran (Mn = 16,000) | 4 g (0.025 mol repeat unit) |
| Methacryloyl chloride (Mr = 105.5) | 2.28 g (0.025 mol) |
| Pyridine (Mr = 79) | 2 g (0.025 mol) |
| Solvent (LiCl/DMAc: 5.0% w/v) | 40 mL |
| Reaction temperature | 0° C., Room temperature |
| Reaction time | 20 hours |
| Yield | 4.4 g (70.2.%) |

Scheme 1. Chemical scheme of synthesis of dextran acrylate (Dex-MA) precursor.

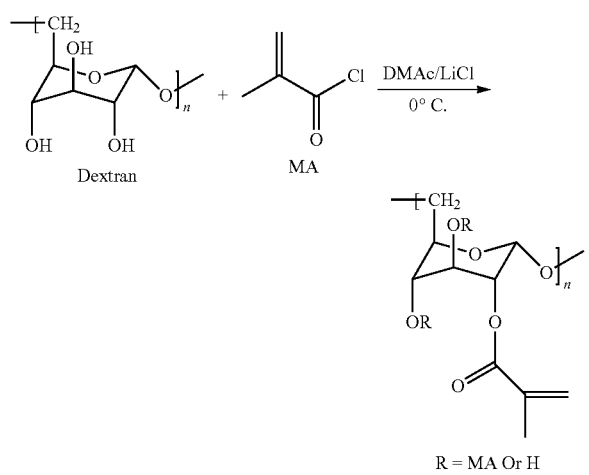

Step 2: Synthesis of arginine-lysine based PEA acrylate [2-Lys-4]-[2-Arg-4]-MA precursor The objective of this step is to synthesize AA-PEA precursors having photo-reactive vinyl groups for subsequent photo-reactions with Dex-MA precursor. To a flask, 2.182 g Arg-4-S(0.002 mol), 1.528 g Lys-4 (0.002 mol) and 1.552 g NA (0.004 mol) was added and dissolved in N,N-dimethylacetamide (DMAc). Then, 1.01 g triethylamine (NEt$_3$, 0.01 mol) was added to the flask and mixed, the reaction was carried at 70° C. for 12 hours and the product was obtained by precipitating in a large volume of ethyl acetate at a room temperature and purified by dissolved in methanol and precipitating in a large of ethyl acetate twice. The yield of the product, [2-Lys-4]-[2-Arg-4], is 70%.

1.122 g (0.002 mol) of the resultant product [2-Lys-4]-[2-Arg-4] was dissolved in DMAc in a three neck flask equipped with N$_2$ flow, and methacrylic anhydride 0.616 g (0.004 mol) and NEt$_3$ 0.505 g (0.005 mol) was added, the reaction was lasted for 8 hours at room temperature. The product was obtained by precipitating in ethyl acetate and dried in vacuo at room temperature overnight([2-Lys-4]-[2-Arg-4]-MA). The synthesis route and chemical structure was illustrated in Scheme 2 and 3 respectively.

Scheme 2. Synthesis scheme of [2-Lys-4]-[2-Arg-4] monomer.

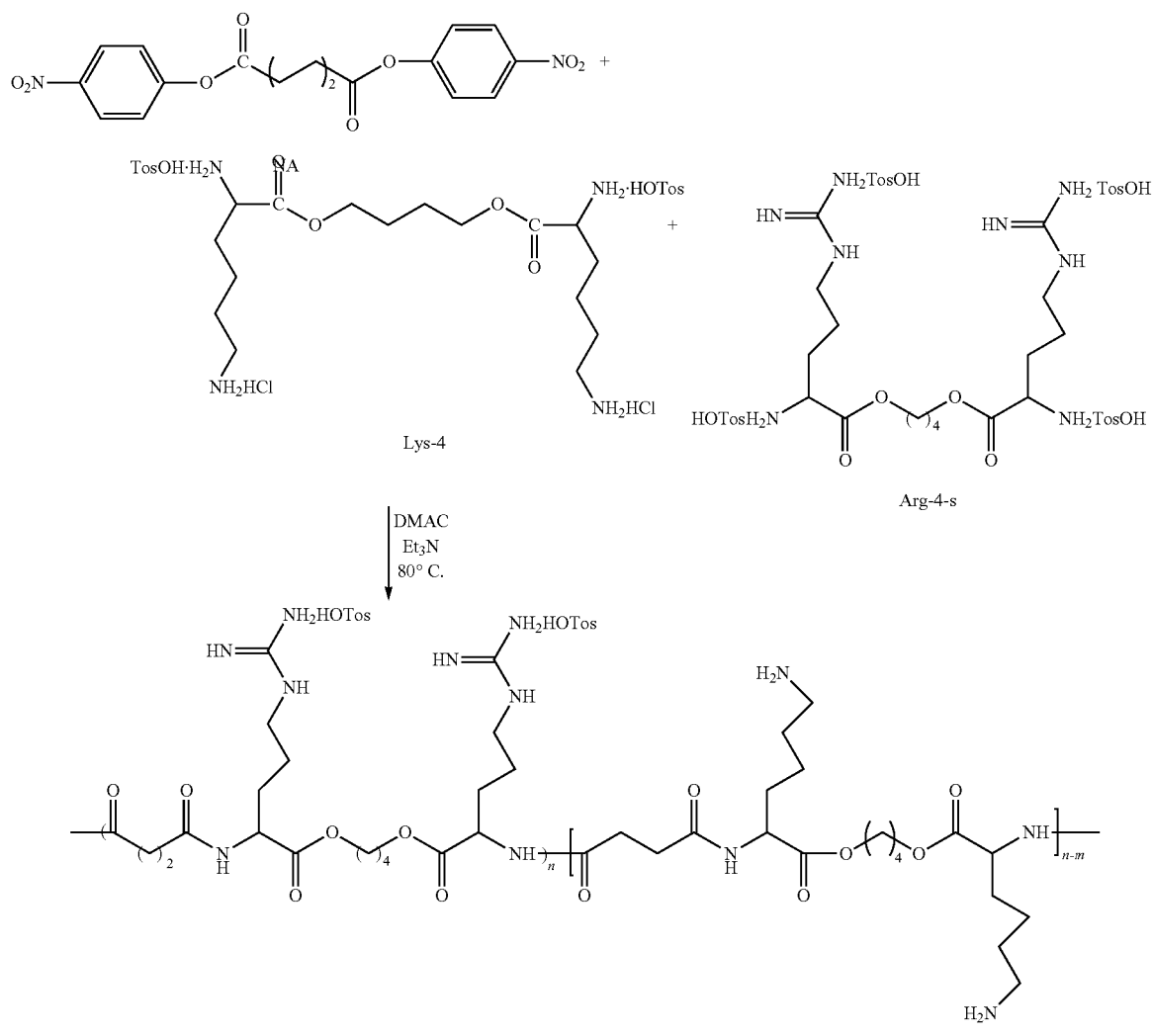

Scheme 3. Chemical scheme of synthesis of [2-Lys-4]-[2-Arg-4]-MA precursor.

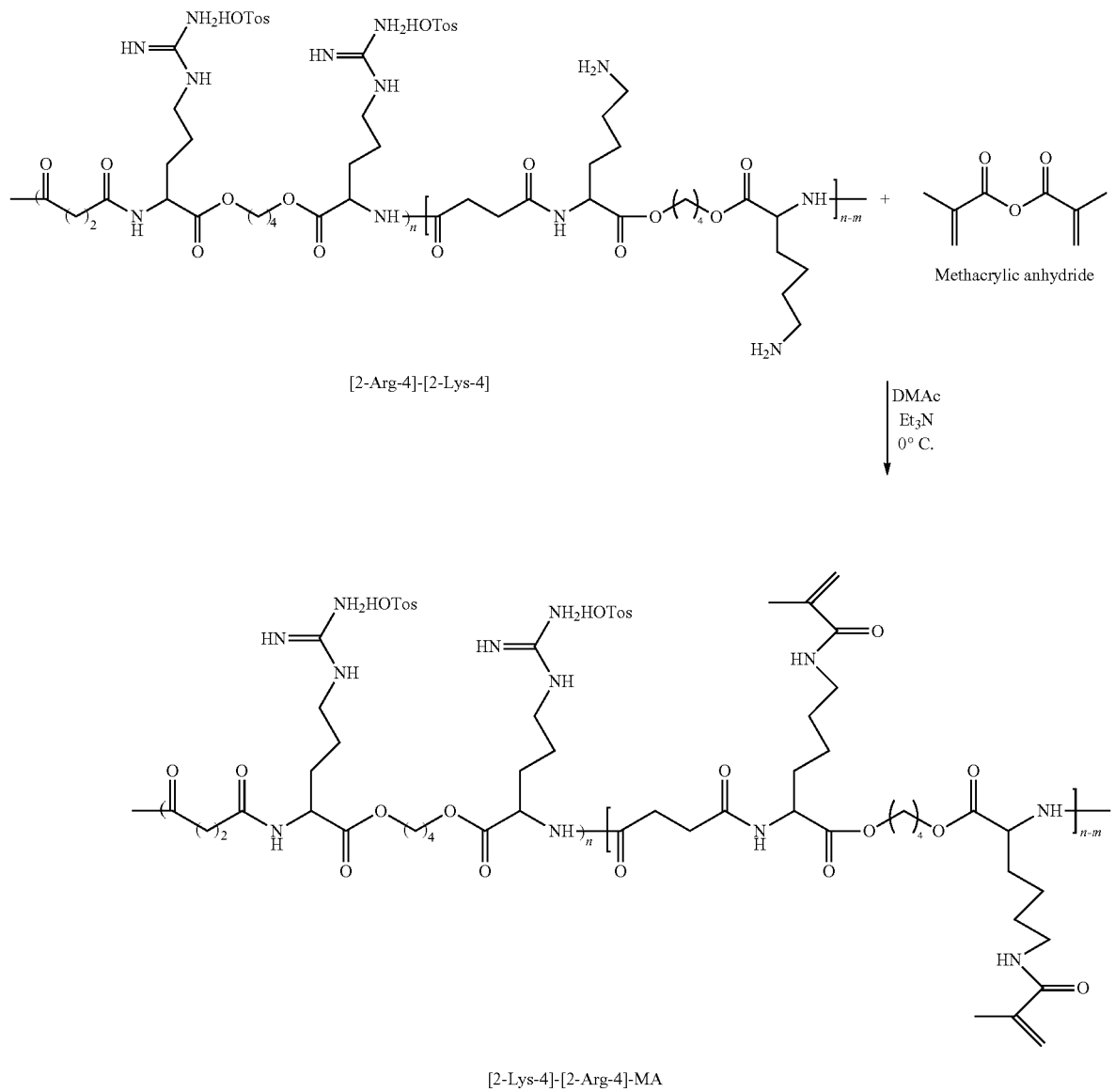

Step 3: Photo-fabrication of hybrid hydrogels of Dex-MA and arginine-lysine based PEA acrylate [2-Lys-4]-[2-Arg-4]-MA precursor. Typically, 100 mg Dextran-MA and 100 mg [2-Lys-4]-[2-Arg-4]-MA (at 1 to 1 precursors' weight feed ratio) were added into 2 mL deionized water and stirred for 20 min. Then 10 mg initiator (Ammonium persulfate, APS) was added into this solution and stirred for another 20 min. The solution was then poured into a 0.5 mL Teflon plate and exposed to 100 W, 365 nm UV-light for 20 minutes to get a pale yellow gel. The gel was then swelled in deionized water for 24 hours changed water periodically to remove residual photoinitiator as well as unreacted precursors. Table 2 below summarizes the photo-fabrication condition. The image of a typical such hybrid hydrogel along with a pure Dex-MA hydrogel are shown in FIG. 1.

TABLE 2

Reaction Conditions for Synthesis of the Dextran-MA and Dextran-MA/2-Arg-4]-[2-Lys-4]-MA PEA hybrid hydrogels.

| Materials | Gel0 | Gel1 | Gel2 | Gel3 |
|---|---|---|---|---|
| Dex-MA | 0.2 g | 0.1 g | 0.133 g | 0.16 g |
| [2-Arg-4]-[2-Lys-4]-MA | — | 0.1 g | 0.067 g | 0.04 g |
| APS | 10 mg | 10 mg | 10 mg | 10 mg |
| DI water | 2.0 g | 2.0 g | 2.0 g | 2.0 g |

Figure 2:
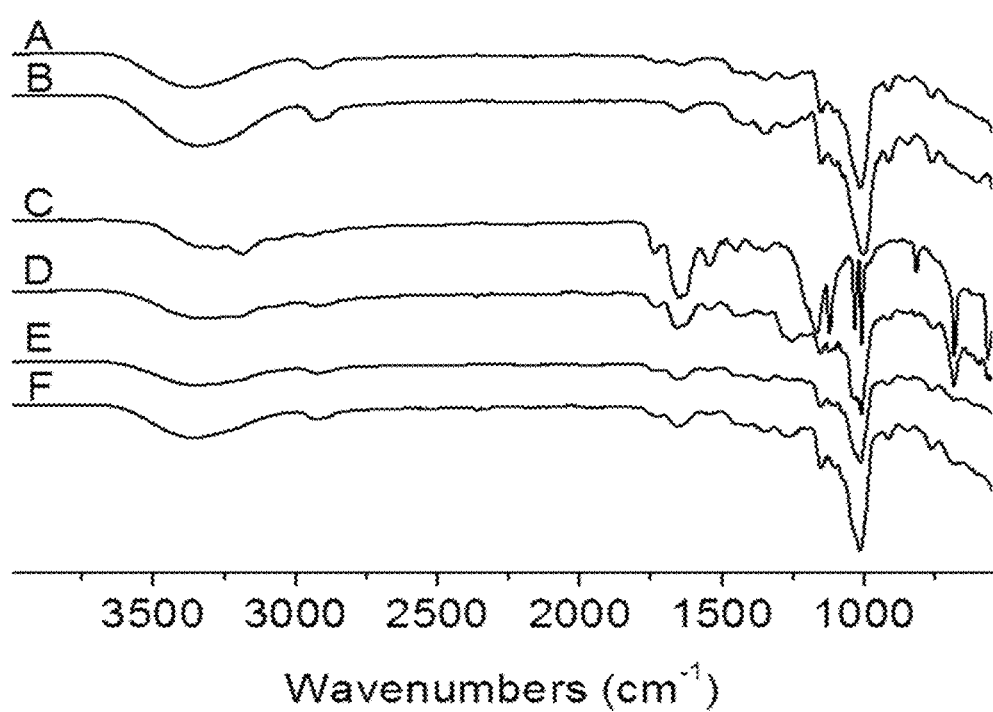
FIG. 2 show a representative FT-IR spectra of precursors and hybrid hydrogels. [A] [2-Lys-4]-[2-Arg-4]-MA; [B] Dextran-MA; [C—F] Dextran-MA/[2-Lys-4]-[2-Arg-4]-MA hybrid hydrogels. C-Gel0, D-Gel1, E-Gel2, F-Gel3. Refer to Table 2 for the type of hybrid hydrogels.
Figure 3:
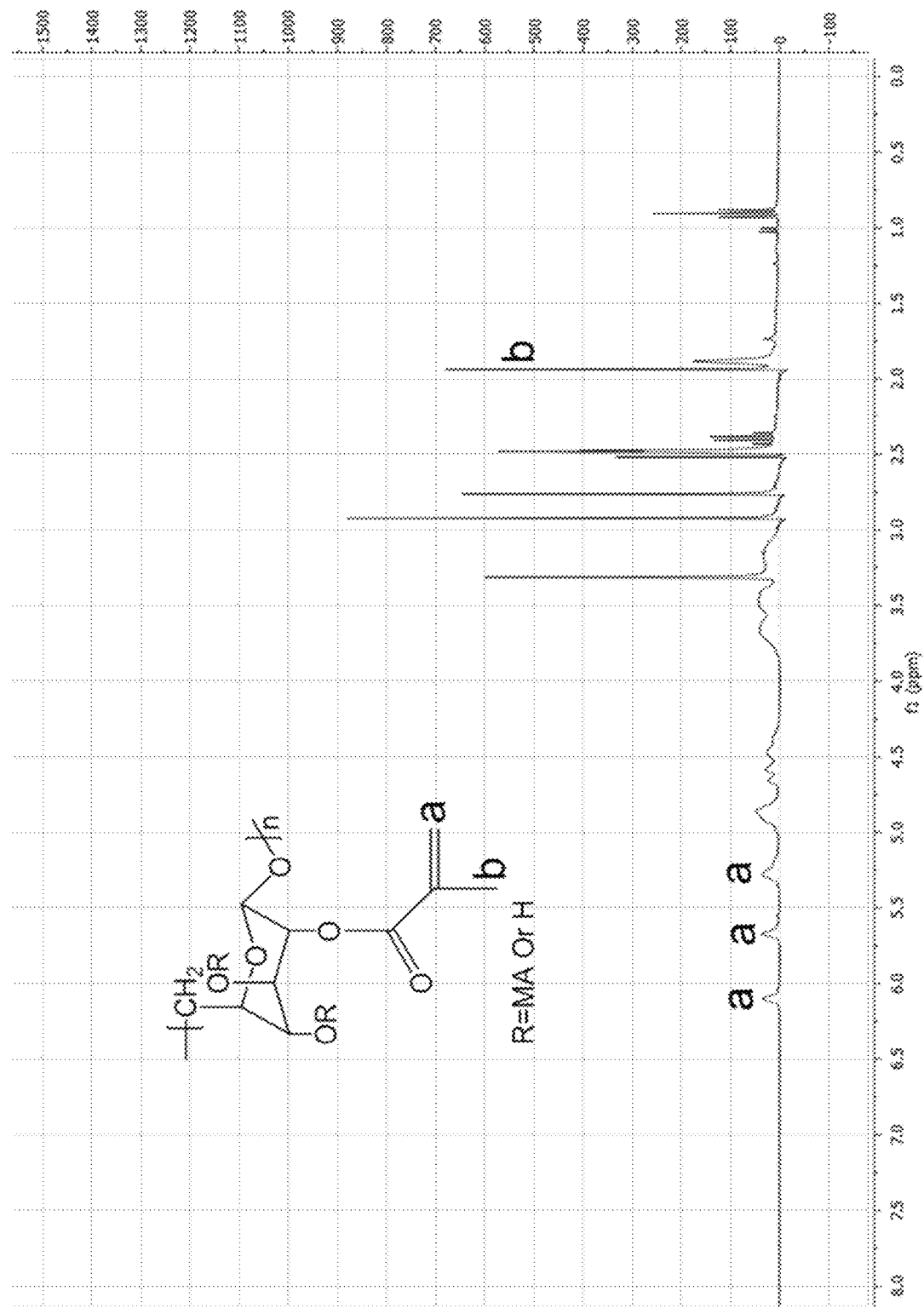
FIG. 3 shows a $^1$H NMR of Dextran-MA(solvent DMSO-d6).
Figure 4:
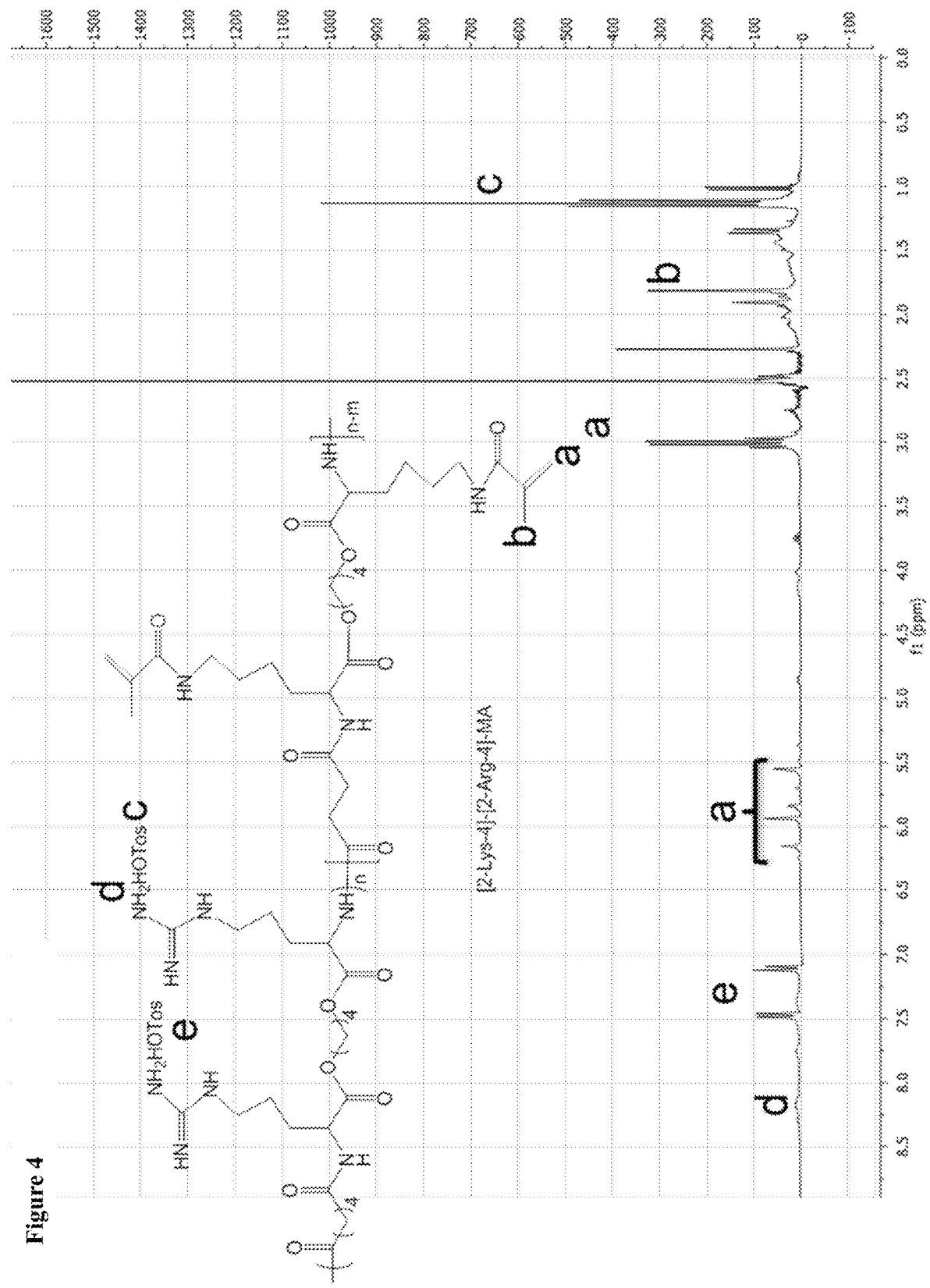
FIG. 4 shows a $^1$H NMR of [2-Lys-4]-[2-Arg-4]-MA (solvent DMSO-d6).
Figure 5:
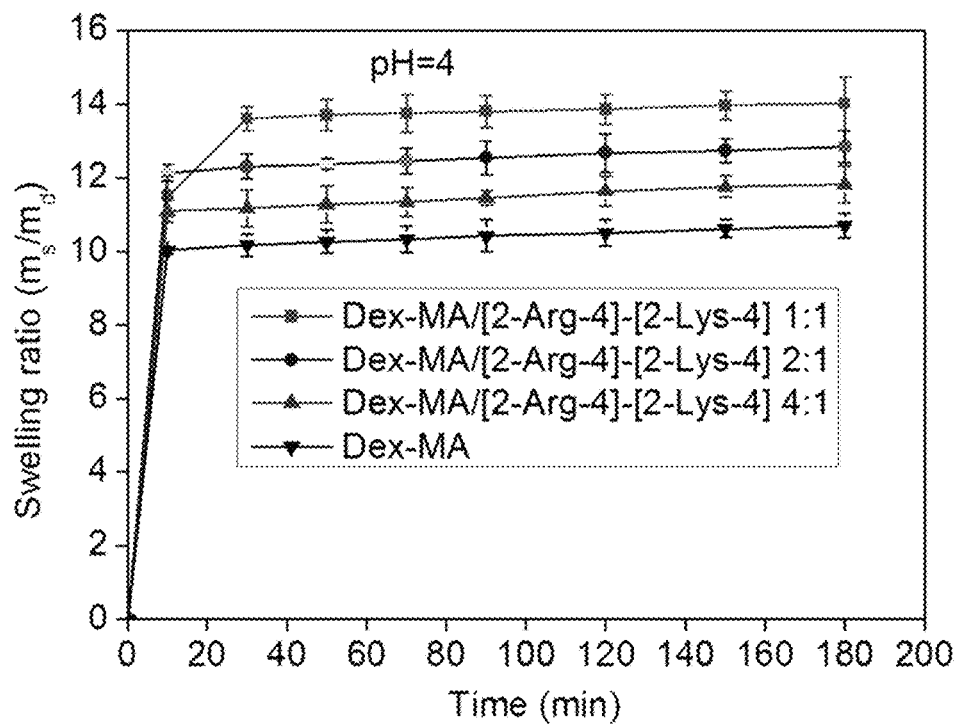
FIG. 5 shows representative swelling ratio of Dextran-MA and Dextran-MA/[2-Arg-4]-[2-Lys-4]-MA hybrid hydrogels in pH=4 (PBS, Ionic strength (I)=0.05) media.
Figure 6:
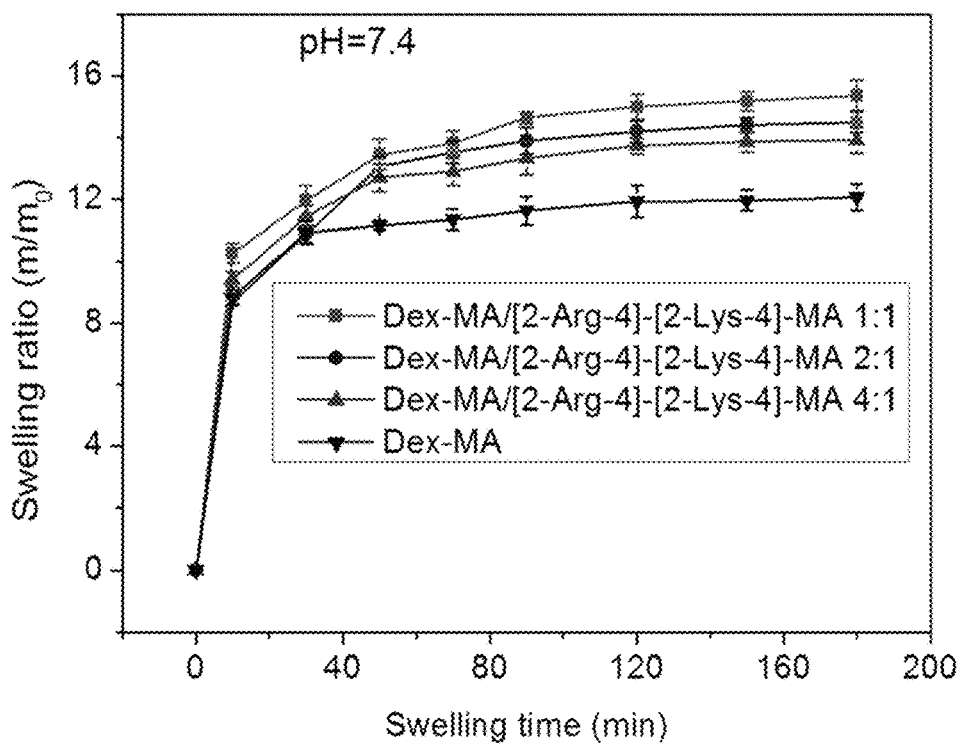
FIG. 6 shows representative swelling ratio of Dextran-MA and Dextran-MA/[2-Arg-4]-[2-Lys-4]-MA hybrid hydrogels in pH=7.4 (PBS, I=0.05) media.
Figure 7:
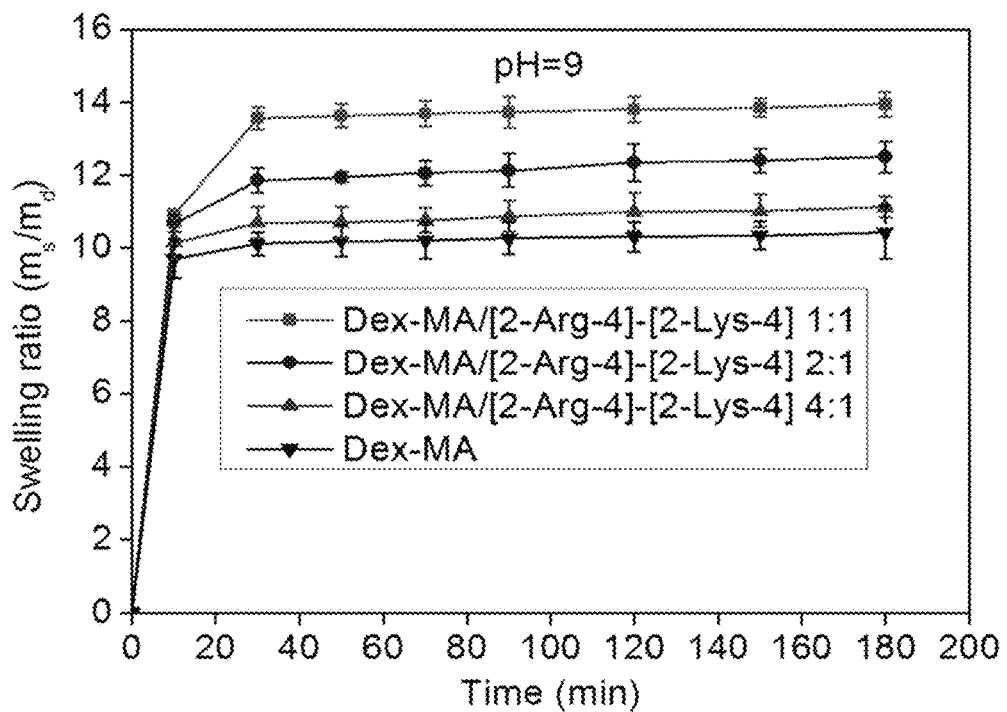
FIG. 7 shows representative swelling ratio of Dextran-MA and Dextran-MA/[2-Arg-4]-[2-Lys-4]-MA hybrid hydrogels in pH=9 (PBS, I=0.05) media.

Characterization of Hybrid Hydrogels: FT-IR spectra of monomers and hydrogels were recorded on a FTIR spectrometer (Perkin-Elmer Magna-IR560 Spectrometer) to characterize the chemical structures of Lys-4 monomer and its hydrogels. The samples were ground into pieces, compressed onto the KBr crystal, and FT-IR spectra were recorded in the wavenumbers range of 550-4,000 cm$^{-1}$, and is shown in FIG. 2. The $^1$H NMR spectra of monomers were recorded on a Mercury VX-300 spectrometer at 300 MHz (Varian, USA) by using DMSO-d6 as a solvent and TMS as an internal standard.

Mechanical property test: Compression moduli of the hybrid hydrogels were measured by dynamic mechanical analyzer (DMA Q800 V7.5 Build 127). Hydrogel samples were swollen in water for 24 hrs first before this testing. The maximum force applied was 0.1 N and ramp force was changed at the rate of 0.0100 N/min. The modulus, $E_c$, was calculated by the ISO 604 software at the strain value 0.05-0.25%. The compression moduli of the pure Dextran-MA hydrogel and Dextran-MA/[2-Arg-4]-[2-Lys-4]-MA hybrid hydrogels are shown in Table 3.

$$Ec=(\sigma_2-\sigma_1)/(\varepsilon_2-\varepsilon_1) \text{ where } \sigma: \text{ stress and } \varepsilon: \text{ strain}$$

TABLE 3

Compression moduli of pure Dextran-MA hydrogel and Dextran-MA/[2-Arg-4]-[2-Lys-4]-MA hybrid hydrogels

| Sample code | feed ratio(w/w)* | Compressive modulus (KPa) |
|---|---|---|
| Gel0 | pure Dextran-MA | 85 ± 2.1 |
| Gel1 | 1:1 | 26 ± 4.4 |
| Gel2 | 2:1 | 48 ± 5.1 |
| Gel3 | 4:1 | 62 ± 1.2 |

*Indicates the weight of Dextran-MA to [2-Arg-4]-[2-Lys-4]-MA precursors.

Swelling test: Swelling ratio of the hybrid hydrogels was measured in buffer media of different pHs (pH 4, pH 7.4, and pH 9) over time. Hydrogel samples were dried in a vacuum oven at 40° C. for 48 hours. The hydrogel samples were then weighed and soaked in 10 mL of buffer solutions at room temperature. The samples were removed, bloated dry and weighed at the predetermined immersion interval. The swelling ratio was calculated by the following equation.

$$S_w=(W_s-W_d)/W_d\times 100$$

$S_w$: Swelling ratio $W_s$: Weight of the hydrogel in a swollen state at time t $W_d$: Weight of the hydrogel in a dry state at time 0

The swelling data of the Dex-MA and Dex-MA/2-[2-Arg-4]-[2-Lys-4]-MA hybrid hydrogel are given in FIG. 2. All hydrogels showed an abrupt increase in swelling at the early stage, e.g., within the first 15 minutes; and they absorbed 10-14 fold of water of their weights. After this initial burst swelling, the swelling ratio of the pure Dex-MA and Dex-MA/2-[2-Arg-4]-[2-Lys-4]-MA hybrid hydrogels gradually increased until 1 hour. After 2 hours, most of the pure pure Dex-MA and Dex-MA/2-[2-Arg-4]-[2-Lys-4]-MA hybrid hydrogels reached to the equilibrium depending on the fabrication condition. The difference of swelling ratio was also observed in the different degree of substitution in Dex-MA. With more content 2-[2-Arg-4]-[2-Lys-4]-MA in the hydrogels, the swelling ratio is higher. The swelling ratio also varied with different pH, and increased with increasing pH.

Figure 8:
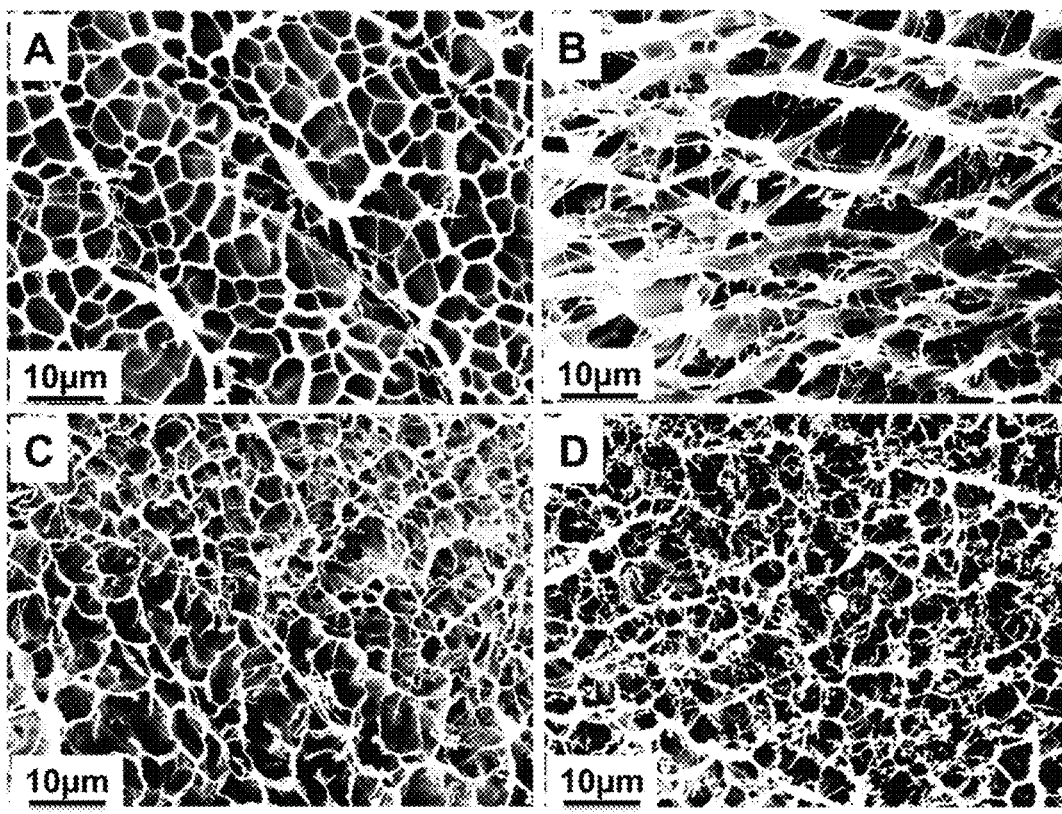
FIG. 8 shows representative SEM of Dex-MA(A) and Dex-MA/[2-Arg-4]-[2-Lys-4]-MA hybrid hydrogel, (B) Gel1; (C) Gel2; and (D) Gel3. See Table 3 for the composition of Gel1, 2 and 3.

Scanning electron microscopy. The interior and surface morphology of the Dextran-MA and Dextran-MA/[2-Arg-4]-[2-Lys-4]-MA hybrid hydrogels after swelling(see FIG. 8) and biodegradation in trypsin solution was measured by a scanning electron microscope (Leica Stereoscan, model no. 440). The swollen hydrogel samples were first freeze dried by cryofixation technique. To conserve the delicate inner structure of the hydrogel, the swollen hydrogel samples were frozen using the liquid nitrogen frozen and dried for 48 hours using a Virtis (Gardiner, N.Y.) freeze drier. The dried hydrogels were mounted onto aluminum stub and coated with gold/palladium (60%/40%) using sputter coater (Denton Vacuum Desk II). The samples were observed using SEM at 15 kV using an optimum depth mode.

The swollen pore structures of Dex-MA and Dex-MA/2-[2-Arg-4]-[2-Lys-4]-MA hybrid hydrogels having different amounts of Arginine based PEA. Smaller pore size was observed in all Dextran-MA/2-[2-Arg-4]-[2-Lys-4]-MA hybrid hydrogels. With the amount of 2-[2-Arg-4]-[2-Lys-4]-MA PEA increasing, the smaller average pore size was observed in hydrogels. The crosslinking reaction must occur in the presence of 2-[2-Arg-4]-[2-Lys-4]-MA PEA, as a result, the smaller pore structure was generated. Therefore, both the DS and the amount of 2-[2-Arg-4]-[2-Lys-4]-MA PEA content in the hydrogels affected the pore size of the resulting Dextran-MA pure hydrogel and Dextran-MA/2-[2-Arg-4]-[2-Lys-4]-MA hybrid hydrogels.

Biodegradation of the Dex-MA(A) and Dex-MA/[2-Arg-4]-[2-Lys-4]-MA hybrid hydrogel The biodegradation Dex-MA and Dex-MA/[2-Arg-4]-[2-Lys-4]-MA hybrid hydrogels were carried out in a small vial containing a small piece of known weight dry hydrogel sample (ca. 50 mg) and 10 mL of PBS buffer (pH 7.4, 0.1 M) with trypsin at the concentration of 0.1 mg/mL. A pure PBS buffer was used as a control. The vial was then incubated at 37° C. under a constant shaking rate (50 rpm). The incubation media were refreshed daily in order to maintain enzymatic activity. At predetermined immersion durations, hydrogel samples were removed from the incubation medium, washed gently with distilled water, and then lyophilized in vacuum with FreeZone Benchtop and Console Freeze Dry System (Model 7750000, LABCONCO Co., Kansas City, Mo.) at −48° C. for 72 h to a constant weight. The degree of biodegradation was estimated from the weight loss of the hydrogel based on the following equation:

$$W_l(\%) = \frac{W_o - W_t}{W_o} \times 100$$

Where W is the weight loss percent at immersion time t, $W_0$ was the original weight of the dried Lysine based hydrogel sample before immersion, and $W_1$ was the dry Dex-MA and Dex-MA/[2-Arg-4]-[2-Lys-4]-MA hybrid hydrogels sample weight after incubation for time t. The weight loss average of three specimens was recorded.

Example 2

This example shows methacrylate-based Chitosan derivatives and Their Hybrid Biomaterials. Non-limiting embodiments of the disclosure described herein are directed to a new and better pathway of synthesizing novel both aqueous and organo-soluble and enzymatic biodegradable and reactive chitosan precursors which could serve as the core starting biomaterials or precursors for developing downstream chitosan-based products and hybrids for a variety of biomedical applications.

In one example according to the disclosure, glycidyl methacrylate (GMA) is incorporated into both the hydroxyl and amino pendant groups of chitosan in the presence of p-toluene sulfonic acid monohydrate, 4-(N, N-dimethylamino) pyridine and DMSO solvent. By adjusting the molar feed ratio of glycidyl methacrylate to chitosan and reaction time, a wide range of degree of substitution (DS) of hydroxyl and amino pendant groups of chitosan by glycidyl methacrylate could be achieved (from 10 to 37 DS).

The main advantages of the newly disclosed synthetic strategy over others' published methods of modifying chitosan are: 1) much higher DS which permits the subsequent formulation into hydrogels that others couldn't achieve; 2) water and DMSO soluble and reactive chitosan precursors that others' couldn't achieve (others dissolve in either water or organic solvents, not both); 3) uses significantly lower amounts of GMA for achieving higher DS; and 4) lower reaction temperature 35 degrees C. vs. others's reported 60-70 degrees C.).

This newly developed GMA-chitosan core precursors have been used to integrated of polysaccharides with amino acid-based poly(ester amide)s.

A new method to synthesize water soluble, enzymatic biodegradable and photo-crosslinkable methacrylate-chitosan (GMA-Chitosan) was developed. Unsaturated methacrylate groups were introduced onto the hydroxyl and amine groups of chitosan. Methacrylate-chitosan was characterized by nuclear magnetic resonance (NMR), Fourier transform infrared spectroscopy (FTIR), carbon and nitrogen elemental analysis. The effects of feed ratio of reactants and reaction time on the incorporation of glycidyl methacrylate onto the chitosan were examined.

Optical transparent GMA-Chitosan hydrogel having high water contents was synthesized from this newly developed GMA-Chitosan aqueous precursor using UV-photo-crosslinking. The morphology of GMA-Chitosan hydrogel was examined by Scanning electron microscopy (SEM). The in vitro enzymatic biodegradation profile of GMA-Chitosan hydrogel by lysozyme was studied. The hydrophilicity, biodegradability, and photocrosslinking technique makes this GMA-Chitosan a promising material in drug delivery and tissue engineering applications.

Experimental: Materials: Chitosan (75-85% deacetylated) of molecular weight (MW) 50,000-190,000 and Bovine serum albumin (BSA) of molecular weight ~66,000 Da were purchased from Sigma Chemical Co., USA. Glycidyl methacrylate (GMA, 97%), 4-(N, N-dimethylamino) pyridine (DMAP, 99%), p-toluene sulfonic acid monohydrate, dimethyl sulfoxide (DMSO), sodium azide, lysozyme (from Chicken egg) were purchased from VWR Scientific (West Chester, Pa.). Ethyl acetate, acetone were purchased from Mallinckrodt incorporation (St. Louis, Mo.) and used without further purification. The DMSO, ethyl acetate, acetone were ACS grade. Micro BCA protein assay kit was purchased from Thermo Scientific Co., USA. Irgacure 2959 was donated by Ciba Specialty Chemicals Corp.

Synthesis of methacrylate chitosan (GMA-Chitosan): Chitosan in powder form (3.0 g, 0.0126 mol —$NH_2$) was dissolved in 200 mL DMSO with p-toluene sulfonic acid monohydrate (2.4 g, 0.0126 mol) at 50° C. for 3 hours under dry nitrogen atmosphere with magnetic stirring to form viscous clear light yellow color solution. 1 g DMAP was dissolved in 10 mL DMSO and was added dropwise into the chitosan solution in DMSO. After the total solution was cooled down 1 hour to room temperature in the ambient air, a calculated amount of glycidyl methacrylate (GMA, 2.4 g, 4.8 g and 7.2 g) was added. Different molar ratios of GMA and chitosan were used to adjust the DS of the final product. The reaction was continued at 35° C. for 48 hours with magnetic stirring. Samples (20 mL) were taken periodically from the reaction mixture to test the GMA degree of substitution of GMA-chitosan and the reaction was stopped by adding 0.5 g p-toluene sulfonic acid to neutralize the DMAP. Then, the sample solution was precipitated in 200 mL ethyl acetate and dried in vacuum oven at room temperature for 2 hours. The resulting crude gel-like GMA-Chitosan was cut into 1.5~2 mm cubic pieces and were completely washed by Soxhlet's extraction with acetone for 8 h to remove p-toluene sulfonic acid, DMAP and unreacted GMA and drying under vacuum. The degree of substitution (DS; the amount of methacrylate groups per 100 chitosan repeat unit) of GMA-Chitosan was determined by $^1$H NMR spectroscopy.

Preparation of GMA-Chitosan hydrogel: 10 mg Irgacure 2959 was dissolved in 100 μL deionized water and then added to a solution of GMA-Chitosan (300 mg, DS=28) in 4 mL deionized water. Every 400 μL of the mixed GMA-Chitosan aqueous solution with Irgacure 2959 was transferred onto a Teflon® mold with identical size (11 mm diameter, 6 mm depth) and then irradiated by a long wavelength (100 watts, 365 nm, mercury spot lamp, Blak-Ray®) UV light at room temperature about 30 min until disk-shaped hydrogel was obtained (11 mm diameter, 5 mm thickness). The resultant hydrogels were immerged into deionized water for 16 hours at room temperature to leach residues and reach the swelling equilibrium.

Characterization of GMA-Chitosan: Fourier Transform Infrared (FTIR): FTIR spectra of the grounded GMA-Chitosan powder samples were recorded on a PerkinElmer (Madison, Wis.) Nicolet Magna 560 FTIR spectrophotometer with Omnic software for data acquisition and analysis.

Proton nuclear magnetic resonance ($^1$H NMR): $^1$H NMR spectra were recorded on a Varian (Palo Alto, Calif.) Unity spectrophotometer at 400 MHz. The sample concentration in deuterium oxide was about 10% (w/v). All of the chemical shifts were reported in parts per million (ppm).

Carbon and nitrogen elemental analysis: Elemental analysis of GMA-Chitosan was performed on a Thermo Scientific ConFlo III elemental analyzer by stable isotope labratory of Cornell University. The calculated carbon and nitrogen contents are based on 80% deacetylated chitosan and the DS value of MA obtained from $^1$H-NMR.

Solubility: Solubility of GMA-Chitosan in different solvents, including water, tetrahydrofuran (THF), ethanol, chloroform, DMSO etc. were tested at room temperature under magnetic stirring.

Characterization of GMA-Chitosan hydrogel: Equilibrium swelling ratio (SR): dried GMA-Chitosan hydrogel disk samples were immersed in large amounts of deionized water at room temperature. After 16 hours, the swelling of the hydrogel sample reached an equilibrium, and the samples were taken out and carefully wiped with filter paper to remove the excess surface water before weighing. The equilibrium swelling was calculated according to the following formula:

$$SR(\%) = \frac{W_s - W_d}{W_d} \times 100,$$

where $W_d$ is the weight of dry hydrogels at time 0, and $W_s$ is the weight of swelling hydrogels at equilibrium.

Scanning electron microscope (SEM): SEM was employed to analyze the interior microstructure of GMA-Chitosan hydrogels. Cryofixation technique was used to observe the swollen hydrogel structure with minimal artifacts. Individual GMA-Chitosan hydrogel was immersed in deionized water at room temperature for 16 h to reach its swelling equilibrium. Then, the hydrogel was rapidly transferred into liquid nitrogen to freeze and retain the swollen structure. The sample was subsequent freeze-dried for 72 h in a Labconco (Kansas City, Mo.) Freezone 2.5 freeze drier under vacuum at −50° C. The freeze-dried hydrogel samples were then placed onto aluminum stubs and coated with gold for 30 s for SEM observation by Leica Microsystems GmbH (Wetzlar, Germany) 440.

Enzymatic degradation of GMA-Chitosan hydrogels: The enzymatic biodegradation of the disk shaped GMA-Chitosan hydrogels (12 mm diameter, 5 mm thickness) was evaluated by its weight loss at 37° C. in 15 mL 1 mg/mL lysozyme in 0.05 M pH 7.4 phosphate buffered saline (PBS). In the control group, the same GMA-Chitosan hydrogel samples were incubated in 15 mL PBS (pH 7.4, 0.05 M) at 37° C.

The course of enzymatic biodegradation of GMA-Chitosan hydrogels was followed gravimetrically until the loss of structural integrity of the hydrogels in a 1 mg/mL lysozyme PBS solution. Weight change of the hydrogels was measured at predetermined intervals. For each measurement, three replicated samples were used. Weight loss measurement: The weight of each dry GMA-Chitosan hydrogel was measured before immersion. At various immersion intervals, GMA-Chitosan samples were removed from lysozyme PBS solution or PBS solution of the control group and dried under vacuum at room temperature till the weight is constant. The weight loss was calculated according to the following equation: % Weight loss=$(W_0-W_1)/W_0 \times 100\%$, where $W_0$ was the average initial (t=0) dry weight of hydrogel, and $W_1$ was the dry weight of the hydrogel tested after t incubation time. Mean value of experimental data was calculated as the weight loss at time t with a standard deviation.

Results and discussion: Synthesis of photo-crosslinkable GMA-Chitosan: GMA has two reactive functional groups: a very reactive epoxy group and an acrylic group. The prior reported reactions of polysaccharide and GMA were performed in one of the two types of media: (1) mild basic aqueous environment (carbonate buffer, pH 11) or acidic aqueous environment (acetic acid solution); (2) DMSO. The aqueous medium led to GMA-substituted polysaccharides derivatized having low level of incorporation of acrylate groups, even though many fold excess of GMA was applied in the reactant mixture. The main reason is that the epoxy group of GMA is also able to react with water, yielding glyceryl acrylate which could not further react with polysaccharide. Moreover, the alkaline environment in water could also cause the hydrolysis of the ester bonds of GMA, before and after reaction with polysaccharide.

Scheme 4. Synthesis of glycidyl methacrylate chitosan

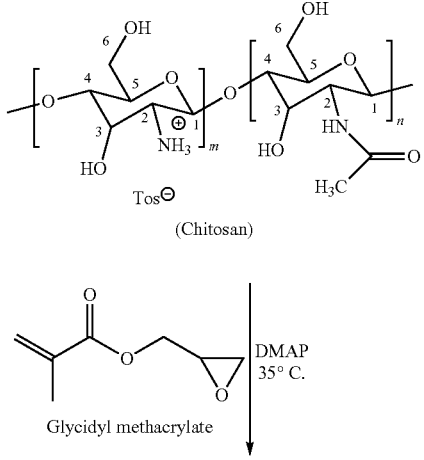

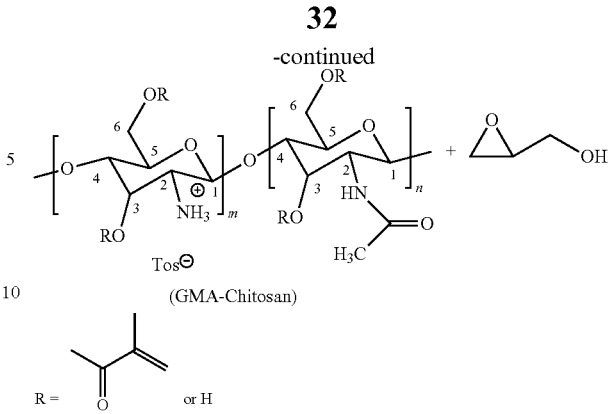

According to the study of GMA-Chitosan synthesis, DMAP was found to be the most effective alkaline catalyst which is able to achieve the same DS in a shorter reaction time. In the synthesis of GMA-chitosan, DMAP was used to catalyze the reaction of GMA and chitosan in DMSO at pH around 9. The role of DMAP is either to work as a Bronsted base to polarize the hydroxyl groups of chitosan or as a nucleophilic agent promoting the formation of the metacryloyl pyridinium salt.

The chitosan modification reaction is depicted in Scheme 4. At 35° C., GMA reacted with chitosan by a transesterification mechanism forming GMA-chitosan and glycidol by-product which can be removed in the Soxhlet's extraction purification process.

The reaction mechanism is consistent with most other studies about GMA-polysaccharide derivatives. The methacrylation of polysaccharides (dextran, galactomannan or even disaccharide sucrose) by GMA, the reaction did not take place at the epoxide ring. The only reaction mechanism between GMA and polysaccharide is transesterification, yielding polysaccharide-MA derivative with methacryloyl group attached to hydroxyl groups and glycidol.

Figure 11:
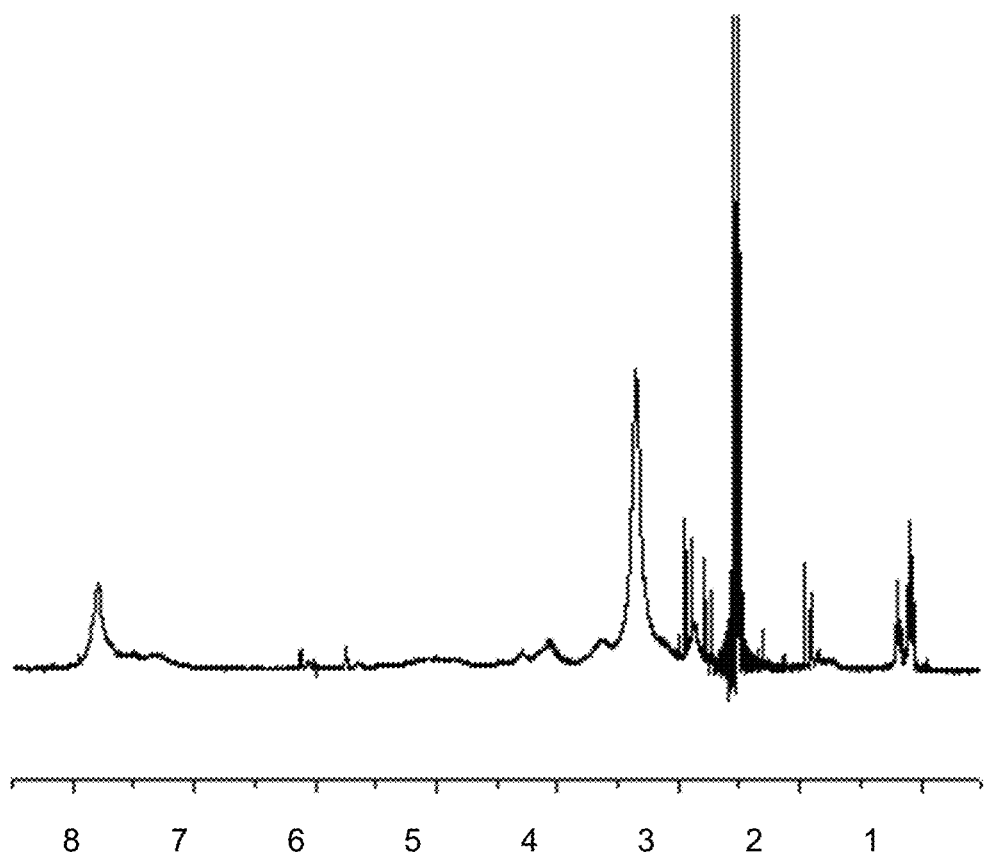
FIG. 11 shows a $^1$H-NMR spectrum of GMA-Chitosan.

$^1$H NMR analysis of GMA-Chitosan: The $^1$H-NMR spectrum of GMA-Chitosan in d-DMSO is shown in FIG. 11. Two small peaks at about 2.05 and 4.90 ppm existed because of the methyl group of residue N-alkylated repeat unit of chitosan. A singlet at 3.11 ppm was assigned to protons at position 2 of β-(1-4)-linked D-glucosamine units and N-acetyl-D-glucosamine units. And the multiples from 3.5 to 3.8 were attributed to protons at the position 3, 4, 5, 6 of β-(1-4)-linked D-glucosamine units and N-acetyl-D-glucosamine repeat units (FIG. 11). The signals from the protons at the double bond of methacrylate group are observed at 5.70 and 6.08 ppm. The DS was calculated from the peak area of the proton at position 2 of chitosan repeat unit (3.11 ppm) against that of the proton of methacrylate groups.

Figure 12:
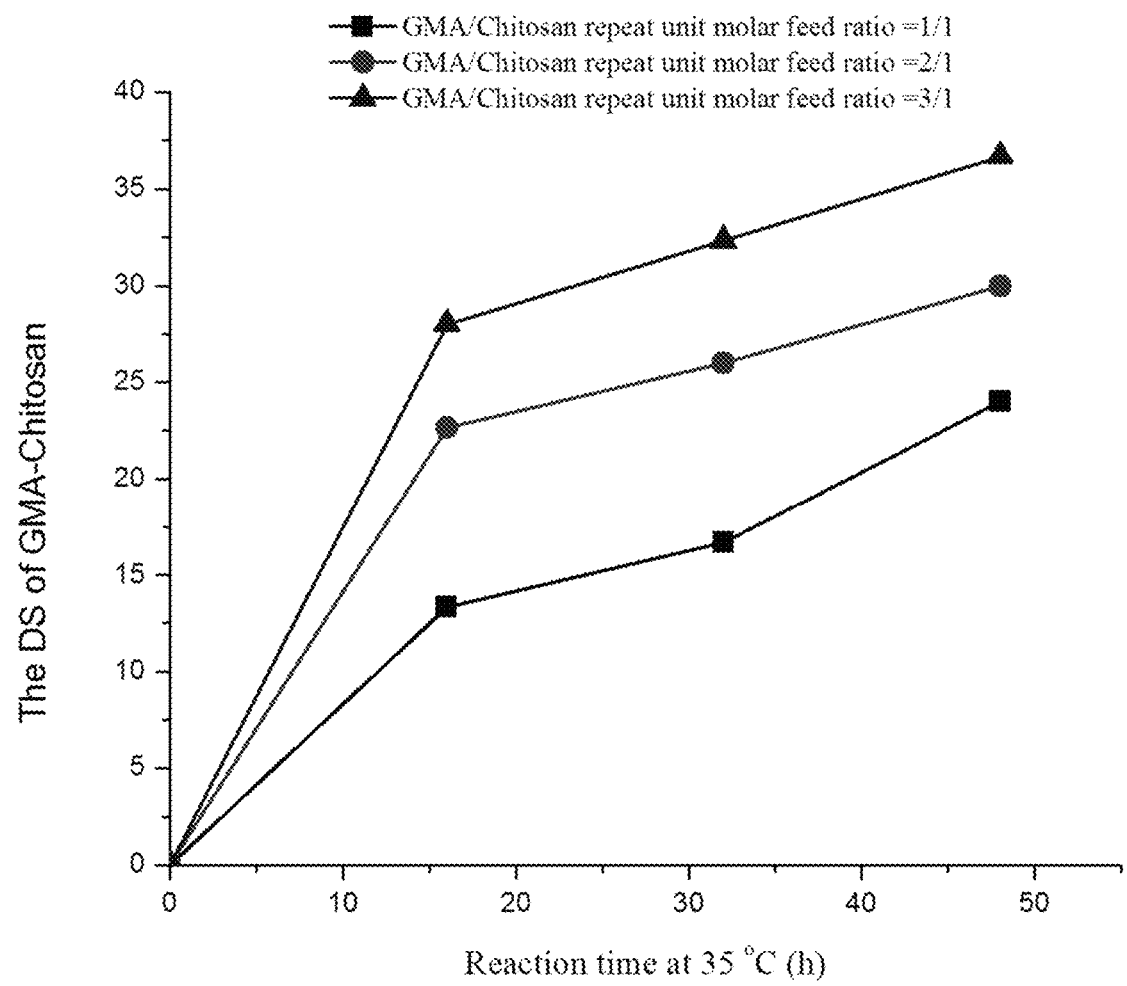
FIG. 12 shows an example of effect of molar feed ratio of GMA to chitosan glucosamine unit and reaction time on the degree of substitution of methacrylate group on GMA-Chitosan at 35° C.

FIG. 12 shows the relationship between the DS of methacrylate group on GMA-Chitosan (as determined by $^1$H-NMR data), the molar feed ratio of GMA to chitosan glucosamine unit, and reaction time. The high DS (>37) of GMA-Chitosan can be achieved and DS can also be controlled by tuning the reaction time and feed ratio. GMA-Chitosan (DS 37) synthesized at GMA/chitosan glucosamine unit feed ratio of 3/1 and 48 hours reaction time was chosen as the default GMA-Chitosan material for the subsequent fabrication of GMA-Chitosan hydrogel, because the higher DS of hydrophobic MA groups could lead to the reduction of water solubility of GMA-Chitosan as it is preferred to use aqueous medium for fabricating hydrogels to minimize adverse organic solvent effect in biomedical applications. The decreasing solubility in deionized water with the increasing MA degree of substitution was reported in the study of GMA-galactomannan. The incorporation of hydrophobic methacrylate side groups increased the hydrophobicity of GMA-polysaccharides.

GMA-Chitosan of DS 37 could be dissolve in deionized water to form 7 wt % solution which could be used as a hydrogel precursor.

The highest concentration of those GMA-Chitosan having DS>37 in deionized water is about 3-4 wt % which is not higher enough for fabricating robust GMA-Chitosan hydrogels by using photoinitiated polymerization technology. Compared with the DS data of GMA-Chitosan synthesized by previous methods in an acidic aqueous solution (DS 10.4), the proposed synthesis method in DMSO with alkaline catalyst DMAP could achieve GMA-Chitosan having much higher DS of MA. The DS of GMA-Chitosan, however, is still much lower than that of MA-dextran (~100) which was synthesized at the similar reaction condition, probably due to the hindrance caused by the high molecular weight of chitosan (50,000-190,000) and poorer solubility of chitosan in DMSO. The solubility of GMA-Chitosan at room temperature in many common solvents is shown in Table 4 GMA-Chitosan is only able to dissolve in water and DMSO.

TABLE 4

Solubility of GMA-Chitosan at room temperature

| | $H_2O$ | DMF | DMSO | DMAc | THF | Ethanol | Chloroform | Benzene |
|---|---|---|---|---|---|---|---|---|
| Chitosan | – | – | – | – | – | – | – | – |
| GMA-Chitosan (DS 37) | + | – | + | – | – | – | – | – |

+, soluble (solubility >=5 mg/ml);
– insoluble

Figure 13:
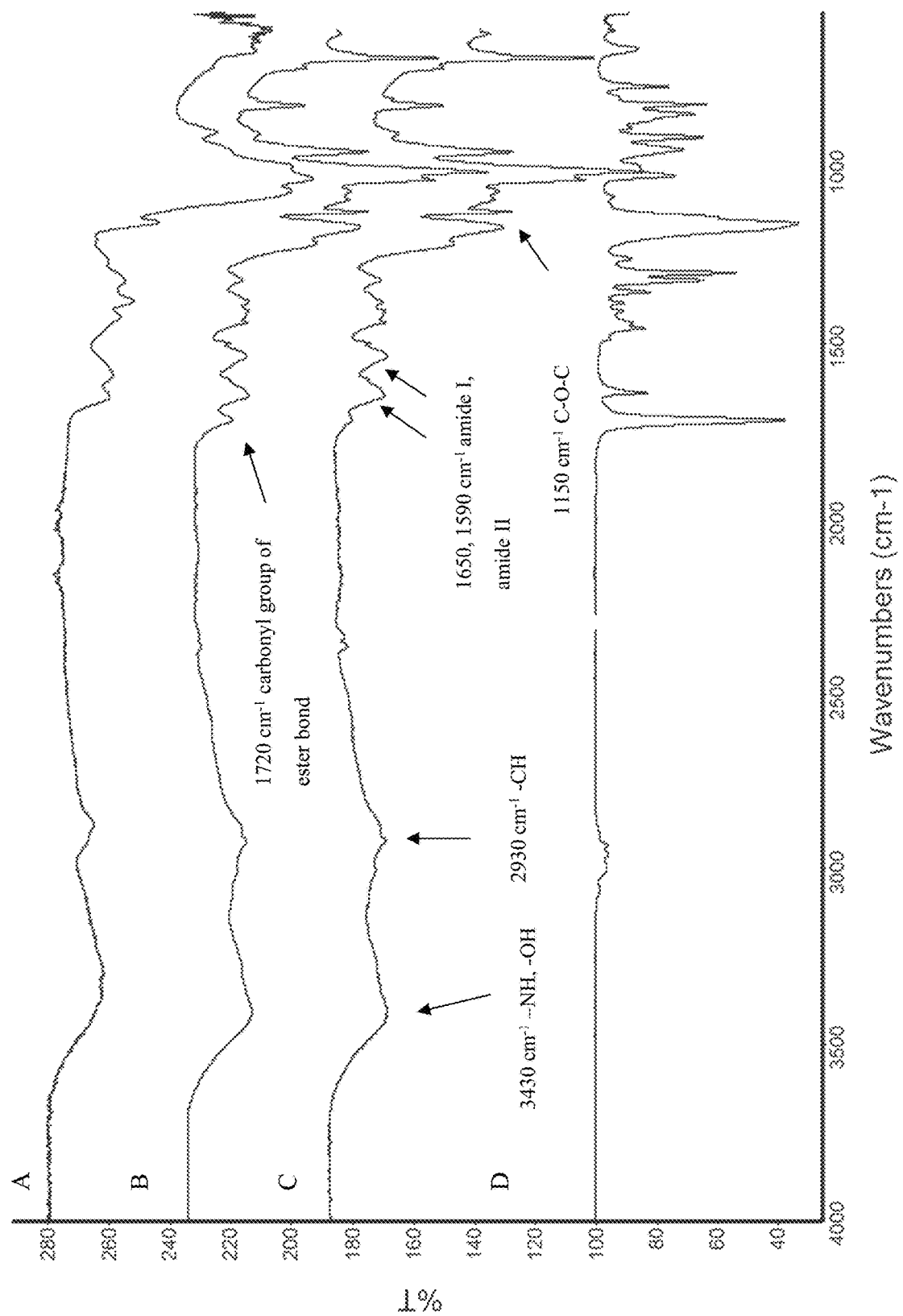
FIG. 13 shows a FT-IR of GMA-Chitosan which are synthesized from different GMA/Chitosan repeat unit molar feed ratio. (A) Chitosan; (B) GMA-Chitosan (DS 37); (C) GMA-Chitosan (DS 28); (D) Glycidyl methacrylate.

FT-IR analysis of GMA-Chitosan: FIG. 13 shows the spectra of chitosan (A) and GMA-Chitosan of two different DS (DS 37 in B, DS 28 in C) and GMA (D). A broad band around 3430 $cm^{-1}$ was attributed to —NH and —OH stretching vibration and another weak band at 2930 $cm^{-1}$ was from —CH stretching. Both chitosan and GMA-Chitosan FT-IR spectra present these characters (FIG. 13 B, C). The characteristic peaks at 1650, 1590 $cm^{-1}$ were assigned to the amide I, amide II absorption bands of chitosan. The absorption band at 1150 $cm^{-1}$ was assigned to the asymmetric stretching of the C—O—C of chitosan (FIG. 13 A, B, C). In the spectra of GMA and GMA-Chitosan, the absorptions at 1720 $cm^{-1}$ and at 815 $cm^{-1}$ are indicative of the carbonyl group and the double bond of methacrylate group, respectively, which were not presented on the spectra of chitosan (FIG. 13 A).

Carbon and nitrogen elemental analysis of GMA-Chitosan: The MA group doesn't contain nitrogen element, the nitrogen content of GMA-Chitosan would obviously be decreased from chitosan after the substitution reaction. Due to the difference of the carbon content of GMA and chitosan, the carbon content of GMA-Chitosan slightly increased while the nitrogen content slightly decreased when DS of GMA to chitosan increased (shown in Table 5). The data from elemental analysis was consistent with the composition calculated.

TABLE 5

C % or N % of chitosan and GMA-Chitosan

| Sample | Carbon content (%) | Nitrogen content (%) | Calculated carbon content (%) | Calculated nitrogen content (%) |
|---|---|---|---|---|
| Chitosan | 40.3 | 7.5 | 40.9 | 7.5 |
| GMA-Chitosan (DS 13) | 42.1 | 6.8 | 42.6 | 7.05 |
| GMA-Chitosan (DS 28) | 43.6 | 6.4 | 44.3 | 6.6 |
| GMA-Chitosan (DS 37) | 44.4 | 6.1 | 45.3 | 6.4 |

Figure 14:
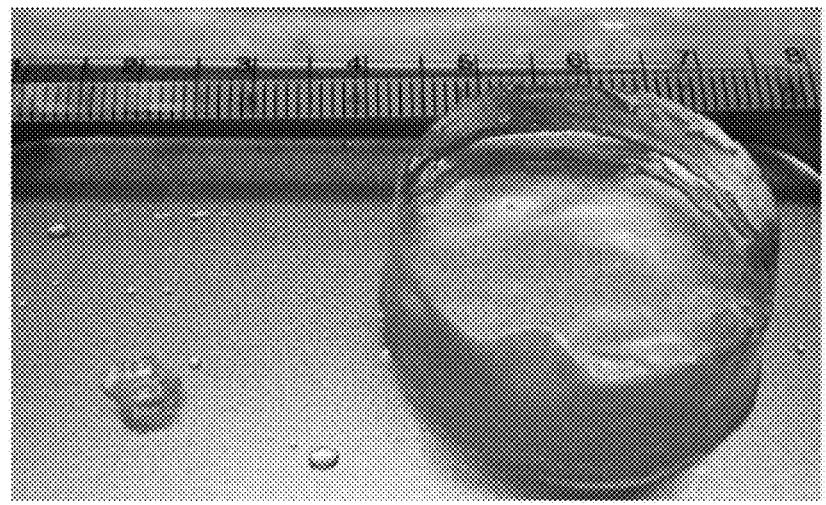
FIG. 14 shows representative GMA-Chitosan (DS 37) hydrogel. (Dried GMA-Chitosan hydrogel (DS 37) on left, swollen GMA-Chitosan in water after 16 hours on right, the swell ratio of GMA-Chitosan (DS 37) hydrogel is about 6,768±456%).

Photo-crosslinking of GMA-Chitosan hydrogel: GMA-Chitosan hydrogel fabrication was performed by photo-initiated crosslinking of GMA-Chitosan (DS 37) with Irgacure 2959 photo-initiator in an aqueous solution in a Teflon® mold at room temperature under 30 min UV radiation. Disk shaped transparent GMA-Chitosan hydrogel with clear edge could be formed by using 7 wt % GMA-Chitosan aqueous solution as hydrogel precursor. These freshly made disc-shaped GMA-Chitosan hydrogels (12 mm diameters, 5 mm thickness) were dehydrated at room temperature in air for 2 days, their size was reduced to about 5 mm diameter and 1.5~2 mm thickness (left gel sample in FIG. 14). The equilibrium swelling ratio of GMA-Chitosan hydrogel (6,768±456%) was obtained using dehydrated hydrogels immersed in deionized water for at least 16 h till they reach swelling equilibrium. GMA-Chitosan hydrogel could absorb more than 60 folds of its own weight of water which is probably due to the loosely crosslinked polymer network and good hydrophilicity of GMA-Chitosan.

The equilibrium water content of MA-dextran hybrid hydrogel reported is about 42.6% which is much lower than GMA-Chitosan. The possible reasons are attributed to hydrophilicity of the biopolymers and their DS. GMA-Chitosan polymer chain is more hydrophilic that of MA-dextran after the free amine group on each D-glucosamine forms salt with p-toluene sulfonic acid which could be protonated in water. In addition, MA-dextran usually has much higher DS of MA than GMA-Chitosan, suggesting that MA-dextran should have a much tighter network structure than GMA-Chitosan, i.e., lower swelling.

Morphology of GMA-Chitosan hydrogel: The porous interior morphology of a swollen GMA-Chitosan hydrogel was shown in FIG. 16. GMA-Chitosan (DS 37) hydrogel shows irregular shaped pores with average pore diameter 25 μm. This GMA-Chitosan (DS 37) interior structure is similar to the hydrogel made from low DS MA-dextran which has pore size ranging from 17 μm-50 μm diameter.

Enzymatic biodegradation of GMA-Chitosan hydrogel: The biodegradation of GMA-Chitosan hydrogel without lysozyme presence is mainly followed a bulk erosion model: the degradation happened both at the surface and interior. During the first 4 days immersion in PBS, GMA-Chitosan hydrogels continuously lose their weight and mechanical strength, but their their gross structure remain intact. In the presence of lysozyme mediu, however, GMA-Chitosan hydrogels became visibly smaller in size and lose their structure integrity much faster than in the PBS medium. The enzymatic degradation behaviors of GMA-Chitosan hydrogel in the presence and in the absence of lysozyme were investigated in PBS. For example, the weight loss of GMA-Chitosan hydrogel in the presence of 1 mg/ml lysozyme is about 42% after 14 days degradation, whereas the same hydrogel in PBS control group showed only about 34% weight loss at the same time. After 5 days immersion, the weight losses of GMA-Chitosan hydrogels in the presence of lysozyme were 5%~10% greater than the same hydrogels samples in the absence of lysozyme, i.e., PBS only.

The degradation of GMA-Chitosan hydrogel can be attributed to two reasons: the ester bond of methacrylate group is degraded by hydrolysis, and lysozyme is able to cleave GMA-Chitosan hydrogel network structure at the β (1, 4) linked glucosamine unit and N-acetyl-D-glucosamine unit. Because GMA-Chitosan has good hydrophilicity and is able to absorb large amount of water into the hydrogel network structure, the hydrolysis of methacrylate linkage is also happened at the interior of hydrogel. Because lysozyme's MW is higher than 14 k Da, it may be difficult to diffuse into the deep interior of the GMA-Chitosan hydrogel network during the early stage of immersion. So, the enzymatic biodegradation firstly happened at the surface and near the surface t of the hydrogels. This biodegradation mechanism helped GMA-Chitosan hydrogel achieved faster degradation rate than those in the absence of lysozyme.

Figure 15:
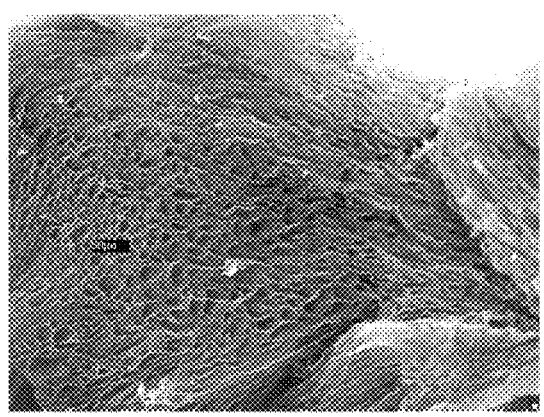
FIG. 15 shows SEM images of swollen GMA-Chitosan (DS 37) hydrogel in deionized water (A) 200×; (B) 1000×
Figure 15:
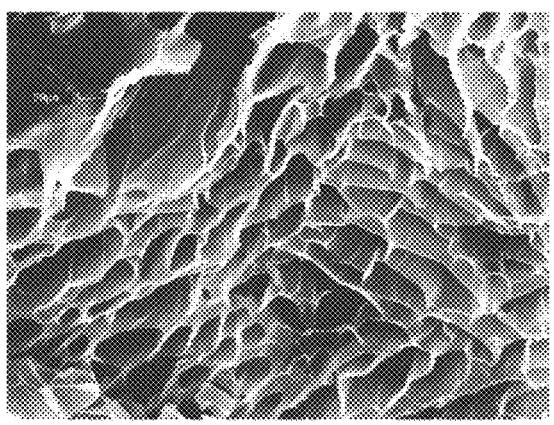
Figure 16:
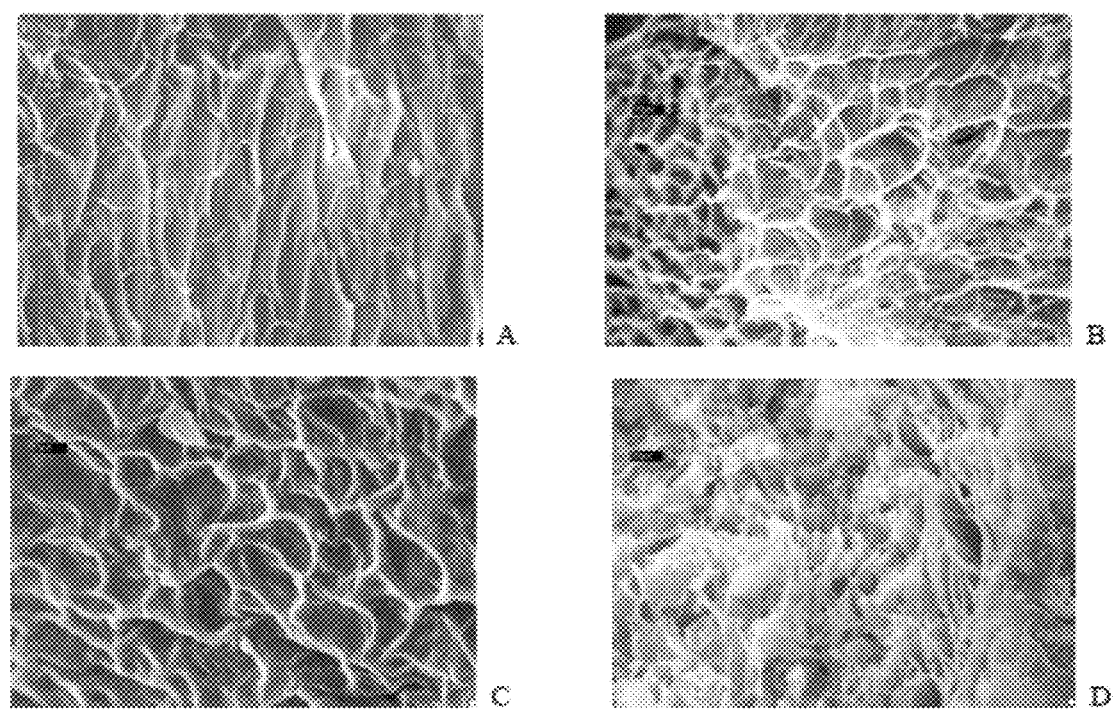
FIG. 16 shows representative SEM of GMA-Chitosan in enzymatic degradation. (A) after 2 days degradation in PBS; (B) after 2 days enzymatic degradation in 1 mg/ml lysozyme; (C) after 14 days degradation in PBS; (D) after 14 days enzymatic degradation in 1 mg/ml lysozyme.

FIG. 16 presents the change in the morphological structure of the GMA-Chitosan upon degradation observed by SEM. When compared with the undegraded GMA-Chitosan morphology (16 hrs in PBS medium) shown in FIG. 15, the morphological structure of GMA-Chitosan hydrogels after 2 days enzymatic biodegradation (FIG. 16 B) show less distinctive high profile pores as the control (FIG. 15B), and the distinctive pore structure of the GMA-Chitosan hydrogels disappeared via the collapsing and merging of pores after 14 days in lysozyme medium (FIG. 16 D).

On the contrary, in the presence of pure PBS, the porous structure of GMA-Chitosan hydrogel was largely destroyed by a pure hydrolysis mechanism (FIG. 16 A, C). The possible reason is the degradation product of GMA-Chitosan at the end of 14 days could still be high molecular weight chitosan derivative because hydrolytic scissions only cleave the ester bonds of methacrylate groups that act as a cross-linker to tie chitosan macromolecules together, i.e., no chitosan backbone fragmentation in a pure PBS environment. The high molecular weight degradation product aggregated on the pore walls and eventually filled up the pores (FIG. 16 C). Whereas the enzymatic biodegradation produces oligosaccharides from chitosan backbone with much lower MW than chitosan. These low MW degradation products can be easily escaped from GMA-Chitosan hydrogel through diffusion. So, GMA-Chitosan can still keep the porous structure in the process of enzymatic biodegradation. Compared with the degradation data of PEG crosslinked chitosan hydrogel films, GMA-Chitosan hydrogel can achieve the same level weight loss in less than half of the degradation time of PEG crosslinked chitosan in the presence or absence of the same concentration of lysozyme. This is because the GMA-Chitosan may have ester bond linkages of methacrylate group that is lacking in the PEG-crosslinked chitosan.

Figure 17:
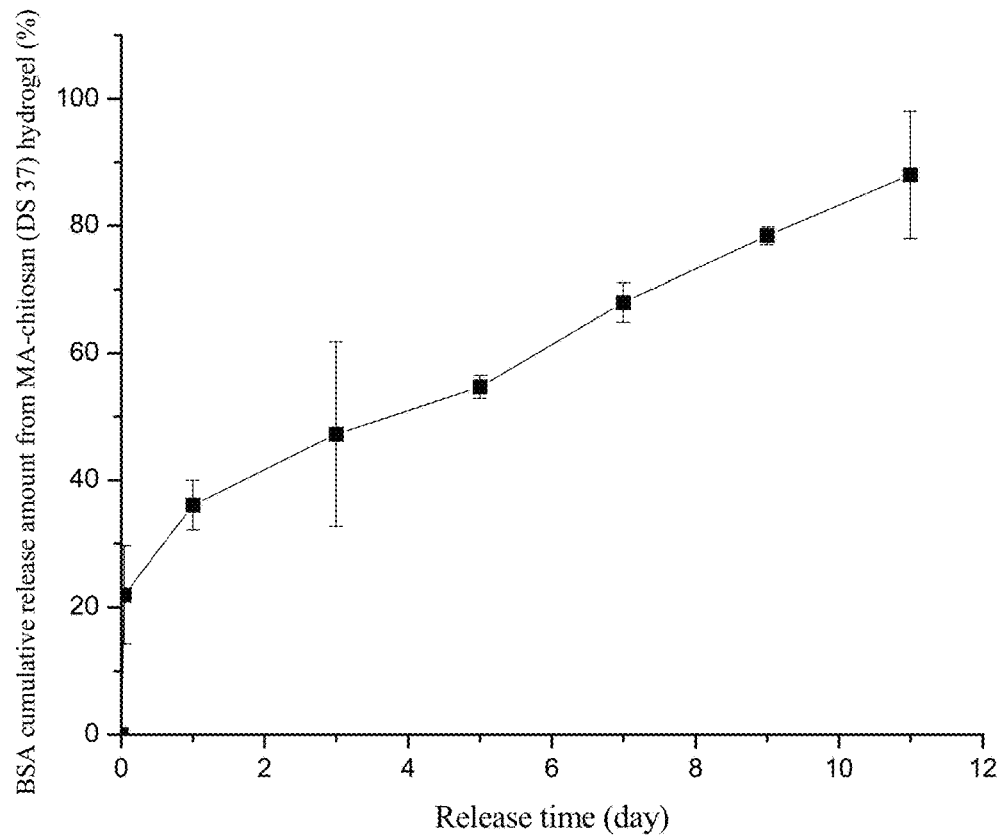
FIG. 17 shows representative BSA release of GMA-Chitosan (DS 37) hydrogel in PBS (pH 7.4) at 37° C.

BSA release from GMA-Chitosan hydrogel: GMA-Chitosan hydrogel has been evaluated as the matrix for controlled release of BSA protein. Release profile of BSA (MW~66,000) from GMA-Chitosan as a function of incubation time in PBS media is shown in FIG. 17. At the end of 11 days, more than 80% of BSA was released from GMA-Chitosan hydrogels at 37° C. Burst release of BSA happened in the first hour of incubation which is due to dissolution of BSA on the MA-hydrogel surface. Compared with other synthesized UV-crosslinked polymer hydrogels, such as poly(ethylene glycol) diacrylate hydrogels, the BSA release rate from GMA-Chitosan is much faster due to the mesh size of GMA-Chitosan hydrogel is bigger. BSA can more easily diffuse out of the hydrogel.

Figure 18:
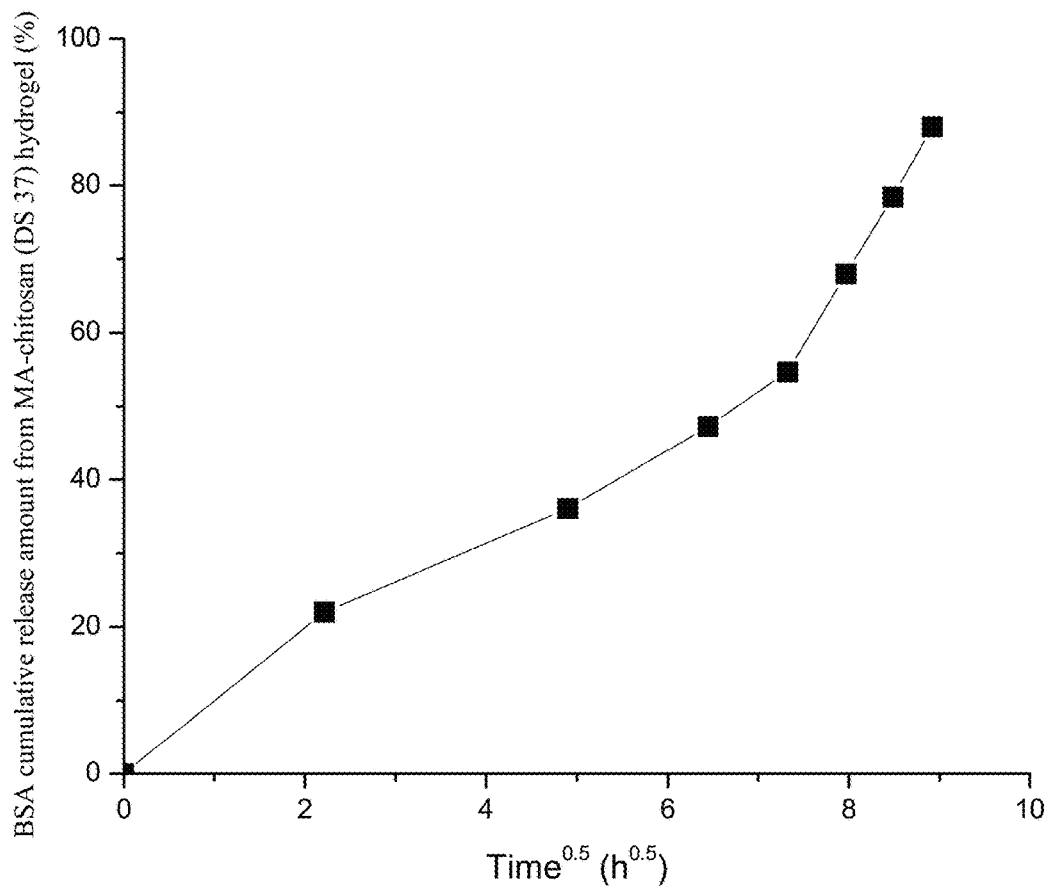
FIG. 18 shows square-root of time relationship for release of BSA from GMA-Chitosan in PBS (pH 7.4) buffer at 37° C.
Figure 19:
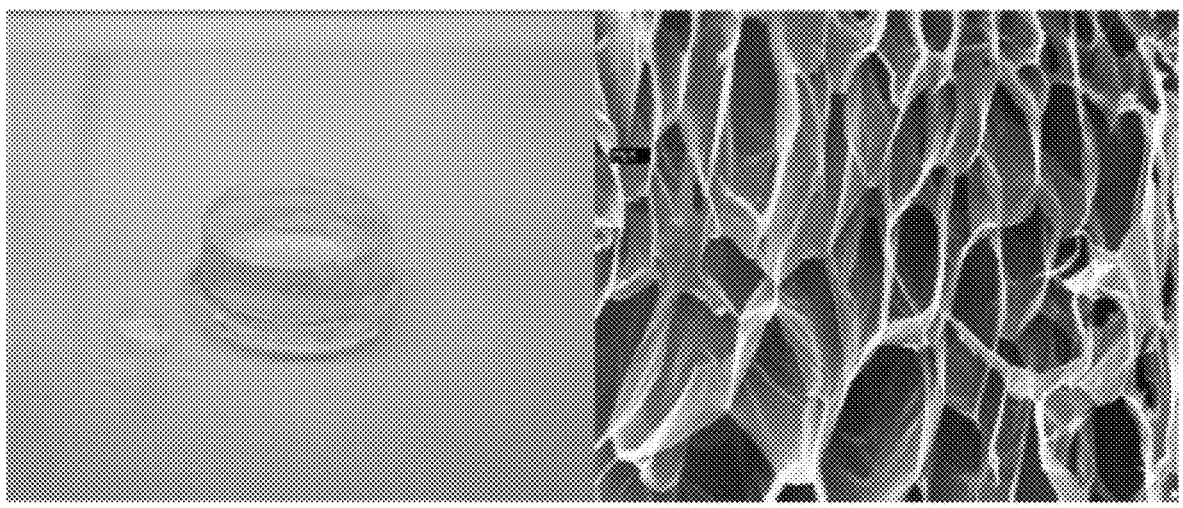
FIG. 19 shows representative, (Left) optical image of a hybrid hydrogel of GMA-Chitosan and 2-UArg-4 PEA at 2/1 weight feed ratio, and (right) SEM image of the same hybrid hydrogel.
Figure 20:
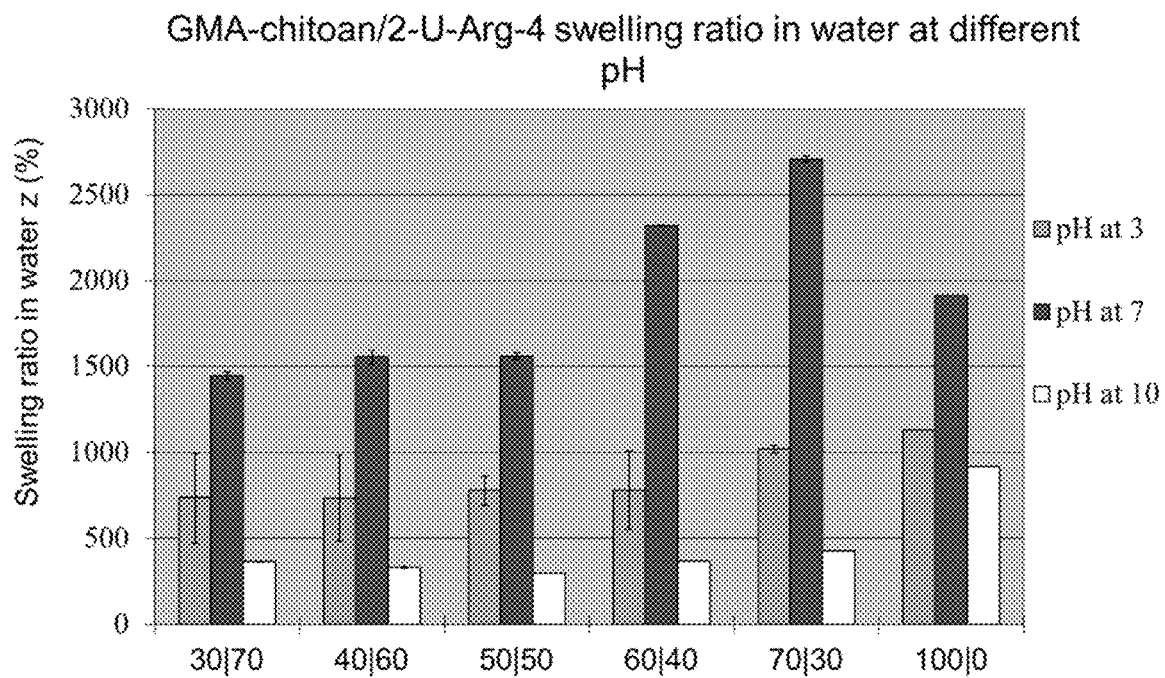
FIG. 20 shows representative GMA-chitoan/2-U-Arg-4=50/50 hybrid hydrogel swelling ratio in water at different pH.
Figure 21:
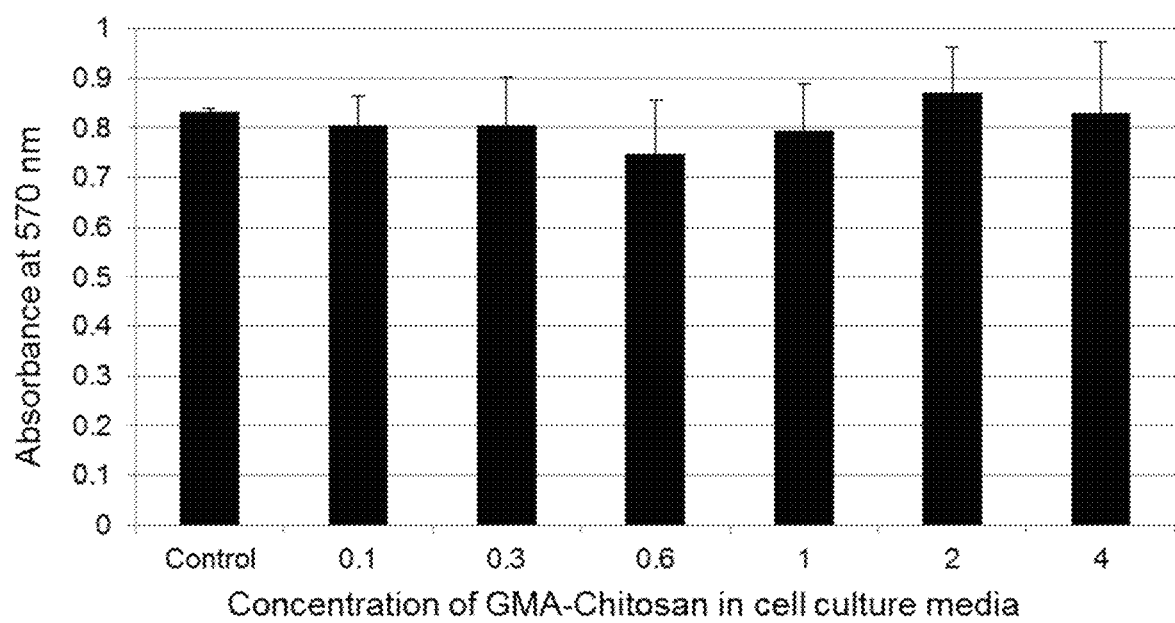
FIG. 21 shows representative cytotoxicity (porcine aortic valve smooth muscle cell) of GMA-chitosan hydrogel precursor.
Figure 22:
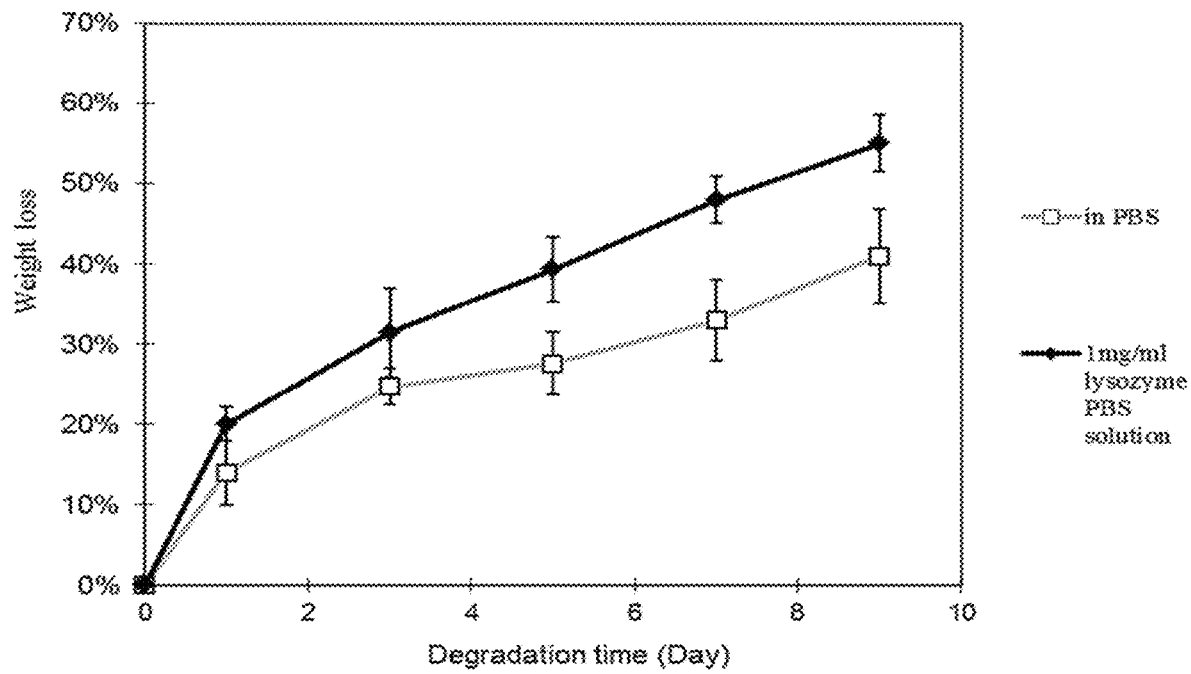
FIG. 22 shows representative enzymatic degradation of GMA-chitosan/2-U-arginine-4=67/33 in 1 mg/mL lysozyme and in PBS buffer solution (The degree of substitution of GMA-chitosan is 37).
Figure 23:
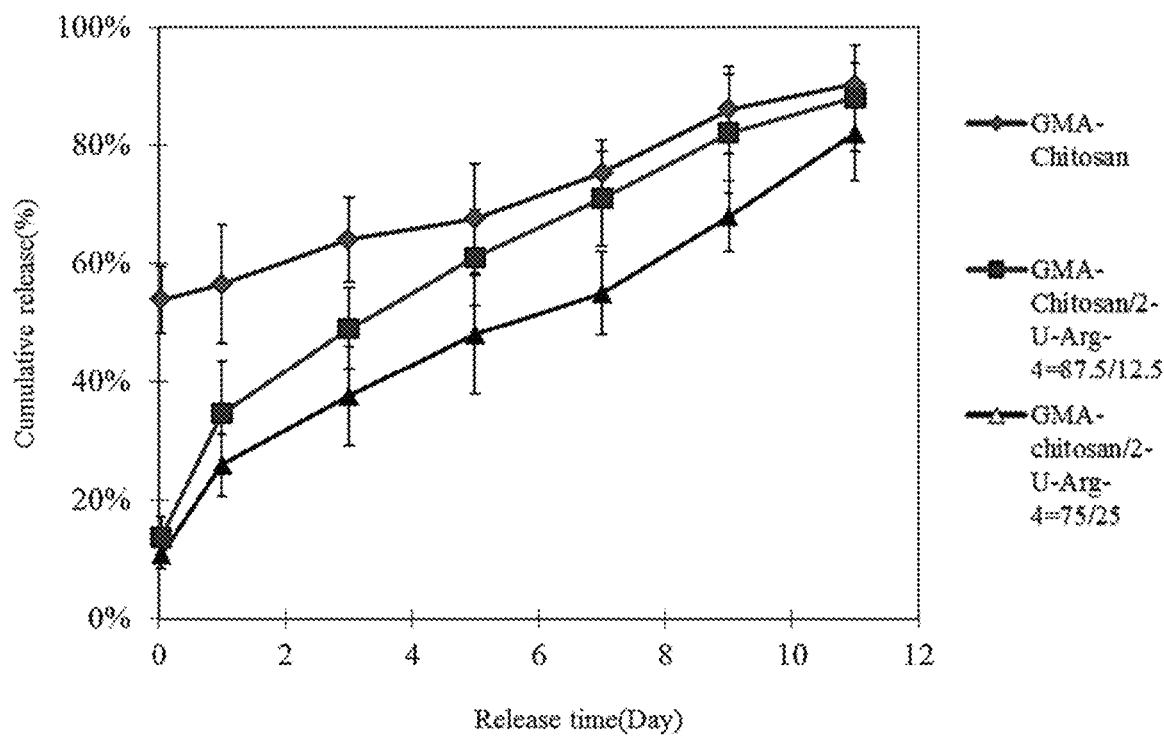
FIG. 23 shows representative bovine serum albumin (BSA) release profile of GMA-chitosan/2-U-arginine-4 hybrid hydrogels (100% GMA-chitoan hydrogel as control. The degree of substitution of GMA-chitosan is 37).

The BSA release data were further analyzed as a function of the square root of time for assessing whether such a BSA release from the GMA-Chitosan hydrogel would follow a Fickian diffusion mechanism. As shown in FIG. 18, a linear relationship in the first 7 days. In the case of diffusion-controlled system, the release behavior follows the Higuchi square-root of time relationship:

$$\frac{M_t}{M_\infty} = 4\left(\frac{Dt}{\pi l^2}\right)^{0.5}$$

for $0 \leq M_t/M_f \leq 0.6$ where $M_t$ and $M_f$ are the fraction of drug released at time t and at equilibrium, D is the diffusion coefficient of the drug in the matrix and l is the sample thickness. This confirms the BSA release kinetics in the GMA-Chitosan hydrogel in PBS is mainly a diffusion mechanism before the hydrogel lost its microstructure in the process of degradation. After 7 days, the release rate of BSA was influenced by the degradation and shows higher slope. This means the degradation mechanism of the GMA-Chitosan matrix could accelerate the BSA release from the matrix after a period of diffusion-controlled release.

Example 3

This example shows a water soluble photocrosslinkable chitosan derivatives. A two-step synthesis method was developed by utilizing the reaction between the epoxy groups of glycidyl methacrylate and the amine and hydroxyl groups of chitosan in aprotic organic solvent (DMSO), methacrylate group was grafted on the chitosan molecule. GMA-Chitosan can be photocrosslinked to fabricate transparent hydrogel in aqueous solution. And the integration of cationic Arg-PEA with a newly developed water soluble chitosan derivative and their chemical, physical, mechanical, and morphological properties are presented. The hybrid products may be the good candidates as tissue engineering scaffolds and the extracellular matrix (ECM) analogue model for the study of inflammation during healing.

Scheme 5: Fabrication of GMA-chitosan/2-U-Arg-4 PEA hybrid hydrogel
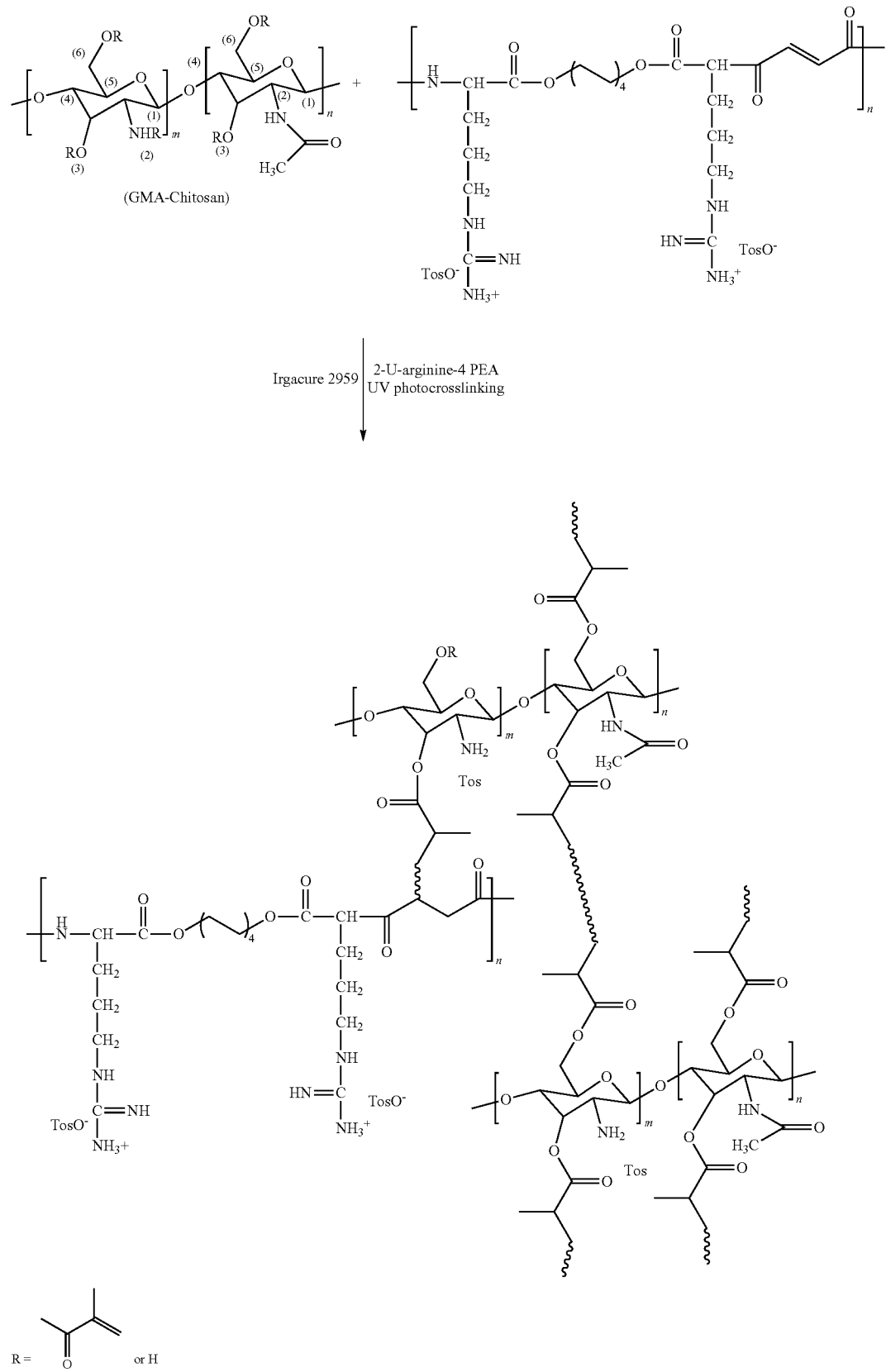

TABLE 6

Mechanical properties of GMA-chitosan/2-U-Arg-4 = 2/1 hybrid hydrogel

| Hydrogel types | Initial modulus (kPa) |
|---|---|
| GMA-chitosan hydrogel | 5.395 ± 0.8 |
| GMA-chitosan/2-U-Arg-4 = 2/1 | 6.103 ± 0.3 |

Hybrid hydrogels of chitosan derivative and cationic Arg-based PEA has been developed by using photo cross-linking method. These polysaccharide and pseudo-protein hybrid hydrogels were examined for their mechanical property, swelling ratio, microstructure and enzymatic biodegradation rate. The BSA release study showed the hybrid hydrogels having higher Arg-PEA contents showed consistently sustained BSA release rates and significantly lower burst release due to the electrostatic interaction. These polysaccharide and pseudo-proteins hybrid hydrogels may have promising biomedical applications.

Example 4

In this example, a family of biodegradable and charged hybrid hydrogels was designed and fabricated via a photo-means in an aqueous medium from both hyaluronic acid (HA) precursor, one of the most biologically active biopolymers, and a relatively new amino acid-based synthetic poly(ester amide) (AA-PEA) precursor. HA precursor was successfully synthesized by incorporating unsaturated moiety (aminoethyl methacrylate, AEMA), while the AA-PEA precursor was synthesized from unsaturated arginine-based poly(ester amide)s (UArg-PEA). These two water soluble precursors were photo-crosslinked to formulate a new family of biodegradable hybrid hydrogels. The chemical structure of these hybrid hydrogels was characterized, and their swelling, mechanical, morphological, biodegradation and drug release properties of these hybrid hydrogels were examined as a function of the feed ratio of these 2 precursors and the degree of substitution (DS) of AEMA groups in HA-AEMA. The resulting hybrid hydrogels showed 400-600% swelling ratio, and pH dependent swelling was only observed in a pure HA-AEMA hydrogel. Compression modulus of the hybrid hydrogels ranged from 108.6 to 278.3 KPa, and higher density hydrogels showed a little higher modulus. The pure HA-AEMA hydrogel showed the highest modulus when comparing to the hybrid hydrogels. The hybrid hydrogels showed distinctive sheet-like multi-layer 3D microporous structure. Upon a trypsin catalyzed biodegradation, the hybrid hydrogels showed 50 to 70% weight loss within 6 days, while the same hybrid hydrogels showed less than 5% weight loss in a PBS medium. The hybrid hydrogels showed a sustained release of bovine serum albumin (BSA) over 25 hrs, while the pure HA-AEMA hydrogel exhibited a complete release of BSA within 5 hrs.

Experimental section: Materials: DL-2-Allylglycine (AG), L-Arginine (Arg), p-toluenesulfonic acid monohydrate (TosOH.H$_2$O), diethylene glycol, tetraethylene glycol, hydroquinone, sebacoyl chloride, succinyl chloride, 1,4-butanediol, 1,6-hexanediol (Alfa Aesar, Ward Hill, Mass.), and p-nitrophenol (J. T. Baker, Phillipsburg, N.J.) were used without further purification. Triethylamine from Fisher Scientific (Fairlawn, N.J.) was dried via refluxing with calcium hydride and then distilled. Other solvents, such as benzene, ethyl acetate, acetone, n-butanol, N,N-dimethylacetamide (DMAc), and dimethyl sulfoxide (DMSO), were purchased from VWR Scientific (West Chester, Pa.) and were purified by standard methods before use. Bovine serum albumin (BSA), Sodium hyaluronate, the sodium salt of hyaluronic acid (HA), with a molecular weight of 1,000,000 was obtained from Sigma-aldrich. N-(3-Dimethylaminopropyl)-N'-ethylcarbodiimide hydrochloride (EDC), N-Hydroxysulfosuccinimide (NHS), 2-aminoethyl methacrylate hydrochloride (AEMA), Dimethyl sulfoxide (DMSO) were obtained from Junsei Chemical Co. (Tokyo, Japan). Double-distilled water was used for the following experiments. All chemicals were used without further purification. Buffer solutions, pH 3, pH 7, and pH 10, were purchased by VWR Scientific (West Chester, Pa.).

Synthesis of the Arg-based PEA and HA-AEMA precursors: The synthesis of the Arg-based PEA precursor having pendant photo-reactive vinyl groups was very recently reported, and in this example, the cationic 2-Arg-4-AG-2EG precursor was synthesized according the published procedures. Briefly, the monomers synthesized could be divided into two categories: di-p-nitrophenyl ester of dicarboxylic acids (I); di-p-toluenesulfonic acid salts of bis-L-arginine (or bis-DL-2-allylglycine) esters (II). The synthesis of di-p-nitrophenyl esters of dicarboxylic acids (I) monomer N-x (x indicated number of methylene group in diacid) was based on the method by reacting dicarboxylic acyl chlorides with p-nitrophenol. Scheme 6 shows the chemical structure of 2-Arg-4-AG-2EG as the pseudo-protein precursor.

Scheme 6. Chemical structure of Arg-PEA used for this example (x = 2, y = 4, n = 2, i.e.2-Arg-4AG-2EG).

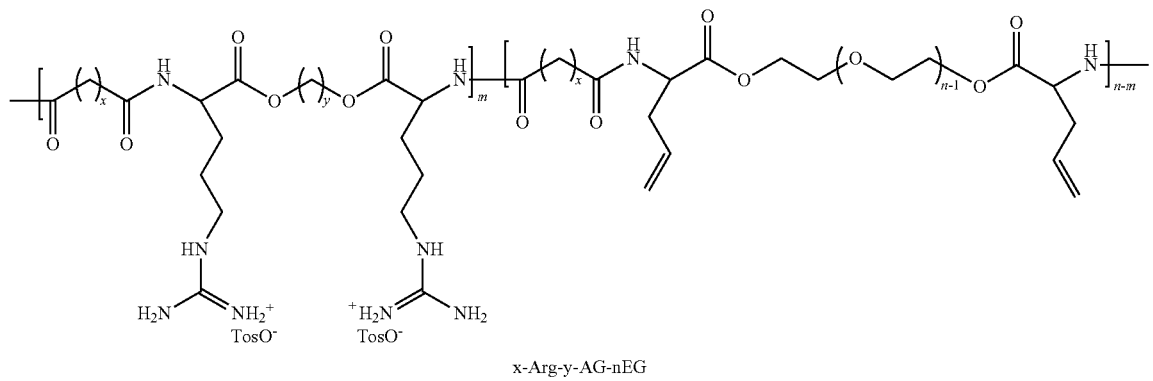

x-Arg-y-AG-nEG

Scheme 6. Chemical structure of Arg-PEA used for this example (x=2, y=4, n=2, i.e. 2-Arg-4AG-2EG).

Synthesis of aminoethyl methacrylate HA (HA-AEMA) (see chemical structure in scheme 7.) Sodium salt of HA (MW 1,000 K, 2 μmol) was dissolved in 100 mL of water. Then, EDC (15 mmol), NHS (15 mmol), and AEMA (10 mmol) were added to the solution and mixed for one day. The reaction product was dialyzed (dialysis membrane cut-off MW is 8,000) against a large excess amount of water and then lyophilized for three days(LABCONCO, FreeZone 2.5, VWR). The HA-AEMA obtained was characterized with Varian $^1$H NMR (Palo Alto, Calif.) Unity Inova 300-MHz using D20 as a solvent.

Fabrication of HA-AEMA and Arg-PEA hybrid hydrogels: The predetermined amounts of HA-AEMA and 2-Arg-4-AG-2EG precursors were dissolved in distilled deionized water (0.5 mL). Photo-initiator, ammonium persulfate, 5 mg was added to the hydrogel precursor solution. The mixture was vigorously stirred and placed under a long wavelength UV lamp (365 nm, 100 W) for 20 min. The feed ratios of the HA-AEMA to 2-Arg-4-AG-2EG precursors were summarized in Table 7.

TABLE 7

Feed composition of the HA-AEMA and 2-Arg-4-AG-2EG PEA precursors for the photo fabrication of the HA-AEMA/Arg-PEA hybrid hydrogels.

| Precursors | Weight (mg) | | | | | |
|---|---|---|---|---|---|---|
| HA-AEMA (DS 40.2%) | 40 | 30 | 20 | — | — | — |
| HA-AEMA (DS 31.5%) | — | — | — | 40 | 30 | 20 |
| Arg-PEA* | 0 | 20 | 30 | 0 | 20 | 30 |

*2-Arg-4-AG-2EG-25

Mechanical property test: Compression moduli of the hybrid hydrogels were measured by dynamic mechanical analyzer (DMA Q800 V7.5 Build 127). Hydrogel samples (disc, diameter 1.2 cm) were swollen in water for 24 hrs before this testing. The maximum force applied was 0.1 N at the rate of 0.0100 N/min. The modulus, $E_c$, was calculated by the ISO 604 software at the strain value 0.05-0.25%.

$$Ec=(\sigma_2-\sigma_1)/(\varepsilon_2-\varepsilon_1) \tag{1}$$

σ: stress ε: strain

Swelling test: Swelling ratio of the hybrid hydrogels was measured in buffer media of different pHs (pH 3, pH 7, and pH 10) over time. Hydrogel samples were dried in a vacuum oven at 40° C. for 48 hours before swelling test. The hydrogel samples were weighed and then immersed in 10 mL of buffer solutions. The samples were removed at predetermined periods, surface water was gently removed by bloatting with a dry paper and the hydrogel sample was then weighed until a constant weight. The swelling ratio was calculated by the following equation.

$$S_w=(W_s-W_d)/W_d \times 100 \tag{2}$$

$S_w$: Swelling ratio
$W_s$: Weight of the hydrogel in a swollen state at time t
$W_d$: Weight of the hydrogel in a dry state at time 0

Scanning electron microscopy: The interior and surface morphology of the hybrid hydrogels after swelling and biodegradation in trypsin solution was measured by a scanning electron microscope (Leica Stereoscan, model no. 440). The swollen hydrogel samples were first freeze dried by cryofixation technique. To conserve the delicate inner structure of the hydrogel, the swollen hydrogel samples were frozen using the liquid nitrogen and dried for 48 hours using a Virtis (Gardiner, N.Y.) freeze drier. The dried hydrogels were mounted onto aluminum stub and coated with gold/palladium (60%/40%) using sputter coater (Denton Vacuum Desk II). The samples were observed using SEM at 15 kV.

Biodegradation of HA-AEMA/Arg-PEA hybrid hydrogels: The biodegradation HA-AEMA and HA-AEMA/Arg hybrid hydrogels were carried out in a small vial containing a small piece of known weight dry hydrogel sample (ca. 50 mg) and 10 mL of PBS buffer (pH 7.4, 0.1 M) with trypsin at the concentration of 0.1 mg/mL. A pure PBS buffer was used as a control. The vial was then incubated at 37° C. with a constant shaking rate (50 rpm). The incubation media were refreshed daily in order to maintain enzymatic activity. At predetermined immersion durations, hydrogel samples were removed from the incubation medium, washed gently with distilled water, and then lyophilized in vacuum with FreeZone Benchtop and Console Freeze Dry System (Model 7750000, LABCONCO Co., Kansas City, Mo.) at -48° C. for 72 h and then weighted to a constant weight. The degree of biodegradation was estimated from the weight loss of the hydrogel based on the following equation:

$$W_l(\%) = \frac{W_o - W_t}{W_o} \times 100 \tag{3}$$

Where $W_l$ is the weight loss percent, $W_o$ was the original weight of the dried hydrogel sample before immersion, and $W_t$ was the dry HA-AEMA and HA-AEMA/Arg hybrid hydrogels sample weight after t incubation time. The weight loss averaged of three specimens was recorded.

In-vitro release of BSA from HA-AEMA/Arg-PEA hybrid hydrogels. Bovine serum albumin (BSA) was chosen as the model drug for their controlled release. BSA solution (5.0 wt %) was prepared by dissolving 2 g BSA in 40 ml of PBS solution (pH 7.4, 0.1 M). Before drug loading, both pure HA-AEMA and HA-AEMA/Arg-PEA hydrogels were dried under vacuum for 2 day. The drug was then loaded into these dry hydrogels by placing them into the above 5.0 wt % BSA solution at 25° C. for 2 days to reach equilibrium state.

BSA release study were performed by immersing the above BSA-loaded hydrogel samples in a glass bottle filled with a 50 mL PBS solution (pH 7.4, 0.1 M) at 37° C. At predetermined periods, 4 mL of aliquot of the buffer solution was removed from the glass tube and 4 mL of fresh buffer solution was added back to maintain the same total solution volume. The concentration of the BSA in the aliquot removed was measured by using a UV spectrophotometer (Lambda Bio40 UV-Vis spectrometer, Perkin-Elmer) at 280 nm and a BSA calibration curve. The results were presented in terms of the cumulative release as a function of time, and the cumulative BSA release (%) was calculated as:

Cumulative BSA release (%)=$(M_t/M_0) \times 100$, where $M_t$ is the amounts of BSA released from the hydrogel at time t, and $M_0$ is the initial BSA loaded into the hydrogel. In this example, the amount of BSA initially loaded in the hydrogel was calculated as: $M_0=(W_e-W_d) \times 5.0$ wt %, where $W_e$ is the weight of swollen hydrogel in the BSA solution, $W_d$ is the initial weight of the dried hydrogels before immersion, and 5.0 wt % is the concentration of BSA aqueous solution.

Figure 24:
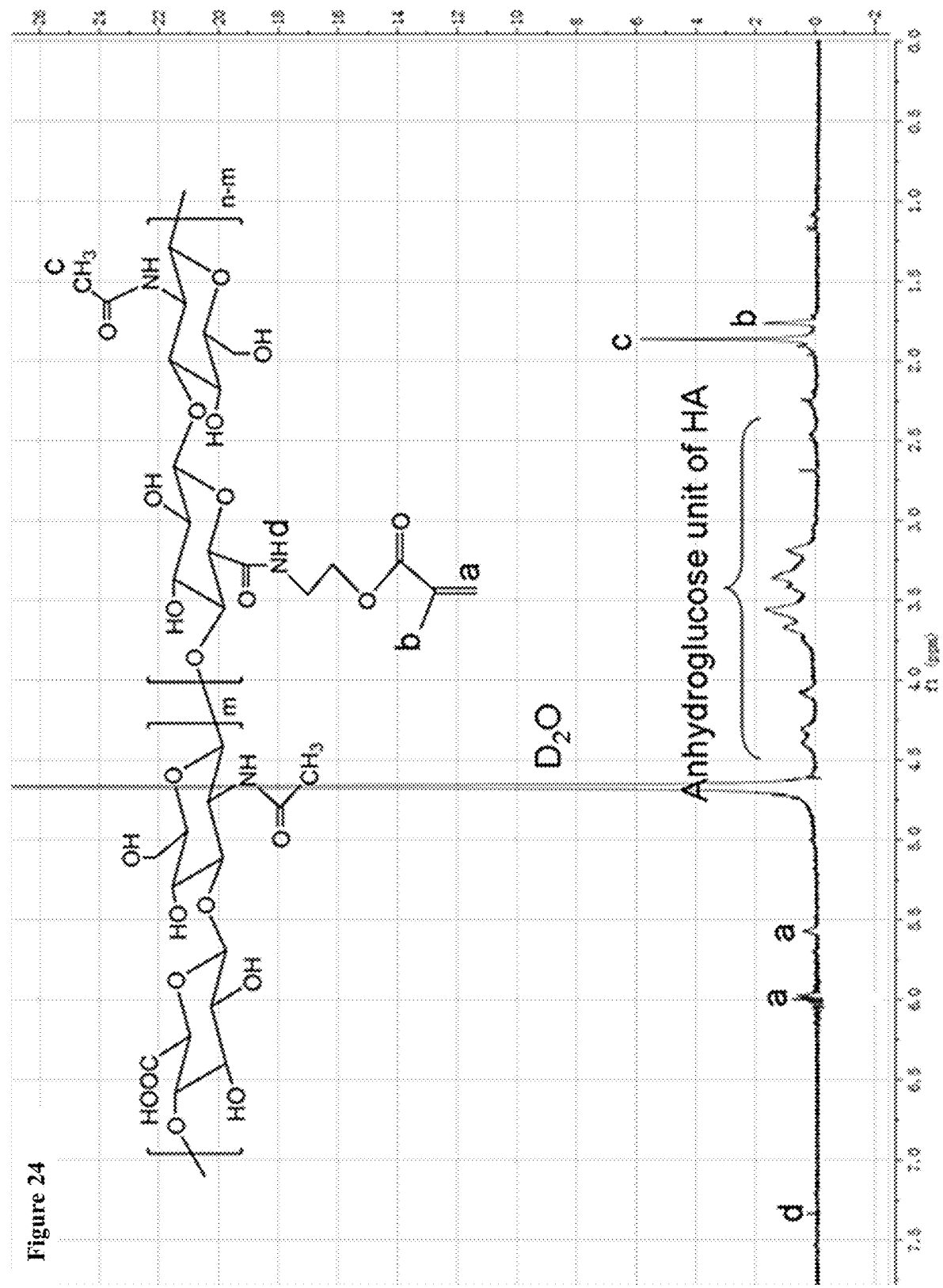
FIG. 24 shows a $^1$H NMR spectrum of HA-AEMA (solvent D20).

Synthesis of aminoehtyl methacrylic hyaluronic acid (HA-AEMA): The synthesis of HA-AEMA precursor is shown in Scheme 7. The amino ethyl methacrylate moiety was attached onto the free —COOH site of HA, and was verified by $^1$H NMR. The degree of AEMA substitution in HA was determined by the integrated peak areas of methacrylate unit of AEMA at δ (6.1 and 5.6 ppm) which confirmed the coupling of the acryloyl group and methyl resonance of acetamido moiety of HA at δ (1.85-1.95 ppm) (FIG. 24). By changing the amounts of AEMA to HA in the reaction, the degree of substitution of AEMA in HA-AEMA could be controlled, and in this example, two degrees of AEMA substitution in HA were obtained, i.e., 40.2% and 31.5%. This synthesis strategy of HA-AEMA precursor has a major advantage: a very high yield, 95%.

Scheme 7. Illustration of synthesis of HA-AEMA precursor from hyaluronic acid (HA) and 2-aminoethyl methacrylate hydrochloride (AETA).

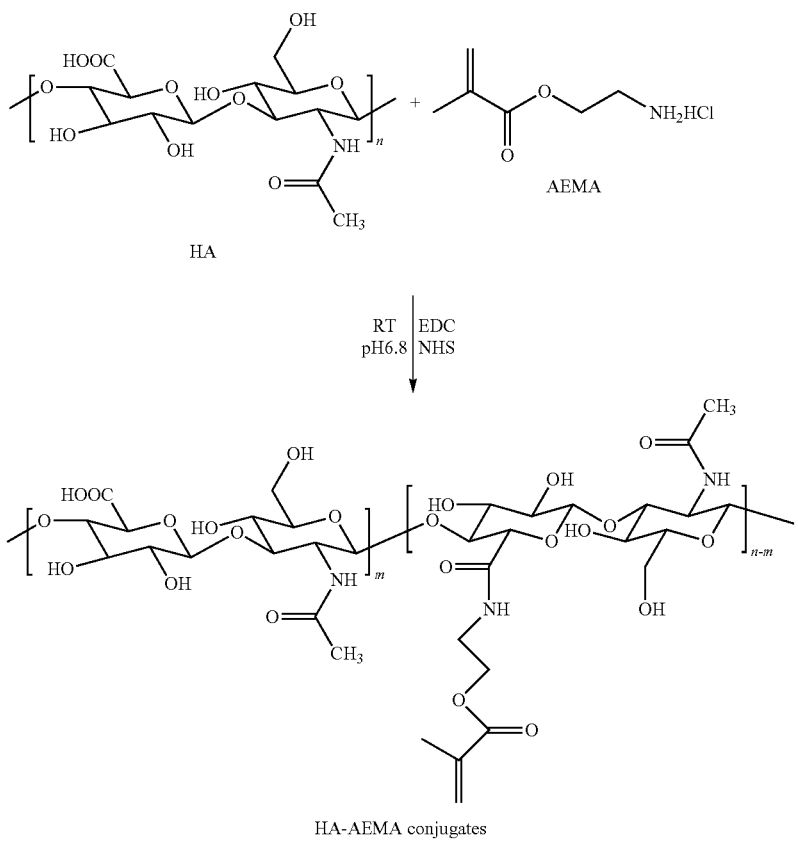

Figure 25:
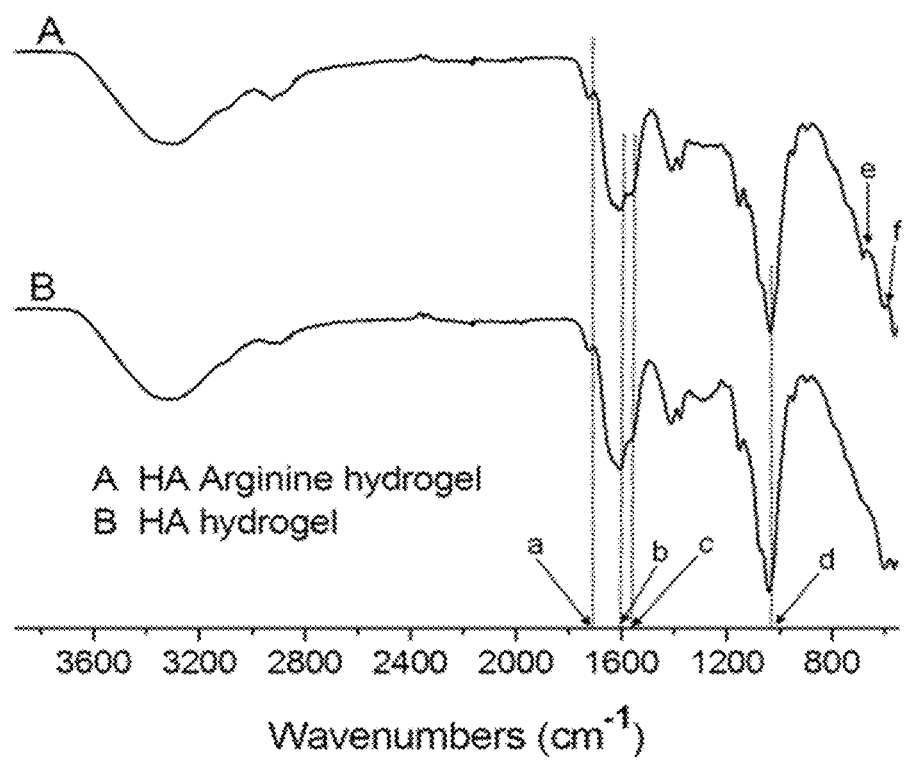
FIG. 25 shows FT-IR spectra of HA-AEMA and HA-Arginine hydrogel. A) HA-AEMA/Arg-PEA hybrid hydrogel; B) pure HA-AEMA hydrogel. a: C=O stretching; b: amide I (1640 cm-1); c: amide II (1560 cm-1); d: C—OH stretching of HA; e & f: C—H stretching of benzene in the toluene sulfonic acid counter ion attached to the guanidine group of arginine part of the Arg-PEA precursor.
Figure 26:
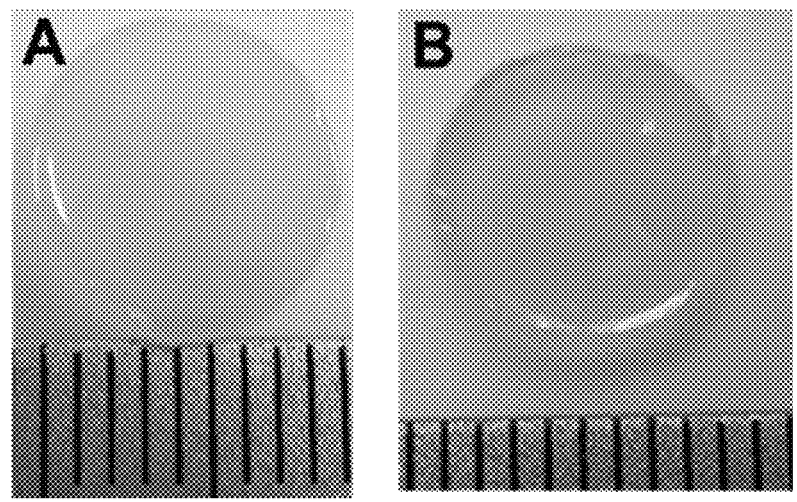
FIG. 26 shows a representative image of the hydrogel. (A)HA-AEM hydrogel (B)HA-AEMA/Arg-PEA hybrid hydrogel before swelling (D.S 40.2%, 40 wt. % Arg-PEA).

EDC: 1-(3-Dimethylaminopropyl)-3-ethylcarbodiimide hydrochloride
NHS: N-Hydroxysuccinimide
AEMA: 2-Aminoethyl methacrylate hydrochloride HA-AEMA and Arg-PEA hybrid hydrogel formation: The hybrid hydrogels photo-fabricated from the Arg-PEA and HA-AEMA precursors showed the characteristic band of HA-AEMA at 1740 cm$^{-1}$ (C=O stretching from the HA amide group) as shown in FIG. 25, The typical amide I and II bands at 1650 and 1540 cm$^{-1}$ and divided bands of symmetric C—H bending from the benzene group (from to toluene sulfonic acid counter ion attached to guanidine group of the arginine part of Arg-PEA) at 720 and 650 cm$^{-1}$ were also observed, which confirmed the formation of the HA-AEMA/Arg-PEA hybrid hydrogel. The chemical structure of the crosslinked hydrogel and the images of the hydrogel were shown in Scheme 8 and FIG. 26.

The HA-AEMA/Arg-PEA hybrid hydrogel formulation was also confirmed by the elemental analysis data. As shown in Table 8, the elemental contents of sulfur in both pure HA-AEMA hydrogels is zero, but in the four HA-AEMA/Arg PEA hybrid hydrogels, the elemental content of sulfur is 5.12%, 6.34%, 5.33%, 6.48%, respectively, these S data due to the presence of the toluene sulfonic acid counter ion attached to the guanidyl group of arginine confirmed the successful formation HA-AEMA/Arg-PEA hybrid hydrogels.

TABLE 8

Elemental analysis of content in the hydrogels.

| Hydrogels | C % Cal. | C % Found. | O % Cal. | O % Found. | N % Cal. | N % Found. | S % Cal. | S % Found. |
|---|---|---|---|---|---|---|---|---|
| Pure HA-AEMA hydrogel (D.S. 31.5%) | 46.16 | 41.23 | 44.16 | 43.28 | 4.78 | 3.76 | 0 | 0 |
| Pure HA-AEMA hydrogel (D.S. 40.2%) | 47.23 | 41.02 | 44.79 | 42.72 | 4.98 | 3.43 | 0 | 0 |
| HA-AEMA/Arg-PEA hydrogel (D.S.31.5%) (40 wt. % Arg-PEA) | 45.27 | 45.04 | 25.24 | 23.54 | 15.56 | 12.36 | 7.45 | 5.12 |

TABLE 8-continued

| Hydrogels | Elemental analysis of content in the hydrogels. | | | | | | | |
|---|---|---|---|---|---|---|---|---|
| | C % | | O % | | N % | | S % | |
| | Cal. | Found. | Cal. | Found. | Cal. | Found. | Cal. | Found. |
| HA-AEMA/Arg-PEA hydrogel (D.S.31.5%) (60 wt. % Arg-PEA) | 45.89 | 43.51 | 26.15 | 22.15 | 16.45 | 11.47 | 8.23 | 6.34 |
| HA-AEMA/Arg-PEA hydrogel (D.S. 40.2%) (40 wt. % Arg-PEA) | 46.79 | 42.15 | 26.34 | 23.02 | 16.87 | 14.28 | 7.98 | 5.33 |
| HA-AEMA/Arg-PEA hydrogel (D.S. 40.2%) (60 wt. % Arg-PEA) | 46.88 | 44.18 | 26.78 | 22.89 | 17.12 | 13.71 | 8.68 | 6.48 |

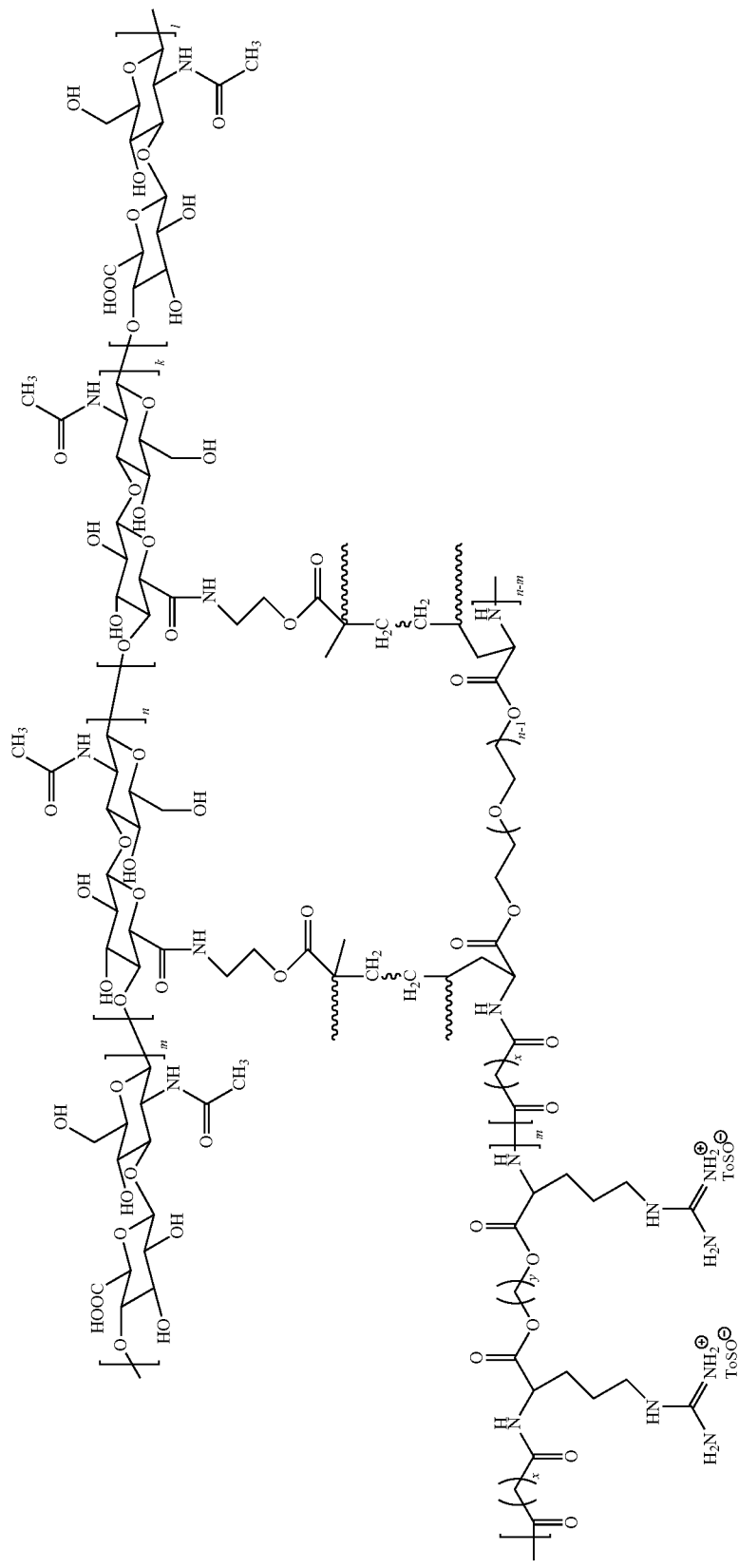
Scheme 8. Chemical structure of the crosslinked HA-AEMA/Arg-PEA hydrogel.

Mechanical property: The compression moduli of the hydrogel samples fabricated under a variety of conditions are shown in Table 9. In the pure HA-AEMA hydrogel category, a higher aminoethyl methacrylate substituted hydrogel showed a slightly higher modulus (278.3 KPa at 40.2% vs. 243.9 KPa at 31.5%). This relationship suggests that a higher AEMA substitution in HA-AEMA hydrogels led to a higher crosslinking density of the hydrogel, and hence a higher compression modulus. The compression modulus data of the pure HA-AEMA hydrogel in this example are significantly larger (near 10×) than the other published HA hydrogels.

TABLE 9

Compression modulus of hydrogel samples upon the various fabrication conditions.

| Hydrogel fabrication condition | Modulus (KPa) |
|---|---|
| Pure HA-AEMA hydrogel (D.S. 31.5%) | 243.9 |
| Pure HA-AEMA hydrogel (D.S. 40.2%) | 278.3 |
| HA-AEMA/Arg-PEA hydrogel (D.S. 31.5%) (40 wt. % Arg-PEA) | 145.5 |
| HA-AEMA/Arg-PEA hydrogel (D.S. 31.5%) (60 wt. % Arg-PEA) | 136.6 |
| HA-AEMA/Arg-PEA hydrogel (D.S. 40.2%) (40 wt. % Arg-PEA) | 135.2 |
| HA-AEMA/Arg-PEA hydrogel (D.S. 40.2%) (60 wt. % Arg-PEA) | 108.6 |

The HA-AEMA/Arg-PEA hybrid hydrogels, however, showed lower moduli than the pure HA-AEMA hydrogels, and as the amounts of the incorporated Arg-PEA precursor increased, the modulus of the hybrid hydrogel decreased, regardless of the DS of AEMA in HA. The hybrid hydrogels having the higher contents of the Arg-PEA moiety (60%) became quite soft than that of lower Arg-PEA contents, and broke easily during handling and mechanical testings. The possible cause behind the lower modulus in the HA-AEMA/Arg-PEA hybrid hydrogels than a pure HA-AEMA hydrogel is the lower crosslinking density in the hybrid hydrogels. This is because the molecular weight of Arg-PEA unit (1,172) is significantly higher than the HA-AEMA unit (450), i.e., the density of the photo-reactive pendent vinyl group in Arg-PEA is less than that of HA-AEMA. Consequently, the incorporation of the Arg-PEA unit into HA-AEMA could lead to a lower level of crosslinked loose network structure, i.e., lower compression modulus. In addition, the pedant vinyl group chain length of Arg-PEA is shorter than that of HA-AEMA, and hence may not be as easily accessible for photo-crosslinking reactions as the pendant vinyl group in HA-AEMA precursor did. This Arg-PEA precursor effect was expected to depend on the Arg-PEA contents in the hybrid hydrogels, i.e., a higher Arg-PEA content (60%) should result in a lower modulus than the hybrid hydrogel having a lower Arg-PEA content (40%) as shown in Table 9. The lower level of crosslinked looser network structure in the HA-AEMA/Arg-PEA hybrid hydrogels was also confirmed in their interior morphology and relatively higher swelling than the pure HA-AEMA as shown below.

Figure 27A:
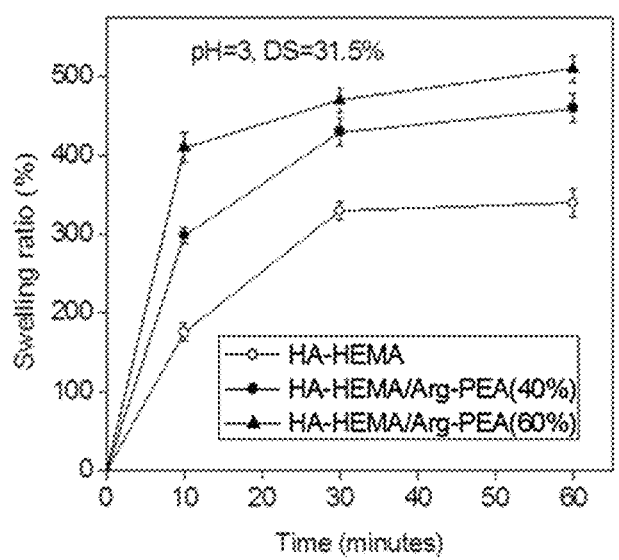
FIGS. 27A-C show representative effect of feed ratio of the precursors and pH medium on the swelling ratio of HA-AEMA pure hydrogel and HA-AEMA/Arg-PEA hybrid hydrogel (D.S 31.5%) at 25° C.
Figure 27B:
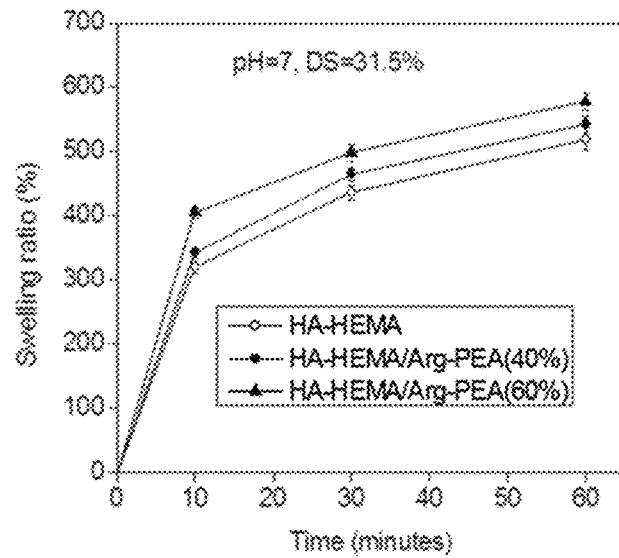
Figure 27C:
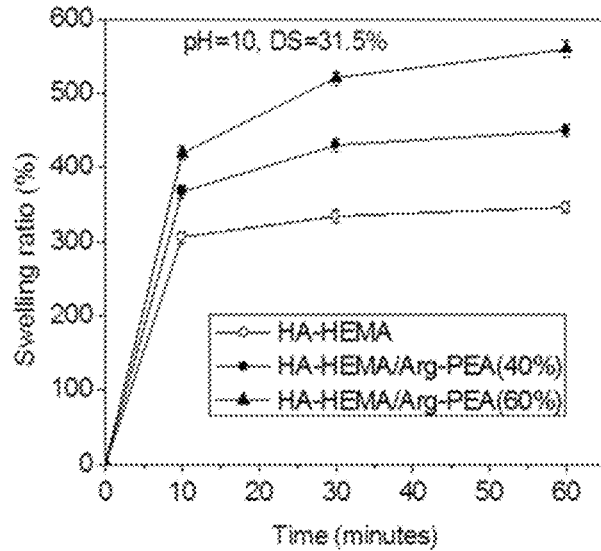
Figure 28:
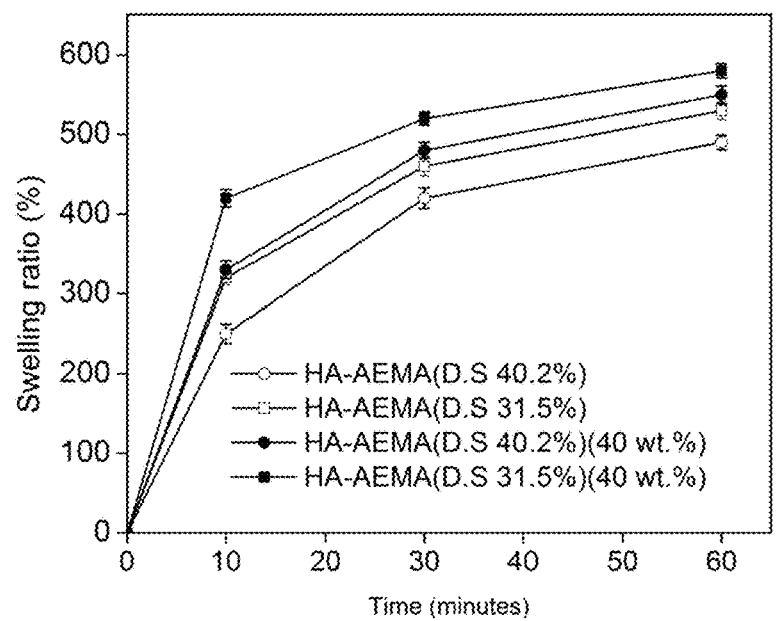
FIG. 28 shows representative effect of AEMA degree of substitution in HA on the swelling kinetics of HA-AEMA pure hydrogel and HA-AEMA/Arg-PEA hybrid hydrogels in pH=7 medium at 25° C.

Swelling Kinetics and Ratios: The swelling data of the HA-AEMA/Arg-PEA hybrid hydrogels and pure HE-AEMA hydrogels are given in FIGS. 27 and 28. The pure HA-AEMA hydrogels showed an abrupt increase in swelling at the early stage, e.g., within the first 10 minutes, all of HA-AEMA and HA-AEMA/Arg-PEA hybrid hydrogels absorbed 2~4 fold of water of their weights. After this initial burst swelling, the swelling ratio of the pure HA-AEMA hydrogels gradually increased until 1 hour. After 1 hour, most of the pure HA-AEMA hydrogels had already reached to an equilibrium, depending on the fabrication condition.

The difference of swelling ratio among the different D.S. of AEMA on the pure HA-AEMA hydrogels was not significant in all pH ranges. Hyaluronic acid is an extremely hydrophilic material and has inherently very high water contents. Therefore, the difference of D.S between 31.5% and 40.2% did not contribute significantly different swelling data. On the other hand, the contents of Arg-PEA in the HA-AEMA/Arg-PEA hybrid hydrogels play an important role in controlling swelling data as the data showed a higher swelling in all pH ranges in those HA-AEMA/Arg-PEA hybrid hydrogels having higher Arg-PEA contents (e.g., 60%). This is due to the inherent hydrophilic nature of arginine and lower crosslinking density with a higher feed ratio of hydrogel precursor Arg-PEA to HA-AEMA. The HA-AEMA/Arg-PEA (60%) hybrid hydrogel showed the highest swelling in all HA-AEMA/Arg-PEA hybrid hydrogels regardless the D.S. of AEMA in HA, Bae et al. reported the HA-AEMA pure hydrogel and equilibrated the hydrogel to 14 day, swelling ratio is about 300-400.

Figure 29:
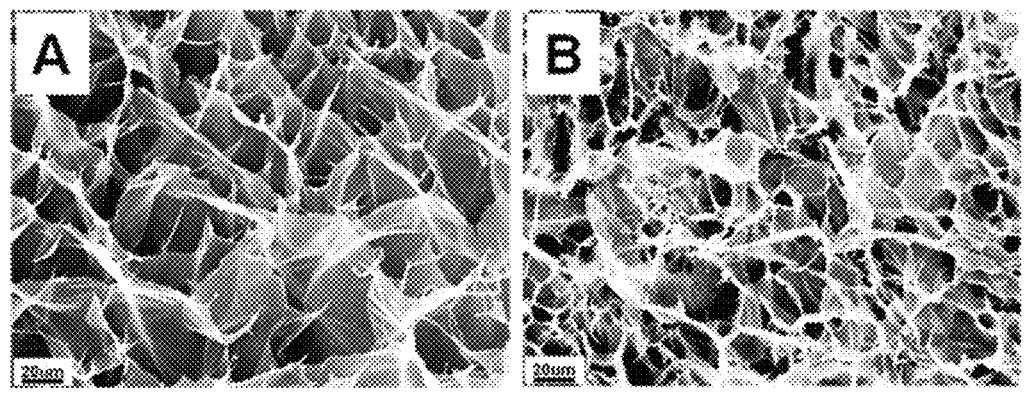
FIG. 29 shows representative effect of AEMA degree of substitution on the interior morphology of HA-AEMA pure hydrogels. (A) Pure HA-AEMA hydrogel (D.S 31.5%), (B) Pure HA-AEMA hydrogel (D.S 40.2%). The hydrogels were immersed in PBS (pH 7.4, 0.1M) at 25° C. for 2 days.
Figure 30:
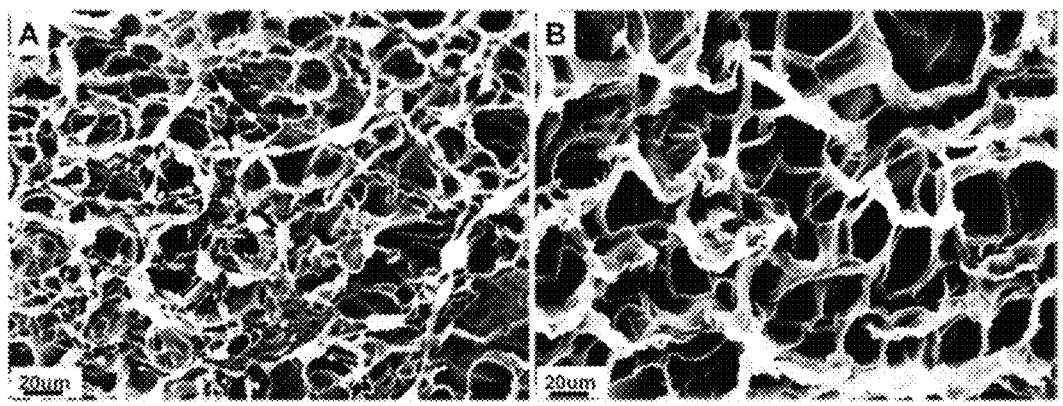
FIG. 30 shows representative effect of the Arg-PEA contents in the HA-AEMA/Arg-PEA hybrid hydrogels on their interior morphology from scanning electron micrographs. (A) HA-AEMA/Arg-PEA (40%), (B) HA-AEMA/Arg-PEA (60%). The AEMA degree of substitution is 31.5%. The hydrogels were immersed in PBS (pH 7.4, 0.1M) at 25° C. for 2 days.
Figure 31:
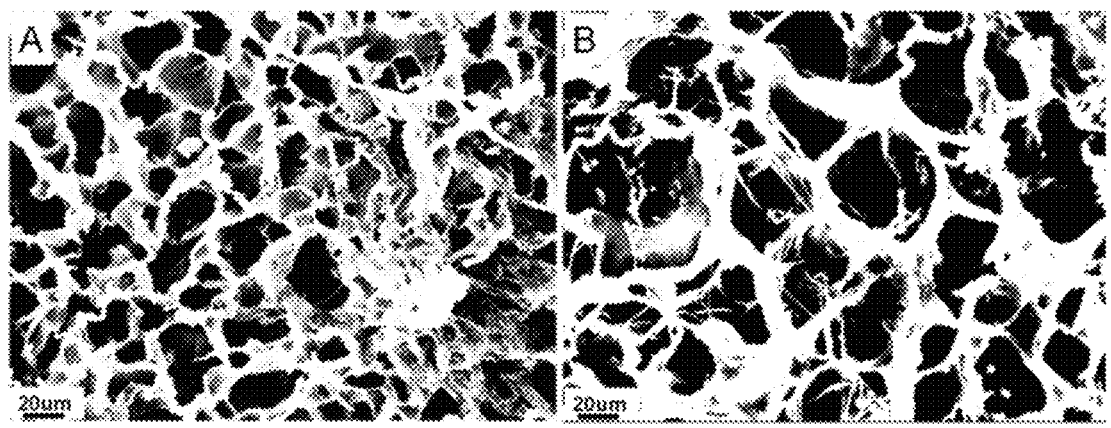
FIG. 31 shows representative effect of the Arg-PEA contents in the HA-AEMA/Arg-PEA hybrid hydrogels on their interior morphology from scanning electron micrographs. (A) HA-AEMA/Arg-PEA (40%), (B) HA-AEMA/Arg-PEA (60%). The AEMA degree of substitution is 40.2%. The hydrogels were immersed in PBS (pH 7.4, 0.1M) at 25° C. for 2 days.

Scanning Electron Microscopy (SEM): SEM photographs of the developed hydrogels are shown in FIGS. 29-31. All hydrogels showed the well-defined 3D pore structures in the swollen state.

FIG. 29 shows the swollen structure of pure HA-AEMA hydrogel having different AEMA degree of substitution. The higher D.S (40.2%) HA-AEMA pure hydrogel (FIG. 29B) shows smaller pore structure than the lower DS (31.5%) due to tighter crosslinking. shows larger pore structure. The pore cell walls appear thinner and more flexible in the pure HA-AEMA hydrogels having a lower DS (31.5%) than the same hydrogel at a higher DS. The thicker and less flexible appearance of the 3D cell walls in those hydrogels having a higher degree of substitution of AEMA in HA was also observed in the HA-AEMA/Arg-PEA hybrid hydrogels shown in FIG. 29 (DS 31.5%) & 9 (DS 40.2%).

FIGS. 30 and 31 show the swollen pore structures of the HA-AEMA/Arg-PEA hybrid hydrogels having different amounts of Arg-PEA precursors. A smaller pore size was observed in all HA-AEMA/Arg-PEA hybrid hydrogels regardless of D.S. As the feed ratio of Arg-PEA to HA-AEMA precursors increased (from 40% to 60%), the resulting hybrid hydrogels exhibited larger average pore size, regardless of the degree of substitution of AEMA in HA (FIG. 30B vs. 30A, or FIG. 31B vs. 31A). This is attributed to the looser network structure having the Arg-PEA segment as described previously under the compression modulus data. Therefore, both the DS and the amounts of Arg-PEA could affect the pore size of the resulting HA-AEMA pure hydrogel and HA-AEMA hybrid hydrogel, respectively.

Biodegradation of the HA-AEMA/Arg hybrid hydrogel. The biodegradation property of the HA-AEMA/Arg-PEA hydrogels using trypsin enzyme was examined in terms of the weight loss and SEM morphology of the HA-AEMA/Arg-PEA hybrid hydrogels. As shown in FIG. 31, the weight loss of the HA-AEMA/Arg hybrid hydrogels depended on both the crosslinking density of ester bonds and the Arg-PEA contents in the HA-AEMA/Arg-PEA hybrid hydrogels. Trypsin was chosen as the model enzyme because it could hydrolyze ester linkages at the C-terminal of hydrophilic a-amino acids like L-lysine and L-arginine.

The pure HA-A EMA hydrogels in a PBS solution (without trypsin) showed only 6.6% weight loss at the end of 6 days, while the weight loss of the HA-AEMA/Arg-PEA hybrid hydrogels in the presence of trypsin medium reached 50-70%, depending on the DS of AEMA and Arg-PEA contents in the hybrid hydrogels. The weight loss rate of the HA-AEMA/Arg-PEA hybrid hydrogels having higher DS of AEMA in HA was slower than the hybrid hydrogels having a lower D.S. of AEMA. This is attributed to the available photo-reactive pendant vinyl groups in in AEMA as a higher AEMA DS in HA-AEMA precursor could lead to a higher crosslinking density in the HA-AEMA/Arg-PEA hybrid hydrogels, i.e., tighter network structure and hence a slower rate of weight loss. This could also be confirmed in the swelling ratio data demonstrated in FIG. 28, a higher D.S led to a higher cross-linking density, thus a compact network of hydrogel which led to a, lower swelling ratio and hence slower weight loss was found.

Figure 32:
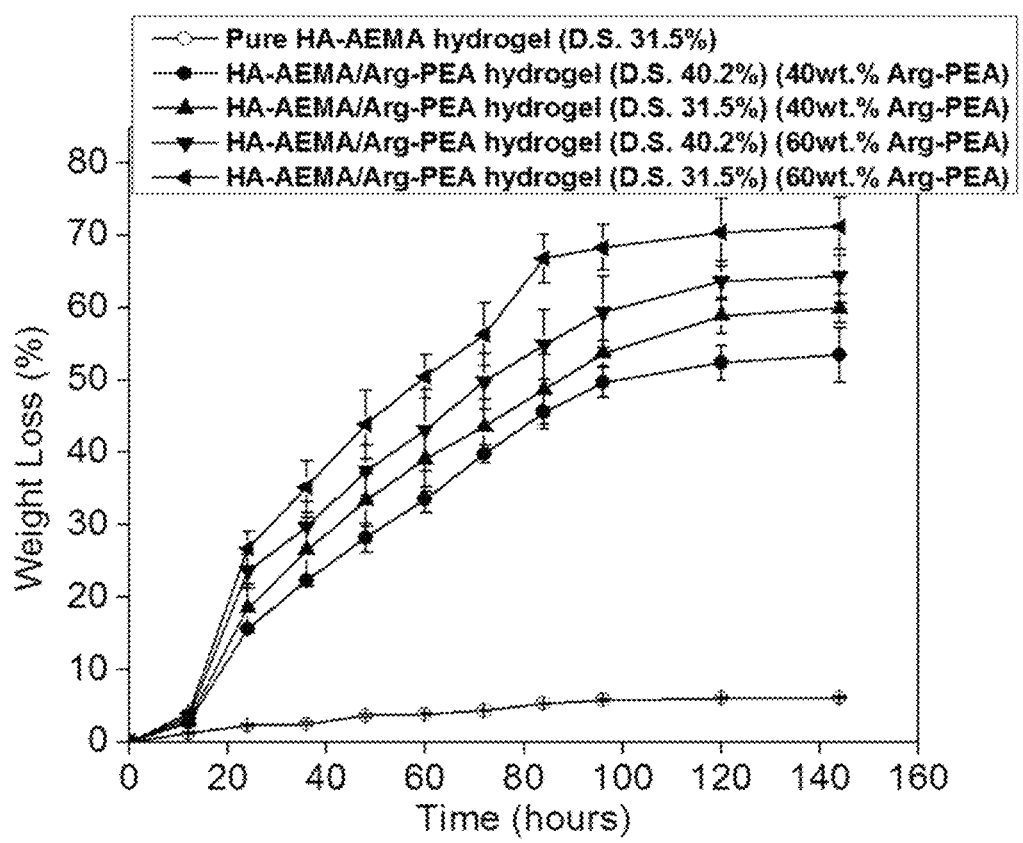
FIG. 32 shows representative weight loss of HA-AEMA/Arg hybrid hydrogels biodegradation in PBS (pH 7.4, 0.1 M) with the trypsin concentration (0.1 mg/mL) with HA-AEMA pure hydrogel (D.S 31.5%) as the control in pure PBS solution.

As the feed ratio of the Arg-PEA to HA-AEMA precursors increased, the hybrid hydrogels exhibited faster and higher weight loss, e.g., 40% with 60% of Arg-PEA in its hybrid hydrogel samples. As described previously in the data analysis of the effect of the Arg-PEA contents in the hybrid hydrogels on their compression modulus, those hybrid hydrogels having higher Arg-PEA contents exhibited lower crossing-liking density, looser network structure and higher water contents, and hence faster and higher weight loss. As shown in FIG. 32, the weight loss rate of HA-AEMA/Arg-PEA (40%) (D.S. 40.2%) is slower than HA-AEMA/Arg-PEA (40%) (D.S. 31.5%), and the same case for HA-AEMA/Arg-PEA (60%) (D.S. 40.2%) is slower than HA-AEMA/Arg-PEA (60%) (D.S 31.5%). And weight loss rate of HA-AEMA/Arg-PEA (40%) (D.S. 40.2%) is slower than HA-AEMA/Arg-PEA (60%) (D.S. 40.2%), HA-AEMA/Arg-PEA (40%) (D.S. 31.5%) is slower than HA-AEMA/Arg-PEA (60%) (D.S 31.5%). For example, at time of 48 hours, the weight loss of HA-AEMA/Arg-PEA (40%) (D.S 40.2%), HA-AEMA/Arg-PEA (40%) (D.S 31.5%), HA-AEMA/Arg-PEA (40%) (D.S 40.2%), HA-AEMA/Arg-PEA (60%) (D.S 40.2%), was 33.72%, 39.39%, 43.43%, 50.86%, respectively. At the time of 144 hours, the weight loss of of HA-AEMA/Arg-PEA (40%) (D.S 40.2%), HA-AEMA/Arg-PEA (40%) (D.S 31.5%), HA-AEMA/Arg-PEA (40%) (D.S 40.2%), HA-AEMA/Arg-PEA (60%) (D.S 40.2%), was 53.69%, 59.87%, 64.28%, 71.39%, respectively, compared to the Arg-PEA content in the hydrogels, that is to say, completely biodegraded. In general, the degradation ratio of hydrogel is related to several network parameters, such as the number of crosslinkers per backbone chain, molecular weight of backbone, and proportion of biodegradable groups in the main and side chain. With the hydrogel biodegrading, polymer chains freed by enzyme cleavage in the ester spots and the hydrogels became more hydrophilic duo to the more pending amino groups, some of the polymer chains migrated out of the hydrogel and dissolved in solution, thus the weight of the crosslinked network decreased.

Figure 33:
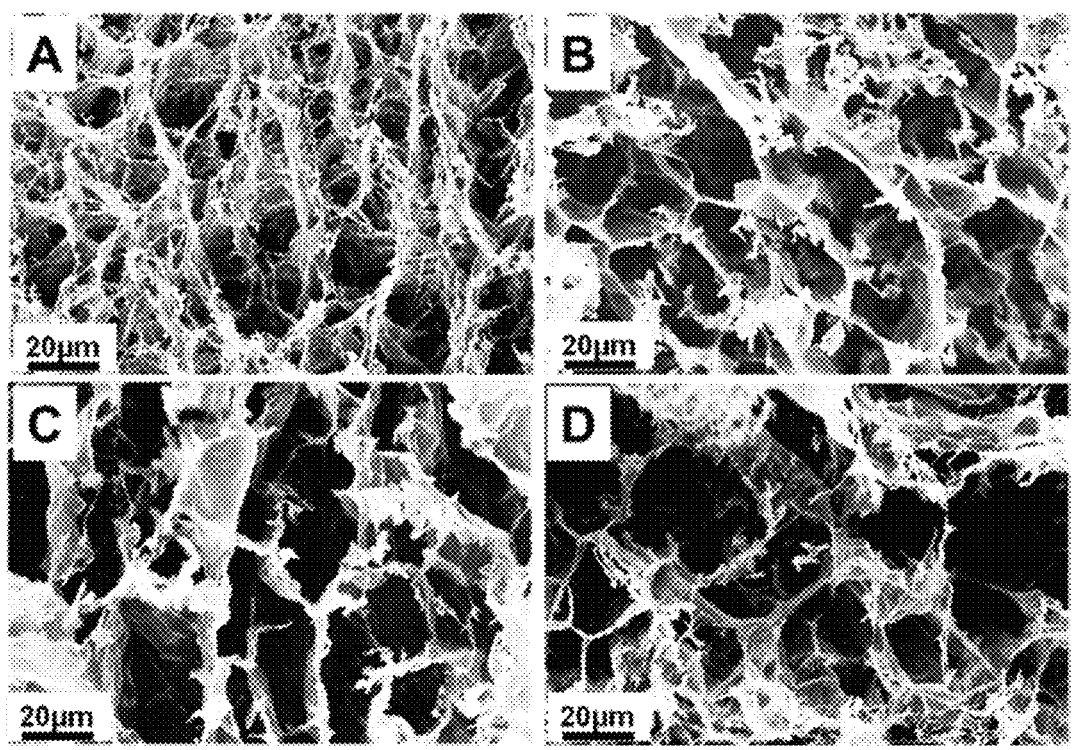
FIG. 33 shows representative SEM photographs of HA-AEMA/Arg hybrid hydrogels biodegradation in PBS (pH 7.4, 0.1 M) with the trypsin concentration (0.1 mg/mL) for 48 hours. (A) HA-AEMA/Arg-PEA (40%), (D.S. 40.2%), (B) HA-AEMA/Arg-PEA (60%), (D.S. 40.2%), (C) HA-AEMA/Arg-PEA (40%), (D.S. 31.5%), (D) HA-AEMA/Arg-PEA (60%), (D.S. 31.5%).

The morphologies of the hydrogel after trypsin enzymtic biodegradation were observed by SEM. During the biodegradation, the average pore size of the hydrogels increased. As shown in FIG. 33, the morphologies of the biodegradation hydrogels were different from the hydrogel before biodegradation, the average pore size increased and the regular three-dimensional porous unique network structure broken. It was found that the average pore size of the hybrid hydrogels with higher D.S. of HA-AEMA was smaller than the lower D.S of HA-AEMA, and pore size of higher content of Arg-PEA was larger than lower content of Arg-PEA after biodegradation. Compared with the hybrid hydrogels before biodegradation, the average pore size of the hybrid reached to a higher value, for example, the size of HA-AEMA/Arg-PEA (40%), (D.S 31.5%), HA-AEMA/Arg-PEA (60%), (D.S 31.5%), HA-AEMA/Arg-PEA (40%), (D.S 40.2%), HA-AEMA/Arg-PEA (60%), (D.S 40.2%) was 10 μm, 20 μm, 30 μm and 40 μm respectively, at the biodegradation time of 48 hours.

Figure 34:
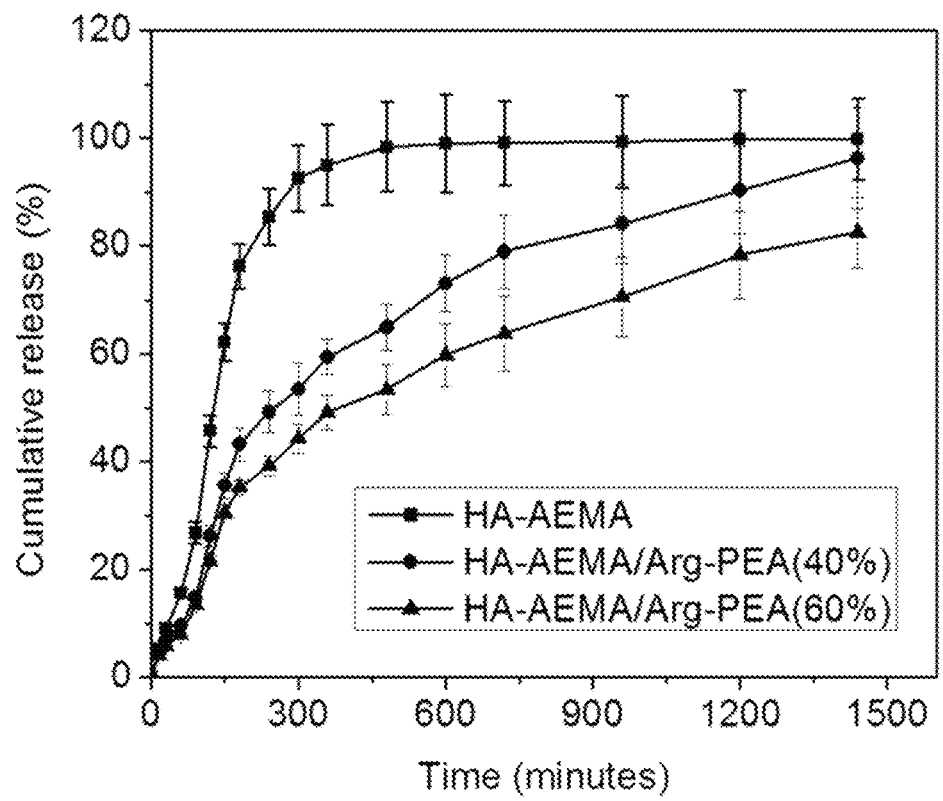
FIG. 34 shows representative controlled BSA release from the pure HA-AEMA and HA-AEMA/Arg hybrid hydrogels (40 wt. %, 60 wt. %). All the D.S. of AEMA in HA is 40.2%).

In-vitro Release of BSA: FIG. 34 demonstrates the release of BSA from the HA-AEMA and HA-AEMA/Arg hybrid hydrogels in PBS solution (pH 7.4, 0.1 M). It was found that there was a burst release at the initial stage for all the hydrogels. This was ascribed to BSA located near the hydrogels surface which can be released immediately from the hydrogel to the medium as soon as the hydrogels immerged into the buffer solution. After the initial burst release, the following release seemed to be a diffusion process. Due to the crosslinking density was in a sequence of HA-AEMA/Arg-PEA (D.S 40.2%)>HA-AEMA/Arg-PEA (D.S 31.5%), the average pore size was in the reverse order, thus the drug release rate was arranged in the reverse order, HA-AEMA/Arg-PEA (D.S 40.2%)<HA-AEMA/Arg-PEA (D.S 31.5%). Moreover, due to the positive guanidine groups of Arg-PEA in the hydrogels, the pKa of the arginine is about 12, the isoelectric point of BSA is about 5.6, the cationic amine groups in the hydrogels would attract the counter anionic BSA, thus the BSA release ratio decreased. The HA-AEMA/Arg-PEA (D.S 40.2%) and HA-AEMA/Arg-PEA (D.S 31.5%) hybrid hydrogels had a more sustained long drug release than pure HA-HEMA hydrogel. For example, at the time 240 min, the cumulative release of BSA for HA-AEMA hydrogel is 85.4%, while the HA-AEMA/Arg-PEA (D.S 40.2%) and HA-AEMA/Arg-PEA (D.S 31.5%) release ratio was 49.18% and 39.12%, respectively. At the time 360 min, BSA in HA-AEMA hydrogel was completely released, reached to 99.0%, but the cumulative release of HA-AEMA/Arg-PEA (D.S 40.2%) and HA-AEMA/Arg-PEA (D.S 31.5%) was 59.36% and 49.1%. At the time of 960 min, the cumulative release of HA-AEMA/Arg-PEA (D.S 40.2%) and HA-AEMA/Arg-PEA (D.S 31.5%) reached to 84.16% and 70.6%. Compared to the release of BSA, the drug release ratio is faster than the poly(c-caprolactone) maleic acid/poly(ethylene glycol) diacrylate hydrogels PGCL-Ma/PEGDA hydrogel networks and poly(acrylic acid) (PAAc)/acryloyl-poly(E-caprolactone)-2-hydroxylethyl methacrylate (AC-PCL-HEMA/PAA) hydrogel. The former BSA release lasted for one month and the latter for about 6 days. This may ascribed to the hydrophobic moiety of poly(ε-caprolactone) in the reported hydrogels. While in this example, the HA-AEMA and HA-AEMA/Arg-PEA hybrid hydrogel is completely hydrophilic moiety.

Discussion: Modification of hyaluronic acid to adopt unsaturated moiety was carefully controlled for a certain amount of substitution because large number of substitutions would lead to the insolubility in water of the modified polymer and small number of substitutions would not get enough crosslinks for mechanical stability. Therefore, the degree of substitution of the aminoethyl methacrylate groups onto hyaluronic acid was tailored to get both water-solubility and mechanical stability. Degree of substitution of 40.2% and 31.5% AEMA in HA was achieved in this research satisfying the both important characteristic for fabrication of HA-AEMA pure hydrogel. The difference between high D.S. and lower D.S. HA-AEMA pure hydrogel satisfying water-solubility and mechanical strength is not large, as a result, the property differences such as swelling ratio, modulus, and inner morphology were not significantly different.

However, the higher D.S. HA-AEMA pure and HA-AEMA/Arg-PEA hybrid hydrogel showed more stability in swelling and tended to disintegrate slower than the lower D.S. HA-AEMA pure and HA-AEMA/Arg-PEA hybrid hydrogel.

In swelling property, some pH-dependent swelling behavior of pure HA-AEMA hydrogel was observed. pH-dependent swelling tendency did not show significantly, however, the HA-AEMA pure hydrogels tended to swell less in pH 3 medium. It can be assumed that the hydrogen bonding among carboxylic acid groups and hydroxyl groups because the carboxylic groups in hyaluronic acid do not ionize in acidic pH. And hydrogels having arginine derivatives did not show any significant difference upon pH change because the carboxylic acid effect was diminished by the incorporation of cationic groups of arginine moiety.

All HA-AEMA pure hydrogel and HA-AEMA/Arg-PEA hybrid hydrogels showed a distinctive swollen structure in all preparation conditions. The sheet-like layers were observed in all swollen hydrogels.

Figure 9:
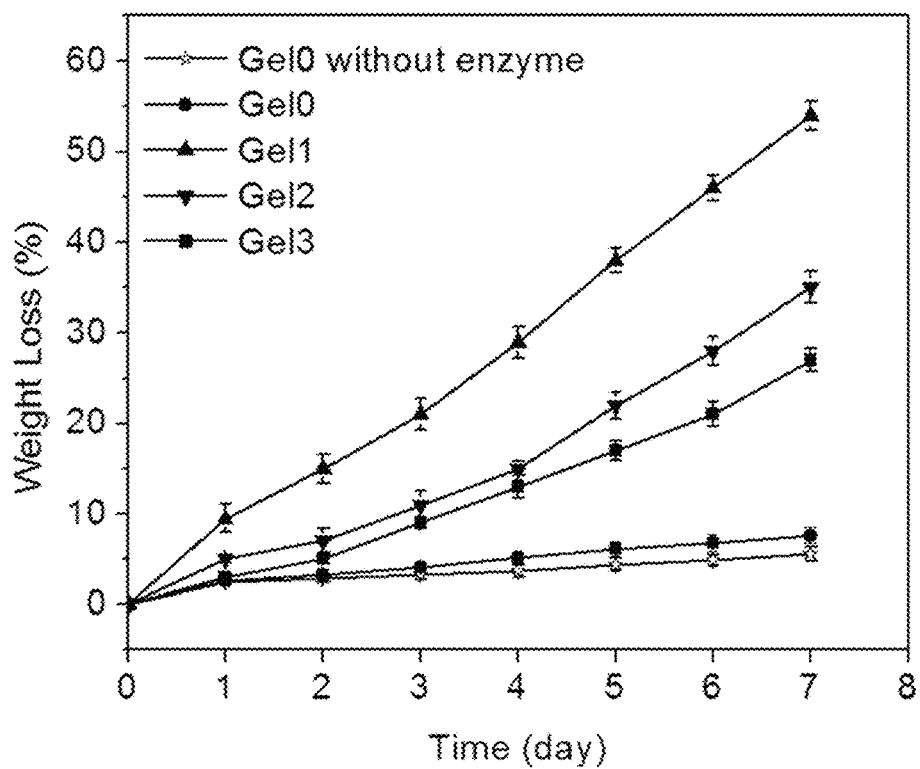
FIG. 9 shows representative weight loss of Dex-MA (Gel0) and Dex-MA/[2-Arg-4]-[2-Lys-4]-MA hybrid hydrogel, Gel1, Gel2, and Gel3 after 3 days biodegradation at 37° C. at the trypsin concentration of 0.1 mg/mL.
Figure 10:
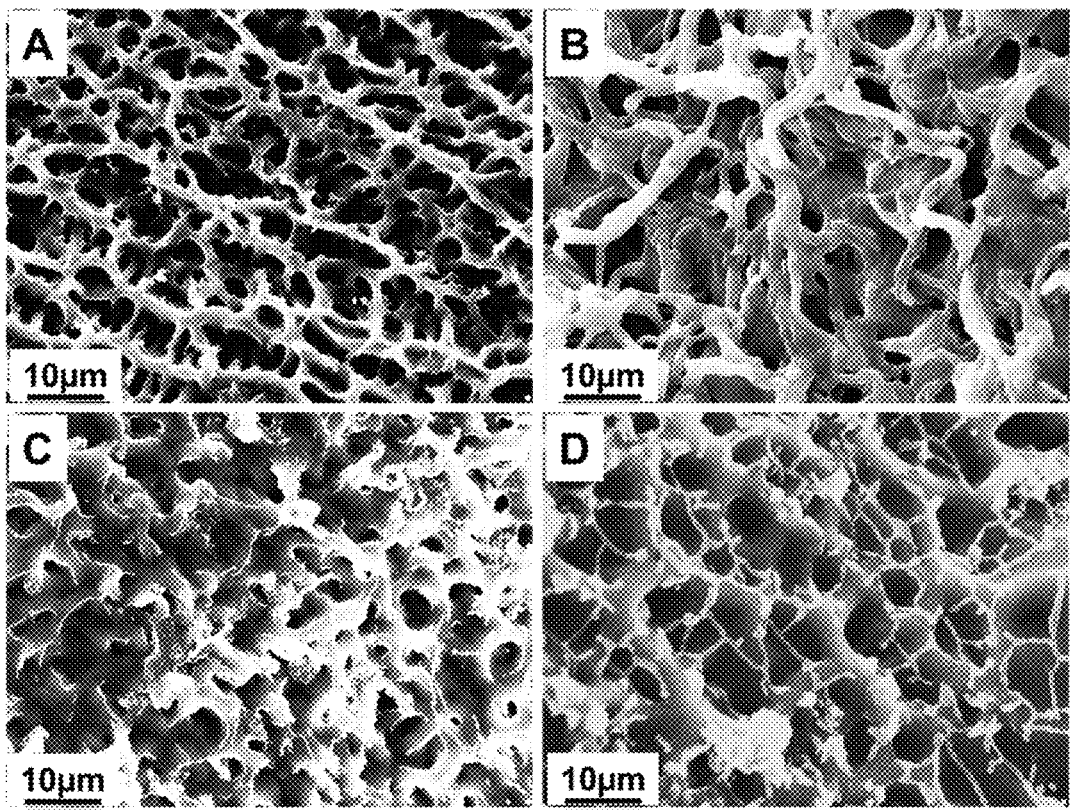
FIG. 10 shows representative SEM of Dex-MA(A) and Dex-MA/[2-Arg-4]-[2-Lys-4]-MA hybrid hydrogel, Gel1 (B), Gel2(C) and Gel3 (D) after 3 days biodegradation at the trypsin concentration of 0.1 mg/mL.
Figure 35:
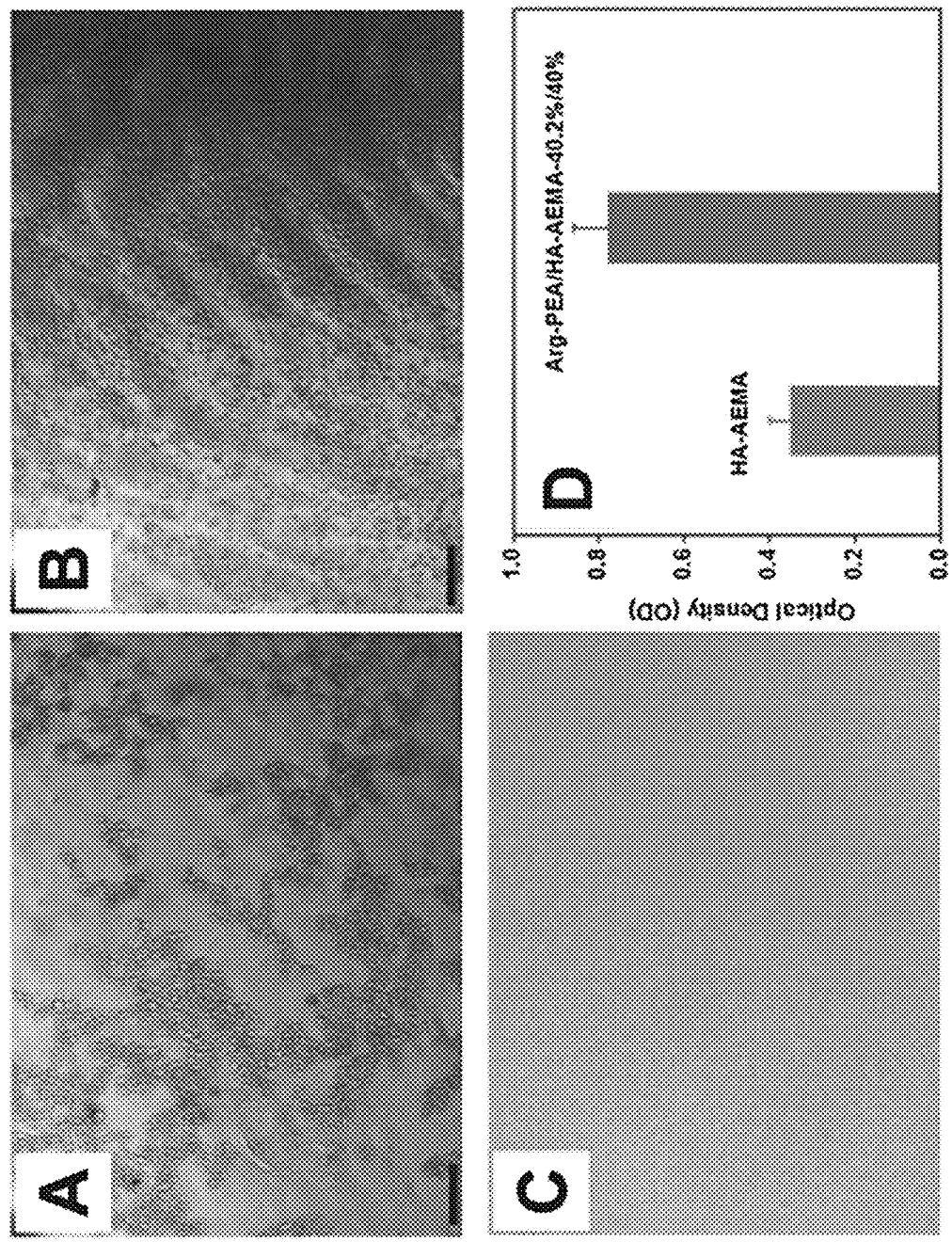
FIG. 35 shows representative micrographs of Hela cells after 48 hours culture. (A) Cells cultured on the surface of a pure HA-AEMA hydrogel (DS 40.2%); (B) cells cultured on the surface of the Arg-PEA/HA-AEMA-40.2%/40% hybrid hydrogel; (C) wet hydrogel after staining and washing as a blank control; (D) MTT assay for the Hela cells after 48 hours' culture in a DMEM medium on HA-AEMA (DS 40.2%) and Arg-PEA/HA-AEMA-40.2%/40% hybrid hydrogel surfaces.

Hela cell attachment and proliferation on HA-AEMA and Arg-PEA/HA-AEMA hybrid hydrogel surfaces. To study the cellular interaction with HA-AEMA and Arg-PEA/HA-AEMA hybrid hydrogels, Hela cells were cultured on the surface of these hydrogels to investigate the cell attachment and proliferation. Hela cells cultured on the pure HA-AEMA hydrogel were used as a control. FIG. 35B shows a representative example of the Hela cells cultured on the surface of the Arg-PEA/HA-AEMA-40.2%/40% hybrid hydrogel. When compared with the pure HA-AEMA hydrogel (FIG. 35A), Arg-PEA/HA-AEMA hybrid hydrogels had much higher amounts of the attached/proliferated Hela cells. No significant cellular morphology change was observed on the hybrid hydrogel surface (FIG. 35D) after 48 hours' culture. The Hela cells attached onto the pure HA-AEMA hydrogel surface, however, did show some morphology change (FIG. 35A). The data in FIG. 9A show that the Hela cells did not completely attach and spread on the HA-AEMA hydrogel surface. These qualitative cell morphological data were also confirmed by the quantitative MTT assay for the attached/proliferated Hela cells (FIG. 35D). Both FIGS. 35A and B show that the hybrid hydrogels have significantly higher amounts of attached and proliferated healthy Hela cells than the pure HA-AEMA hydrogel.

This enhancement in cell attachment and proliferation by incorporating AA-PEA co-precursors into another existing pure hydrogel system is consistent with using Arg-PEA co-precursors to enhance the Detroit 539 human fibroblast cell interaction with a pure pluronic acid hydrogel fabricated from F127. Arg-PEA/F127 hybrid hydrogels showed nearly 3.5 times more fibroblast proliferation than a pure F127 hydrogel.

Besides the use of a co-precursor approach to enhance the cell attachment/proliferation capability of HA-based hydrogels as reported in this example, others reported the use of nonco-precursor approaches to enhance cell interaction with HA hydrogels. Hela cells can more easily attach and proliferate on the Arg-PEA/HA-AEMA hybrid hydrogel surface without RGD and other factors introduced into the HA hydrogel.

Therefore, the introduction of Arg-PEA into the HA-AEMA hydrogel can significantly enhance the cellular interactions with the resulting hybrid hydrogel. The possible reasons for the observed enhancement in Hela cell attachment and proliferation on the Arg-PEA/HA-AEMA hybrid hydrogel surface can be attributed to the excellent cationic nature of the Arg-PEA component rather than the HA-AEMA hydrogel.

It is well known that hydrogel substrate mechanics, topography and surface chemistry are very important for cell attachment and proliferation. The hydrogel surface wettability was estimated by testing their contact angles, and the corresponding contact angles are 33.7° and 20.4° for HA-AEMA (DS 31.5%) and Arg-PEA/HA-AEMA-31.5%/40% hydrogels, respectively. As the content of the Arg-PEA component increased in the hybrids, the contact angles of the hybrids decreased due to the increased hydrophilicity of the Arg-PEA component in the hybrid hydrogels. The water contact angle decreased a little as the AEMA DS increased in the HA-AEMA component. Although the literature has shown that hydrogels having a more hydrophilic surface discourage the serum protein (in the cell culture medium) adsorption and hence show a lower level of cell attachment and proliferation, in this example, the more hydrophilic Arg-PEA/HA-AEMA hybrid hydrogels show far better Hela cell proliferation than a pure relatively more hydrophobic HA-AEMA hydrogel (FIG. 35D). The unique cationic characteristics of the Arg-PEA component in the Arg-PEA/HA-AEMA hybrid hydrogels are believed to be responsible for overriding the conventional accepted wettability on cell proliferation.

The role of substrate stiffness in cell behavior has also been suggested to be one of the major material factors to control cell attachment and proliferation. In this example, the Arg-PEA/HA-AEMA hybrid hydrogels have significantly lower compressive moduli than the pure HA-AEMA hydrogel (Table 9). Therefore, these hybrids should exhibit a lower level of cell proliferation than the pure HA-AEMA hydrogel. The Hela cell proliferation data in FIG. 35D show otherwise. Again, the unique cationic characteristics of the Arg-PEA component in the hybrid hydrogels appear to override the conventionally accepted effect of the substrate stiffness factor on cell behavior. Therefore, we suggest that the issue of the effect of substrate stiffness and wettability on cell proliferation is valid only if there is no charge in the substrates. If there are charges in the substrates, the charge factor could override stiffness and wettability factors toward cell proliferation.

The cell attachment and proliferation performances of Arg-PEA/HA-AEMA hybrid hydrogels suggest that they may have a great potential as a new type of scaffolds for various biomedical applications.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:
1. A hybrid hydrogel comprising:
 a) a plurality of covalently photocrosslinked functionalized polysaccharide molecules, wherein the functionalized polysaccharide molecules are selected from functionalized chitosan molecules having at least 10 pendant photocrosslinkable groups, functionalized hyaluronic acid molecules having at least 10 pendant photocrosslinkable groups, and functionalized dextran molecules having at least 10 pendant photocrosslinkable groups, and
 b) one or more functionalized poly(ester amide) polymer comprising the following:

—[AA]ₘ—[PXL1 or PXL2]ₙ— or —[PXL2]ₙ—[AA]ₘ—, wherein AA is:

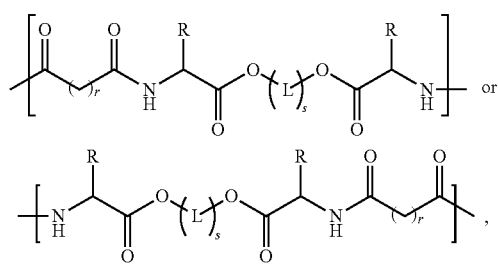

or

PXL1 is:

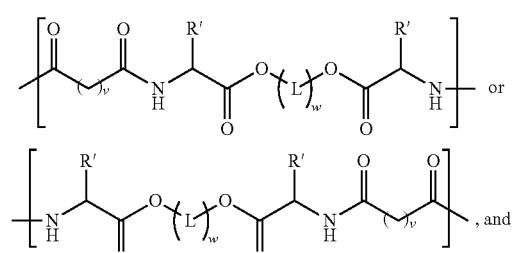

, and

PXL2 is:

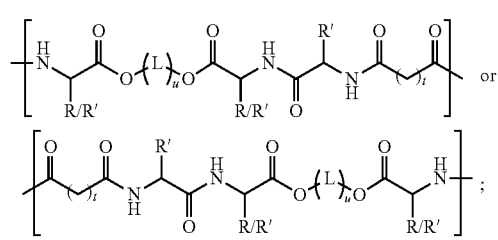

;

wherein L is —CH₂— or —CH₂CH₂—; R is the sidechain from any naturally occurring amino acid and at least one R group in each AA unit is an arginine sidechain; R' is a group covalently bound to one or more of the functionalized poly(ester amide) polymer or a functionalized polysaccharide molecule of the plurality of covalently photocrosslinked functionalized polysaccharide molecules, wherein R' has the following structure: —(CH₂)₄—NH—C(O)—CH(CH₃)—(CH₂)— or —(CH₂)₄—O—C(O)—CH(CH₃)—(CH₂)—; r is 2, 4, or 8; s is 2, 4, or 6; v is 2, 4, or 8; w is 2, 4, or 6, t is 2, 4, or 8; and u is 2, 4, or 6; and m/n is 4 to 1.

2. The hybrid hydrogel of claim 1, wherein the covalently photocrosslinked functionalized polysaccharide molecules are functionalized chitosan molecules having at least 10 pendant photocrosslinkable groups and the number of covalent bonds formed from photocrosslinking is 30 to 40% of the total hydroxyl and/or amine sites of the chitosan moieties and/or poly(ester amide) moieties.

3. The hybrid hydrogel of claim 1, wherein the covalently photocrosslinked functionalized polysaccharide molecules are functionalized hyaluronic acid having at least 10 pendant photocrosslinkable groups and the number of covalent bonds formed from photocrosslinking is 30 to 40% of the total hydroxyl and/or amine sites of the hyaluronic acid moieties and/or poly(ester amide) moieties.

4. The hybrid hydrogel of claim 1, wherein AA has the following structure:

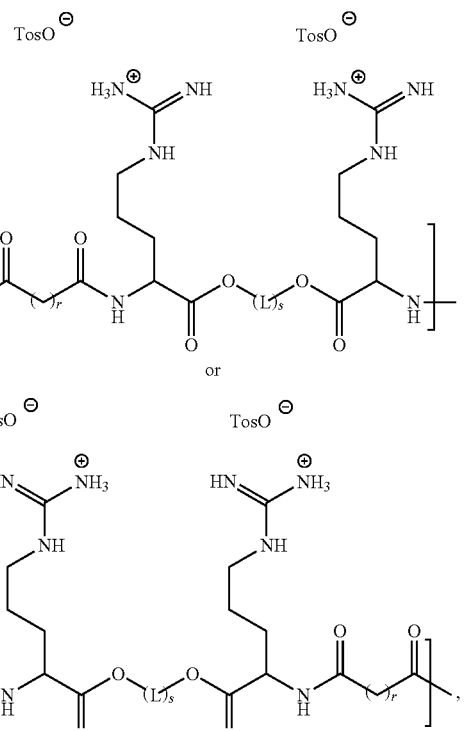

wherein L is —CH₂—.

5. The hybrid hydrogel of claim 1, wherein the one or more functionalized poly(ester amide) polymer and the functionalized polysaccharide molecules are photocrosslinked via one or more pendant photocrosslinkable functional groups.

6. The hybrid hydrogel of claim 1, wherein the pendant photocrosslinkable functional groups comprise a carbon-carbon double bond.

7. The hybrid hydrogel of claim 6, wherein the carbon-carbon double bond is selected from an allyl moiety, an vinyl moiety, and an methacrylate moiety.

8. A carrier material comprising:
a) a hybrid hydrogel comprising a plurality of covalently photocrosslinked functionalized polysaccharide molecules, wherein the functionalized polysaccharide molecules are selected from functionalized chitosan molecules having at least 10 pendant photocrosslinkable groups, functionalized hyaluronic acid molecules having at least 10 pendant photocrosslinkable groups, and functionalized dextran molecules having at least 10 pendant photocrosslinkable groups, and functionalized poly(ester amide) polymer comprising the following:

—[AA]ₘ—[PXL1 or PXL2]ₙ— or —[PXL2]ₙ—[AA]ₘ—, wherein AA is:

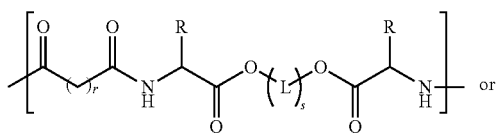

or

-continued

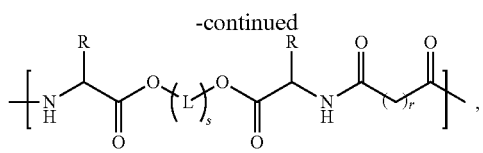

PXL1 is:

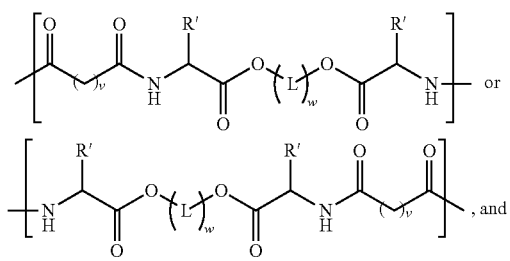

PXL2 is:

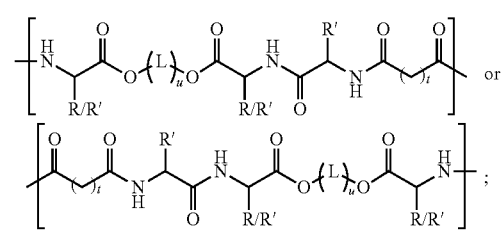

wherein L is —CH₂— or —CH₂CH₂—; R is the sidechain from any naturally occurring amino acid and at least one R group in each AA unit is an arginine sidechain; R' is a group covalently bound to one or more of the functionalized poly(ester amide) polymer or a functionalized polysaccharide molecule of the plurality of covalently photocrosslinked functionalized polysaccharide molecules, wherein R' has the following structure: —(CH₂)₄—NH—C(O)—CH(CH₃)—(CH₂)— or —(CH₂)₄—O—C(O)—CH(CH₃)—(CH₂)—; r is 2, 4, or 8; s is 2, 4, or 6; v is 2, 4, or 8; w is 2, 4, or 6, t is 2, 4, or 8; and u is 2, 4, or 6; and m/n is 4 to 1, and b) a cargo.

9. The carrier material of claim 8, wherein the cargo is a therapeutic agent or prophylactic agent.

10. The carrier material of claim 9, wherein the therapeutic agent or prophylactic agent is a nutrient, pharmaceutical, drug, peptide, polypeptide, oligonucleotide, polynucleotide, or combinations thereof.

11. The carrier material of claim 8, wherein the cargo is an absorbing material or a substrate in tissue engineering or cell culture.

12. An article of manufacture comprising a hydrogel comprising a hybrid hydrogel comprising a plurality of covalently photocrosslinked functionalized polysaccharide molecules, wherein the functionalized polysaccharide molecules are selected from functionalized chitosan molecules having at least 10 pendant photocrosslinkable groups; functionalized hyaluronic acid molecules having at least 10 pendant photocrosslinkable groups; and functionalized dextran molecules having at least 10 pendant photocrosslinkable groups, and functionalized poly(ester amide) polymer comprising the following:

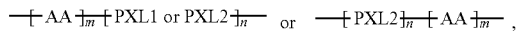

wherein AA is:

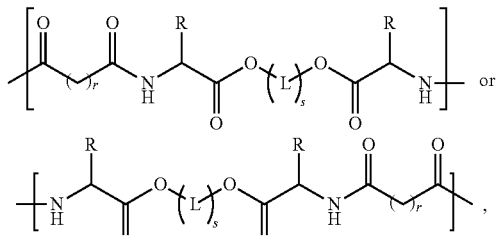

PXL1 is:

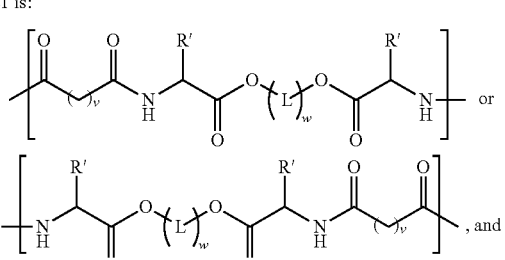

PXL2 is:

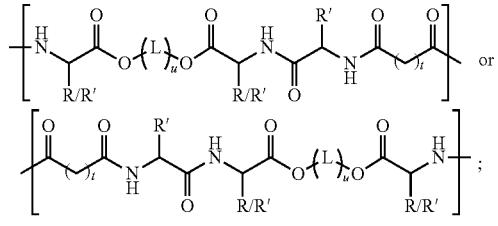

wherein L is —CH₂— or —CH₂CH₂—; R is the sidechain from any naturally occurring amino acid and at least one R group in each AA unit is an arginine sidechain; R' is a group covalently bound to one or more of the functionalized poly(ester amide) polymer or a functionalized polysaccharide molecule of the plurality of covalently photocrosslinked functionalized polysaccharide molecules, wherein R' has the following structure: —(CH₂)₄—NH—C(O)—CH(CH₃)—(CH₂)— or —(CH₂)₄—O—C(O)—CH(CH₃)—(CH₂)—; r is 2, 4, or 8; s is 2, 4, or 6; v is 2, 4, or 8; w is 2, 4, or 6, t is 2, 4, or 8; and u is 2, 4, or 6; and m/n is 4 to 1.

13. The article of manufacture of claim 12, wherein the article of manufacture is a diaper or tampon.

* * * * *

UNITED STATES PATENT AND TRADEMARK OFFICE
CERTIFICATE OF CORRECTION

PATENT NO. : 10,933,140 B2
APPLICATION NO. : 15/827245
DATED : March 2, 2021
INVENTOR(S) : Chu et al.

Page 1 of 4

It is certified that error appears in the above-identified patent and that said Letters Patent is hereby corrected as shown below:

In the Specification

Column 2, Line No. 58: "1=0.05)" should be --I=0.05)--

Column 2, Line No. 60: "1=0.05)" should be --I=0.05)--

Column 7, Line No. 38: "CH-Ph" should be --CH2-Ph--

Column 9, Line No. 65: "I" should be --1--

Column 18, Line No. 41: "asp-toluene," should be --as p-toluene--

Column 22, Line No. 32: "NCI," should be --(LiCl--

Column 23, Line No. (Approx.) 26:

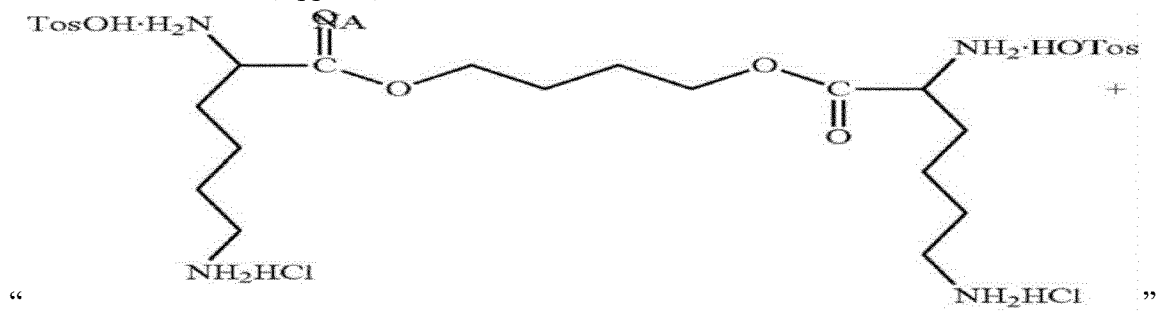

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*

Should be:
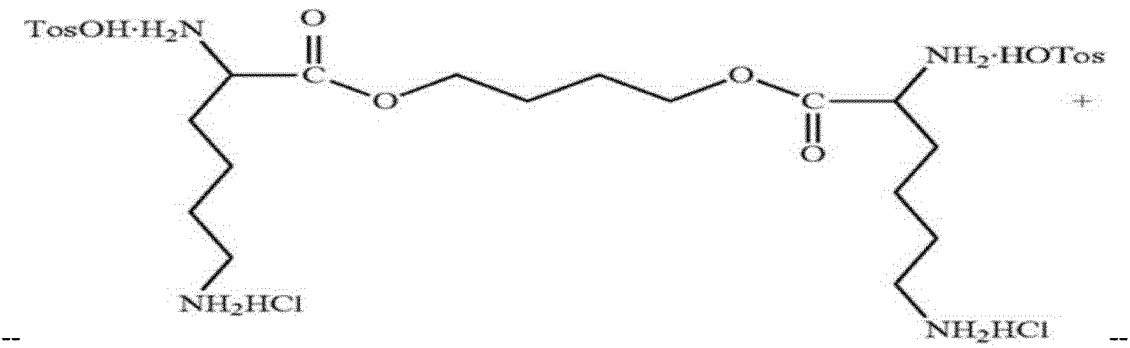
--
Column 28, Line No. 46: "W1" should be --Wt--
Column 30, Line No. 55: "W5" should be --Ws--
Column 31, Line No. 26: "W," should be --Wt--
Column 38, Line No. (Approx.) 2:
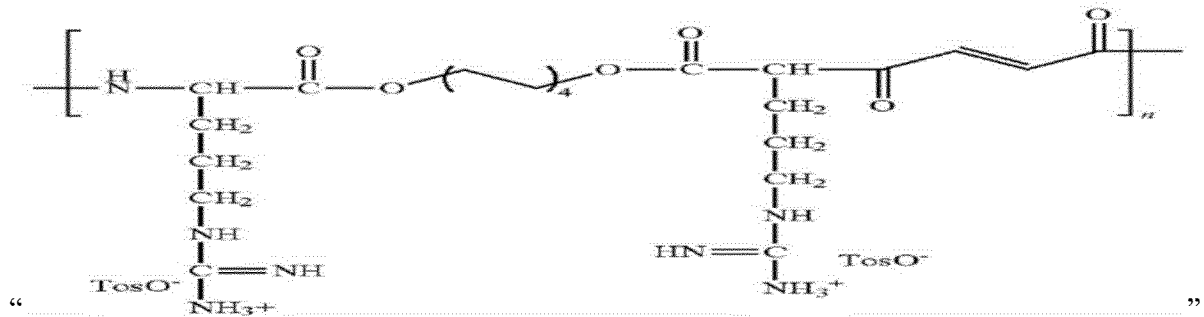
" "
Should be:
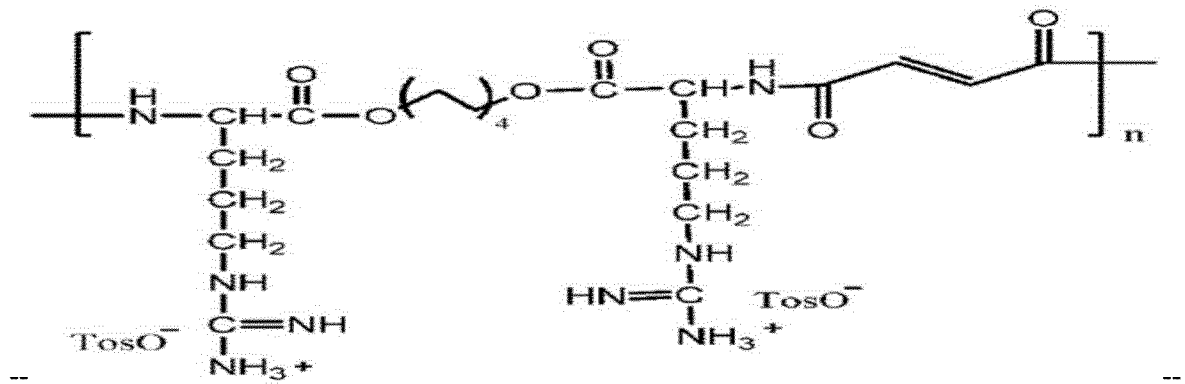
--

CERTIFICATE OF CORRECTION (continued)
U.S. Pat. No. 10,933,140 B2

Columns 37 - 38, Line No. (Approx.) 4:

"

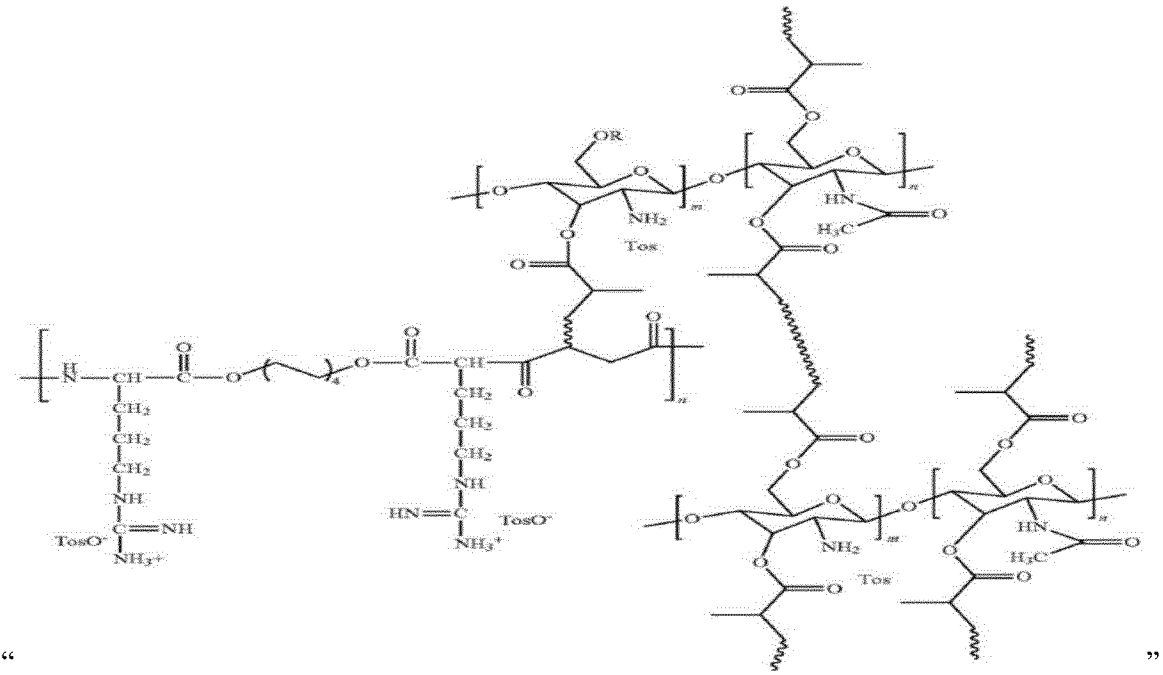

"

Should be:

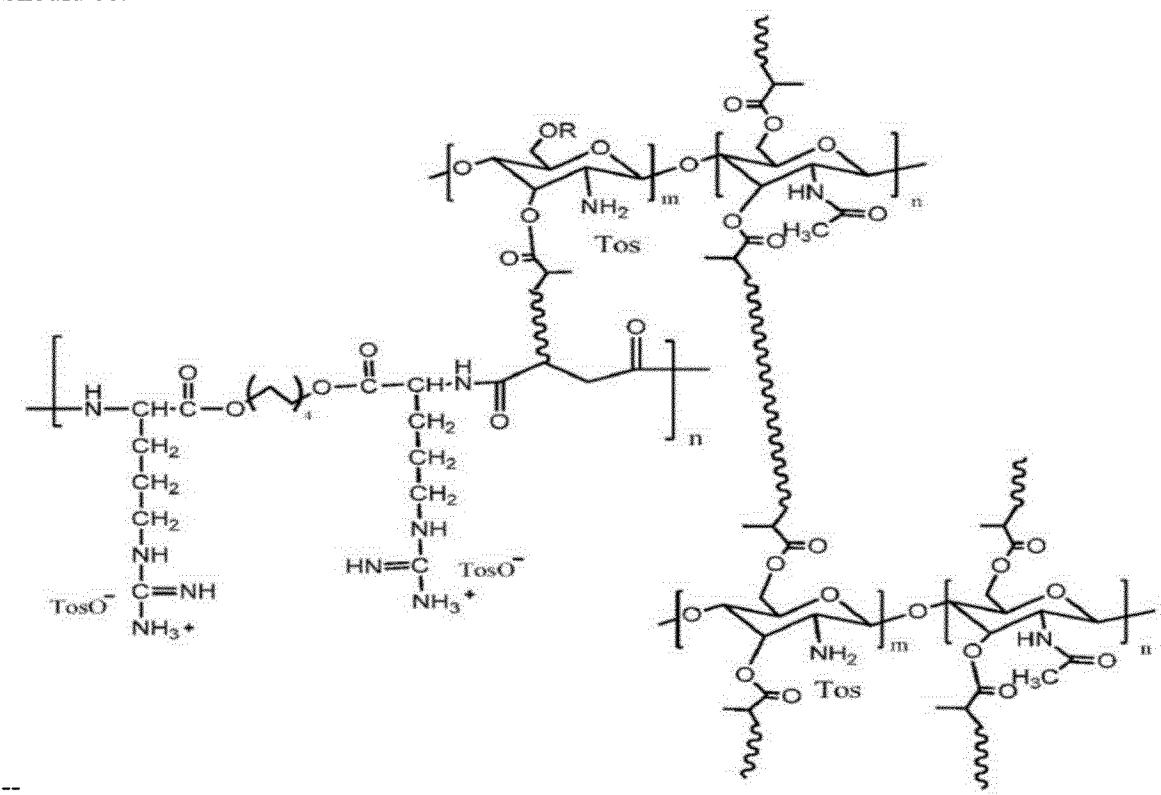

--                                                                                                                                --

Column 42, Line No. 21: "W1" should be --Wl--

Column 50, Line No. 66: "HA-A EMA" should be --HA-AEMA--

CERTIFICATE OF CORRECTION (continued)
U.S. Pat. No. 10,933,140 B2

Column 52, Line No. 42: "poly(c-caprolactone)" should be --poly(ε-caprolactone)--

Column 52, Line Nos. 44-45: "poly(E-caprolactone)" should be --poly(ε-caprolactone)--